(12) United States Patent
Kumar et al.

(10) Patent No.: US 7,166,357 B2
(45) Date of Patent: Jan. 23, 2007

(54) PHOTOCHROMIC ARTICLES THAT ACTIVATE BEHIND ULTRAVIOLET RADIATION BLOCKING TRANSPARENCIES AND METHODS FOR PREPARATION

(75) Inventors: Anil Kumar, Allegheny County, PA (US); Michael S. Misura, Westmoreland County, PA (US); Robert W. Walters, Westmoreland County, PA (US); Barry Van Gemert, Westmoreland County, PA (US); Anu Chopra, Allegheny County, PA (US); Clara E. Nelson, Allegheny County, PA (US)

(73) Assignee: Transitions Optical, Inc., Pinellas Park, FL (US)

( * ) Notice: Subject to any disclaimer, the term of this patent is extended or adjusted under 35 U.S.C. 154(b) by 8 days.

(21) Appl. No.: 10/393,179

(22) Filed: Mar. 20, 2003

(65) Prior Publication Data

US 2004/0185268 A1     Sep. 23, 2004

(51) Int. Cl.
*B32B 27/20*   (2006.01)
*B32B 27/30*   (2006.01)
*B32B 27/36*   (2006.01)
*B32B 27/38*   (2006.01)
*B32B 33/00*   (2006.01)

(52) U.S. Cl. .................. 428/411.1; 428/412; 428/413; 428/423.1; 428/426; 428/457; 428/480; 428/500; 428/522; 428/533; 428/537.1; 428/537.5

(58) Field of Classification Search ............ 428/411.1, 428/426, 457, 412, 413, 537.1, 537.5, 688, 428/522, 423.1, 500, 533, 480, 913; 252/586
See application file for complete search history.

(56) References Cited

U.S. PATENT DOCUMENTS

| | | | |
|---|---|---|---|
| 3,361,706 A | 1/1968 | Meriwether et al. ........... 260/39 |
| 4,166,043 A | 8/1979 | Uhlmann et al. ............ 252/300 |
| 4,367,170 A | 1/1983 | Uhlmann et al. ............ 252/586 |
| 4,609,267 A * | 9/1986 | Deguchi et al. ............ 351/163 |
| 4,931,220 A | 6/1990 | Haynes et al. ............. 252/586 |
| 5,166,345 A | 11/1992 | Akashi ........................ 544/71 |
| 5,236,958 A | 8/1993 | Miyashita ................... 518/121 |
| 5,252,742 A | 10/1993 | Miyashita ................... 548/121 |
| 5,359,085 A | 10/1994 | Iwamoto ..................... 548/468 |
| 5,488,119 A | 1/1996 | Fischer-Reimann et al. ..................... 552/201 |
| 5,645,767 A | 7/1997 | Van Gemert ................ 252/586 |
| 5,658,501 A | 8/1997 | Kumar et al. ............... 252/586 |
| 5,753,146 A | 5/1998 | Van Gemert et al. ....... 252/586 |
| 5,757,459 A * | 5/1998 | Bhalakia et al. ............ 351/168 |
| 5,808,063 A | 9/1998 | Kumar |
| 5,821,287 A | 10/1998 | Hu et al. ....................... 524/89 |
| 6,099,283 A * | 8/2000 | Soane et al. ................. 425/123 |
| 6,102,543 A | 8/2000 | Melzig ........................ 351/163 |
| 6,113,814 A | 9/2000 | Van Gemert et al. ....... 252/586 |
| 6,150,430 A | 11/2000 | Walters et al. ................. 522/79 |
| 6,153,126 A | 11/2000 | Kumar ........................ 252/586 |
| 6,296,785 B1 | 10/2001 | Nelson et al. .............. 252/586 |
| 6,348,604 B1 | 2/2002 | Nelson et al. .............. 549/389 |
| 6,353,102 B1 | 3/2002 | Kumar .......................... 544/60 |
| 6,555,028 B2 | 4/2003 | Walters et al. .............. 252/586 |

FOREIGN PATENT DOCUMENTS

| | | |
|---|---|---|
| DE | 10130489 A1 | 10/2002 |
| EP | 0686685 B1 | 2/1995 |
| WO | 97/05213 | 2/1997 |

OTHER PUBLICATIONS

Novel Indeno-Fused Photochromic Naphthopyrans, U.S. Appl. No. 10/039,984 filed Oct. 29, 2001.
Indeno-Fused Photochromic Naphthopyrans, Naphthols and Photochromic Articles, U.S. Appl. No. 10/393,177 filed Mar. 20, 2003.
Kirk-Othmer Encyclopedia of Chemical Technology, Fourth Edition, vol. 6, pp. 322-325.
Kirk-Othmer Encyclopedia of Chemical Technology, Fourth Edition, vol. 6, pp. 669-760.

* cited by examiner

*Primary Examiner*—Ramsey Zacharia
(74) *Attorney, Agent, or Firm*—Deborah M. Altman; Linda Pingitore; Frank P. Mallak

(57) ABSTRACT

Described are photochromic articles that include a substrate and a photochromic amount of at least one organic photochromic material (b) represented by graphic formula XIII adapted to change from an unactivated state to an activated state by exposure to radiation substantially in a wavelength range from 380 to 410 nanometers (nm) when measured over a wavelength range of from 380 to 700 nm. The photochromic articles demonstrate a photochromic response when activated behind an ultraviolet blocking transparency such as an automotive windshield. For example, the photochromic articles retain at least 12 percent of the activation measured as change in optical density or delta OD under outdoor simulating conditions in the Outdoor Test when tested under conditions simulating an eyeglass wearer behind an automotive windshield in the Behind the Windshield Test. Methods for producing the aforedescribed photochromic articles are also described.

74 Claims, 1 Drawing Sheet

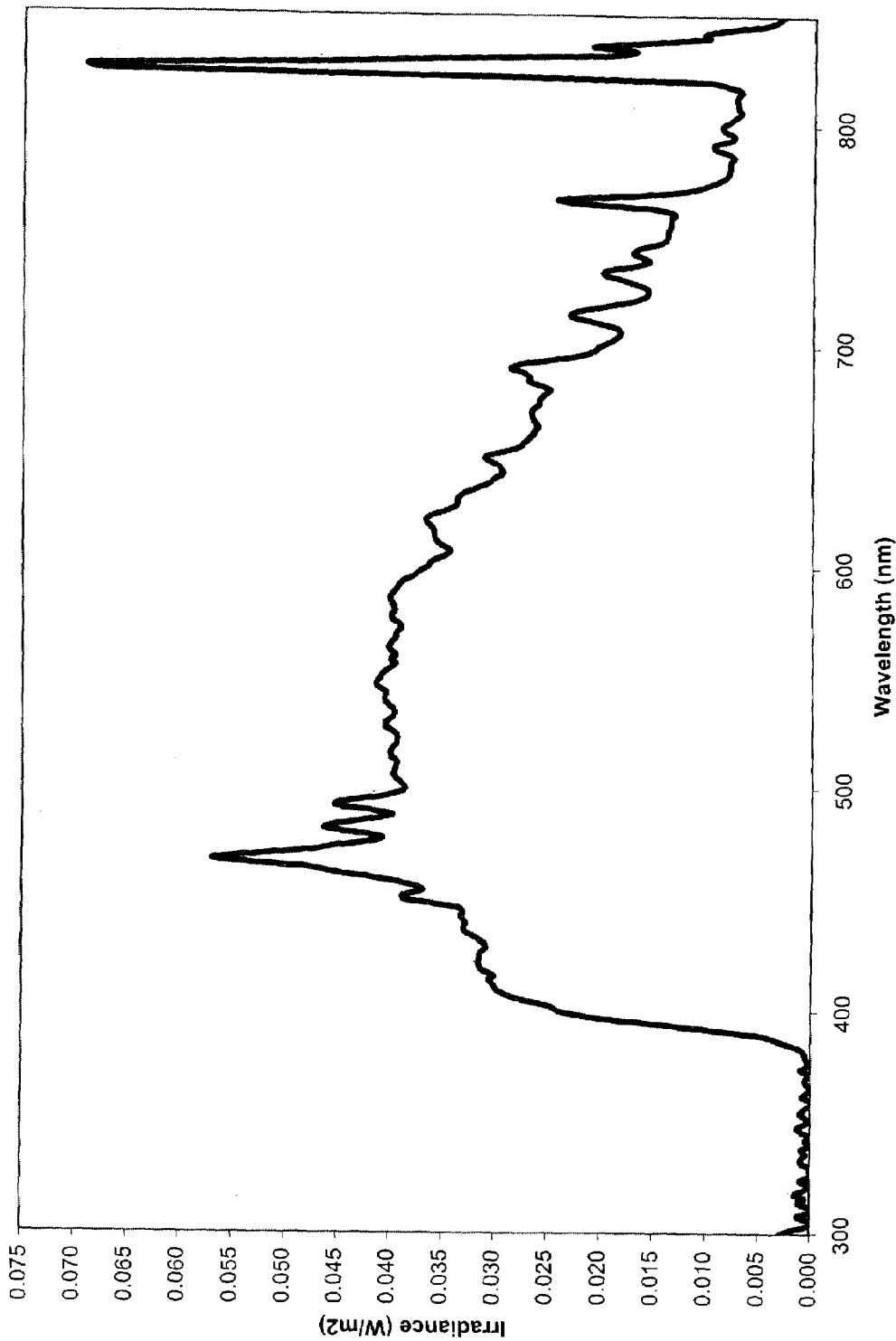
Figure 1. Transmission Spectrum of the Simulated Automotive Windshield

PHOTOCHROMIC ARTICLES THAT ACTIVATE BEHIND ULTRAVIOLET RADIATION BLOCKING TRANSPARENCIES AND METHODS FOR PREPARATION

BACKGROUND OF THE INVENTION

The present invention relates to novel photochromic articles that activate or become darker behind an ultraviolet radiation blocking transparency, e.g., an automotive windshield. More particularly, this invention relates to photochromic articles that demonstrate activated coloration or darkness when tested under conditions simulating an eyeglass wearer behind an automotive windshield and at least 70 percent transmittance in the unactivated state.

Photochromism is a phenomenon involving a light induced reversible change in color. An article containing such a material that becomes colored upon exposure to light radiation containing ultraviolet rays will revert to the original color when the influence of the ultraviolet radiation is discontinued. Sources of light radiation that contain ultraviolet rays include, for example, sunlight and the light of a mercury lamp. Discontinuation of the ultraviolet radiation can be achieved for example by storing the photochromic material or article in the dark or by removing the source of ultraviolet radiation, e.g., by means of filtering.

Typical photochromic articles do not activate or demonstrate negligible activation behind automotive windshields due to the limited ultraviolet radiation available for activation. A photochromic article that has been disclosed to function behind such ultraviolet radiation blocking transparencies includes photochromic compounds that activate by means of light in the visible spectrum. Such an article requires the presence of ultraviolet light absorbers to prevent the article from becoming too dark when not behind the windshield. The unactivated state of such an article is colored resulting in a percent transmission less than 70 percent.

The present invention provides a photochromic article that activates behind ultraviolet radiation blocking transparencies and a method for preparing such articles using photochromic materials that have been adapted to change from an unactivated form to an activated form by exposure to activating radiation substantially in the range of from 380 to 410 nanometers (nm), when such activating radiation is measured over a range from 380 to 700 nm.

BRIEF DESCRIPTION OF THE FIGURE

FIG. 1 shows the spectrum of the light passing through the automotive windshield simulating system used in the Behind the Windshield Test described herein in Example 13.

DETAILED DESCRIPTION OF THE INVENTION

It is noted that, as used in this specification and the appended claims, the singular forms "a," "an," and "the" include plural referents unless expressly and unequivocally limited to one referent.

For the purposes of this specification, unless otherwise indicated, all numbers expressing quantities of ingredients, reaction conditions, and other parameters used in the specification and claims are to be understood as being modified in all instances by the term "about". Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

The phrase "an at least partial coating" means an amount of coating covering from a portion to the complete surface of the substrate. The phrase "an at least partially cured coating" refers to a coating in which the curable or crosslinkable components are from at least partially cured up to fully cured, crosslinked and/or reacted. In alternate non-limiting embodiments of the present invention, the degree of reacted components can vary widely, e.g., from 5% to 100% of all the possible curable, crosslinkable and/or reactable components.

The phrase "an at least partially abrasion resistant coating or film" refers to a coating or film that demonstrates a resistance to abrasion that is greater than the standard reference material, typically a plastic made of CR-39® monomer available from PPG Industries, Inc, as tested in a method comparable to ASTM F-735 Standard Test Method for Abrasion Resistance of Transparent Plastics and Coatings Using the Oscillating Sand Method. The phrase "an at least partially antireflective coating" is a coating that at least partially improves the antireflective nature of the surface to which it is applied by increasing the percent transmittance as compared to an uncoated surface. The improvement in percent transmittance can range from 1 to 9 percent above the uncoated surface. Put another way, the percent transmittance of the coated surface can range from a percentage greater than the uncoated surface up to 99.9.

In one non-limiting embodiment, the use of at least one photochromic material adapted to change from an unactivated form to an activated form by exposure to activating radiation substantially in the wavelength range of from 380 to 410 nm in a photochromic article tested in the Behind the Windshield Test adapts the photochromic article to retain at least 12 percent of the coloration, measured as delta OD or ΔOD, that would have occurred if the adapted photochromic article was activated under conditions simulating outdoor exposure as described in the Outdoor Test in Example 13 herein.

In another non-limiting embodiment, the adapted photochromic article retains at least 20 percent of the coloration. In a further non-limiting embodiment, the adapted photochromic article retains at least 25 percent of the coloration exhibited in the Outdoor Test when tested in the Behind the Windshield Test. The coloration or percent ΔOD retained by the adapted photochromic article of the present invention can range between any combination of these values, inclusive of the recited range, e.g., from 12 to 100 percent, or from 20 to 90 percent or from 25 to 50 percent.

In an alternate non-limiting embodiment, the photochromic article of the present invention is adapted to exhibit an unactivated state luminous transmittance of greater than 70 percent at 23° C., an activated state luminous transmittance at saturation less than 30 percent when activated at 23° C. by simulated sunlight from a xenon arc lamp set at 6.7 Watts/ meter² UVA and 50,000 lumens/meter², and an activated state luminous transmittance at saturation less than 60 percent when activated at 28° C. by simulated sunlight from a xenon arc lamp through an UV blocking transparency rendering an irradiance integrated between 380 and 420 nanometers of 0.75 Watts/meter² and 1,700 lumens/meter².

In another non-limiting embodiment, the photochromic article of the present invention is adapted to exhibit an unactivated state luminous transmittance of greater than 80 percent at 23° C., an activated state luminous transmittance at saturation less than 30 percent when activated at 23° C. by simulated sunlight from a xenon arc lamp set at 6.7 Watts/meter² UVA and 50,000 lumens/meter², and an activated state luminous transmittance at saturation less than 40 percent when activated at 28° C. by simulated sunlight from a xenon arc lamp through an UV blocking transparency rendering an irradiance integrated between 380 and 420 nanometers of 0.75 Watts/meter² and 1,700 lumens/meter².

In the aforementioned alternate non-limiting embodiment, the photochromic articles reach saturation within 15 to 30 minutes of exposure to the simulated sunlight and/or simulated sunlight filtered by the UV radiation blocking transparency at 23° C. and 28° C. The term "activated luminous state transmittance at saturation" means that the transmittance of the photochromic article has reached a point where it will not substantially change due to continued exposure to simulated sunlight. Stated another way, the transmittance at saturation upon continued exposure to activating radiation does not vary by more than 5 percent of the percent transmittance value.

The aforementioned unactivated state luminous transmittance at 23° C. can range between any of the aforestated values, e.g., from 70.1 to 100 percent or from 80.1 to 100 percent, and their inclusive values, e.g., from 71 to 99 percent or from 81 to 99 percent. The activated state luminous transmittance at saturation when the photochromic article is activated at 23° C. by simulated sunlight from a xenon arc lamp set at 6.7 Watts/meter² UVA and 50,000 lumens/meter² can range between the aforestated values, e.g., from 29.9 to 0 percent, and their inclusive values, e.g., from 29 to 10 percent, or from 25 to 15 percent. The activated state luminous transmittance at saturation when the photochromic article is activated at 28° C. by simulated sunlight from a xenon arc lamp through an UV blocking transparency rendering an irradiance integrated between 380 and 420 nanometers of 0.75 Watts/meter² and 1,700 lumens/meter². can range between any of the aforestated values, e.g., from 0 to less than 60 percent, e.g., 59.9 percent, or from 0 to less than 40 percent e.g., 39.9 percent, and their inclusive values, e.g., from 1 to 59 percent, or from 10 to 50 percent or from 15 to 40 percent.

The photochromic materials used to adapt the photochromic article for activation behind ultraviolet radiation blocking transparencies are referred to herein as Behind the Windshield photochromic materials or BWS photochromic materials.

The Behind the Windshield Test and the Outdoor Test are described in Example 13 herein. Basically, test samples containing BWS photochromic materials with or without other photochromic materials are tested for photochromic response, e.g., the change in optical density, with the simulated windshield in place under conditions simulating an eyeglass wearer behind an automotive windshield exposure (BWS) versus conditions simulating outdoor exposure in the Outdoor Test (OS). The retained optical density is calculated by using the following formula:

$$\%\Delta OD \text{ Retained} = 100 \times (\Delta OD_{BWS}/\Delta OD_{OS}).$$

In one non-limiting embodiment, the photochromic articles of the present invention are substantially free of ultraviolet absorbing materials in concentrations that would substantially inhibit the activation of the photochromic materials by radiation below 380 nanometers. In an alternate non-limiting embodiment, the photochromic articles of the present invention do not contain ultraviolet absorbing materials in concentrations that would prevent greater than 50 percent of the activation of the photochromic materials, as measured by delta OD by radiation below 380 nanometers.

In a series of non-limiting embodiments, the BWS photochromic materials of the present invention include photochromic materials adapted to change from an unactivated form to an activated form by exposure to radiation substantially in the wavelength range from 380 to 410 nanometers when measured over a range of from 380 to 700 nanometers. Classes of photochromic materials that can include BWS photochromic materials include naphthopyrans, benzopyrans, phenanthropyrans, indenonaphthopyrans, oxazines, metal-dithiozonates, fulgides, fulgimides, spiro(indoline) pyrans or mixtures thereof. In one non-limiting embodiment, the BWS materials are chosen from the photochromic materials represented by graphic formula XIII and mixtures thereof with the other photochromic materials. In the definitions of the substituents shown in formulae I to XIV, like symbols have the same meaning unless stated otherwise.

In one non-limiting embodiment, a photochromic material is chosen from a fluoranthenoxazine represented by the following graphic formula I:

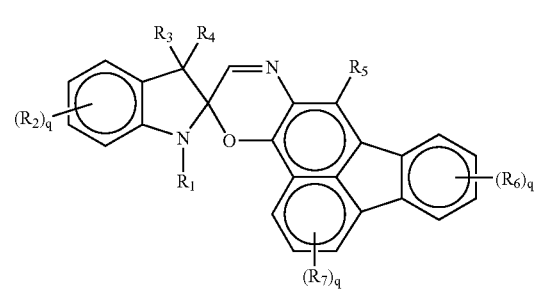

wherein, (a) $R_1$ is chosen from hydrogen, $C_1$–$C_8$ alkyl, $C_3$–$C_7$ cycloalkyl, phen($C_1$–$C_4$)alkyl, naphth($C_1$–$C_4$)alkyl, allyl, acrylyloxy($C_2$–$C_6$)alkyl, methacrylyloxy($C_2$–$C_6$)alkyl, $C_2$–$C_4$acyloxy ($C_2$–$C_6$)alkyl, carboxy($C_2$–$C_6$)alkyl, cyano ($C_2$–$C_6$)alkyl, hydroxy($C_2$–$C_6$)alkyl, triarylsilyl, triarylsilyloxy, tri($C_1$–$C_6$)alkylsilyl, tri($C_1$–$C_6$)alkylsilyloxy, tri ($C_1$–$C_6$)alkoxysilyl, tri($C_1$–$C_6$)alkoxysilyloxy, di($C_1$–$C_6$) alkyl($C_1$–$C_6$ aloxy)silyl, di($C_1$–$C_6$)alkyl($C_1$–$C_6$aloxy) silyloxy, di($C_1$–$C_6$)alkoxy($C_1$–$C_6$alkyl)silyl, di($C_1$–$C_6$) alkoxy($C_1$–$C_6$ alkyl)silyloxy, $C_1$–$C_6$ alkoxy($C_2$–$C_4$)alkyl or $(C_2H_4O)_r$.$CH_3$, wherein r is an integer from 1 to 6;

(b) $R_2$ is chosen from $C_1$–$C_5$ alkyl, $C_1$–$C_5$ alkoxy, nitro, cyano, $C_1$–$C_8$ alkoxycarbonyl, $C_1$–$C_4$ acyloxy, halo, $C_1$–$C_4$ monohaloalkyl or $C_1$–$C_4$ polyhaloalkyl; said halo substituents being chloro, fluoro, iodo or bromo and q is 0, 1 or 2;

(c) $R_3$ and $R_4$ are each independently chosen from $C_1$–$C_5$ alkyl, benzyl, phenyl, mono- or di-substituted phenyl, said phenyl substituents being $C_1$–$C_5$ alkyl or $C_1$–$C_5$ alkoxy; or $R_3$ and $R_4$ taken together form a group chosen from a cyclic ring of from 5 to 8 carbon atoms which includes the spiro carbon atom; examples of such groups include norbornyl or adamantyl;

(d) $R_5$ is chosen from hydrogen, —$CH_2Q$ and —$C(O)W$, wherein Q is halogen, hydroxy, benzoyloxy, $C_1$–$C_6$ alkoxy, triarylsilyl, triarylsilyloxy, tri($C_1$–$C_6$)alkylsilyl, tri($C_1$–$C_6$)alkylsilyloxy, tri($C_1$–$C_6$)alkoxysilyl, tri($C_1$–$C_6$)alkoxysilyloxy, di($C_1$–$C_6$)alkyl($C_1$–$C_6$ aloxy)silyl, di($C_1$–$C_6$)alkyl($C_1$–$C_6$ alkoxy)silyloxy, di($C_1$–$C_6$)alkoxy($C_1$–$C_6$ alkyl)silyl, di($C_1$–$C_6$)alkoxy($C_1$–$C_6$ alkyl)silyloxy, $C_2$–$C_6$ acyloxy, amino, $C_1$–$C_6$ mono-alkylamino, $C_1$–$C_6$ dialkylamino, morpholino, piperidino, 1-indolinyl, pyrrolidyl, or the group, —$OCH(R_8)Z$; W is the group, —$OCH(R_8)Z$, or an unsubstituted, mono-substituted, or di-substituted heterocyclic ring containing 5 to 6 ring atoms, which ring includes as the hetero atom a nitrogen atom alone or one additional hetero atom of nitrogen or oxygen; examples of such heterocyclic rings include 1-indolinyl, morpholino, piperidino, 1-pyrrolidyl, 1-imidazolidyl, 2-imidazolin-1-yl, pyrazolidyl, pyrazolinyl or 1-piperazinyl; wherein Z is —CN, —$CF_3$, halogen, —$C(O)R_8$, or —$COOR_8$, $R_8$ is hydrogen or $C_1$–$C_6$ alkyl; said heterocyclic ring substituents being chosen from $C_1$–$C_6$ alkyl or $C_1$–$C_6$ alkoxy; or W is —$OR_9$ or —$N(R_{10})R_{11}$, wherein $R_9$ is chosen from hydrogen, allyl, $C_1$–$C_6$ alkyl, phenyl, mono($C_1$–$C_6$)alkyl substituted phenyl, mono($C_1$–$C_6$)alkoxy-substituted phenyl, phenyl($C_1$–$C_3$)alkyl, mono($C_1$–$C_6$)alkyl substituted phenyl($C_1$–$C_3$)alkyl, mono($C_1$–$C_6$)alkoxy substituted phenyl($C_1$–$C_3$)alkyl, $C_1$–$C_6$ alkoxy($C_2$–$C_4$)alkyl, or $C_1$–$C_6$ haloalkyl; and $R_{10}$ and $R_{11}$ are each independently chosen from hydrogen, $C_1$–$C_6$ alkyl, $C_5$–$C_7$ cycloalkyl, phenyl, mono- or di-substituted phenyl, or $R_{10}$ and $R_{11}$ together with the nitrogen atom form a mono- or di-substituted or unsubstituted heterocyclic ring containing from 5 to 6 ring atoms, which ring includes as the hetero atom said nitrogen atom alone or one additional hetero atom of nitrogen or oxygen, said phenyl and heterocyclic ring substituents being $C_1$–$C_6$ alkyl or $C_1$–$C_6$ alkoxy, and each of said halogen or halo groups in this part (d) being fluoro or chloro;

(e) each $R_6$ and $R_7$ is independently chosen for each occurrence from aryl, mono($C_1$–$C_6$)alkoxyaryl, di($C_1$–$C_6$)alkoxyaryl, mono($C_1$–$C_6$)alkylaryl, di($C_1$–$C_6$)alkylaryl, bromoaryl, chloroaryl, fluoroaryl, $C_3$–$C_7$ cycloalkylaryl, $C_3$–$C_7$ cycloalkyl, $C_3$–$C_7$ cycloalkyloxy, $C_3$–$C_7$ cycloalkyloxy($C_1$–$C_6$)alkyl, $C_3$–$C_7$ cycloalkyloxy($C_1$–$C_6$)alkoxy, aryl($C_1$–$C_6$)alkyl, aryl($C_1$–$C_6$)alkoxy, aryloxy, aryloxy($C_1$–$C_6$)alkyl, aryloxy($C_1$–$C_6$)alkoxy, mono- or di($C_1$–$C_6$)alkylaryl($C_1$–$C_6$)alkyl, mono- or di($C_1$–$C_6$)alkoxyaryl($C_1$–$C_6$)alkyl, mono- or di($C_1$–$C_6$)alkylaryl($C_1$–$C_6$)alkoxy, mono- or di($C_1$–$C_6$)alkoxyaryl($C_1$–$C_6$)alkoxy, amino, mono($C_1$–$C_6$)alkylamino, di($C_1$–$C_6$)alkylamino, diarylamino, N-($C_1$–$C_6$)alkylpiperazino, N-arylpiperazino, aziridino, indolino, piperidino, arylpiperidino, morpholino, thiomorpholino, tetrahydroquinolino, tetrahydroisoquinolino, pyrryl, $C_1$–$C_6$ alkyl, $C_1$–$C_6$ bromoalkyl, $C_1$–$C_6$ chloroalkyl, $C_1$–$C_6$ fluoroalkyl, $C_1$–$C_6$ alkoxy, mono($C_1$–$C_6$)alkoxy($C_1$–$C_4$)alkyl, acryloxy, methacryloxy, bromo, chloro or fluoro; and q is independently chosen for each occurrence form the integer 0, 1, or 2.

In another non-limiting embodiment, the fluoranthenoxazine is represented by graphic formula I wherein:

(a) $R_1$ is chosen from $C_1$–$C_8$ alkyl, phen($C_1$–$C_4$)alkyl, acryloyloxy($C_2$–$C_6$)alkyl, methacryloyloxy($C_2$–$C_6$)alkyl, carboxy($C_2$–$C_6$)alkyl, tri($C_1$–$C_6$)alkylsilyl, tri($C_1$–$C_6$)alkylsilyloxy, tri($C_1$–$C_6$)alkoxysilyl, tri($C_1$–$C_6$)alkoxysilyloxy, di($C_1$–$C_6$)alkyl($C_1$–$C_6$ aloxy)silyl, di($C_1$–$C_6$)alkyl($C_1$–$C_6$ aloxy)silyloxy, di($C_1$–$C_6$)alkoxy($C_1$–$C_6$alkyl)silyl or di($C_1$–$C_6$)alkoxy($C_1$–$C_6$alkyl)silyloxy;

(b) $R_2$ is chosen from $C_1$–$C_5$ alkyl, $C_1$–$C_5$ alkoxy, $C_1$–$C_8$ alkoxycarbonyl, $C_1$–$C_4$ acyloxy, halo, $C_1$–$C_4$ monohaloalkyl or $C_1$–$C_4$ polyhaloalkyl; said halo substituents being chloro or fluoro, and q is 0, 1 or 2;

(c) $R_3$ and $R_4$ are each independently chosen from $C_1$–$C_5$ alkyl, phenyl; or $R_3$ and $R_4$ taken together form a group chosen from a cyclic ring of from 5 to 8 carbon atoms which includes the spiro carbon atom;

(d) $R_5$ is chosen from —$CH_2Q$ and —$C(O)W$, wherein Q is halogen, hydroxy, $C_1$–$C_6$ alkoxy, tri($C_1$–$C_6$)alkylsilyl, tri($C_1$–$C_6$)alkylsilyloxy, tri($C_1$–$C_6$)alkoxysilyl, tri($C_1$–$C_6$)alkoxysilyloxy, di($C_1$–$C_6$)alkyl($C_1$–$C_6$ aloxy)silyl, di($C_1$–$C_6$)alkyl($C_1$–$C_6$ aloxy)silyloxy, di($C_1$–$C_6$)alkoxy($C_1$–$C_6$ alkyl)silyl, di($C_1$–$C_6$)alkoxy($C_1$–$C_6$ alkyl)silyloxy or the group, —$OCH(R_8)Z$; W is the group, —$OCH(R_8)Z$, morpholino or piperidino; Z is —$COOR_8$, $R_8$ is $C_1$–$C_6$ alkyl; or W is —$OR_9$ or —$N(R_{10})R_{11}$, wherein $R_9$ is chosen from $C_1$–$C_6$ alkyl or phenyl; and $R_{10}$ and $R_{11}$ are each independently chosen from hydrogen, $C_1$–$C_6$ alkyl, or $R_{10}$ and $R_{11}$ together with the nitrogen atom form a heterocyclic ring chosen from morpholino or piperidino; and each of said halogen or halo groups in this part (d) being fluoro or chloro;

(e) each $R_6$ and $R_7$ is independently chosen for each occurrence from aryl, mono($C_1$–$C_6$)alkoxyaryl, di($C_1$–$C_6$)alkylamino, piperidino, morpholino, $C_1$–$C_6$ alkoxy, or fluoro; and q is independently chosen for each occurrence form the integer 0, 1, or 2.

In a further non-limiting embodiment, the fluoranthenoxazine represented by graphic formula I is chosen from:

(a) 1,3,3-trimethyl-spiro[indoline-2,5'-[3H]-fluorantheno[3,2-b][1,4]oxazine];

(b) 1,3,3,4,5 (or 1,3,3,5,6)-pentamethyl-spiro[indoline-2,5'-[3H]-fluorantheno[3,2-b][1,4]oxazine];

(c) 1-propyl-3,3,4,5 (or 3,3,5,6)-tetramethyl-spiro[indoline-2,5'-[3H]-fluorantheno[3,2-b][1,4]oxazine];

(d) 1-methoxyethyl-3,3-dimethyl-spiro[indoline-2,5'-[3H]-fluorantheno[3,2-b][1,4]oxazine]; or (e) mixtures thereof.

The materials represented by graphic formula I can be produced by methods known to those skilled in the art, for example, as disclosed in U.S. Pat. No. 5,808,063

In one non-limiting embodiment, a photochromic material is chosen from a naphthopyran represented by the following graphic formula II:

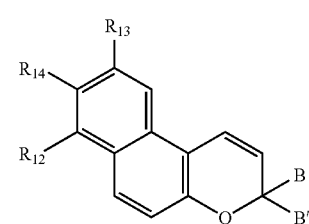

wherein:

(a) $R_{12}$ is hydrogen or a $C_1$–$C_6$ alkyl;

(b) $R_{13}$ is hydrogen or the group, —$C(O)J$, J being —$OR_{15}$ or —$N(R_{10})R_{11}$, wherein $R_{15}$ is hydrogen, allyl, $C_1$–$C_6$ alkyl, phenyl, $C_1$–$C_6$ monoalkyl substituted phenyl, $C_1$–$C_6$ monoalkoxy substituted phenyl, phenyl($C_1$–$C_3$)alkyl, $C_1$–$C_6$ monoalkyl substituted phenyl($C_1$–$C_3$)alkyl, $C_1$–$C_6$ monoalkoxy substituted phenyl($C_1$–$C_3$)alkyl, $C_1$–$C_6$ alkoxy ($C_2$–$C_4$)alkyl, or $C_1$–$C_6$ monohaloalkyl, and wherein $R_{10}$ and $R_{11}$ are the same as described hereinbefore in (d) for the material represented by graphic formula I, and said halo substituent being chloro or fluoro;

(c) $R_{14}$ is —$OR_9$, —$N(R_{10})R_{11}$, wherein $R_9$, $R_{10}$ and $R_{11}$ are the same as described hereinbefore in (d) for the material represented by graphic formula I, or the group, —C(O)V; wherein V is $C_1$–$C_6$ alkyl, phenyl, $C_1$–$C_6$ mono- or $C_1$–$C_6$ di-alkyl substituted phenyl, $C_1$–$C_6$ mono- or $C_1$–$C_6$ di-alkoxy substituted phenyl, $C_1$–$C_6$ alkoxy, phenoxy, $C_1$–$C_6$ mono- or $C_1$–$C_6$ di-alkyl substituted phenoxy, $C_1$–$C_6$ mono- or $C_1$–$C_6$ di-alkoxy substituted phenoxy, $C_1$–$C_6$ alkylamino, phenylamino, $C_1$–$C_6$ mono- or $C_1$–$C_6$ di-alkyl substituted phenylamino, or $C_1$–$C_6$ mono- or $C_1$–$C_6$ di-alkoxy substituted phenylamino, and said halo substituent being chloro, fluoro or bromo, provided that either $R_{12}$ or $R_{13}$ is hydrogen; and (d) B and B' are each independently chosen from:
(i) mono-T-substituted phenyl, wherein the group T is represented by the formula:

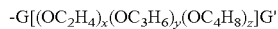

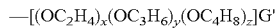

wherein -G being chosen from —C(O)— or —$CH_2$—, G' being chosen from $C_1$–$C_3$ alkoxy or a polymerizable group, x, y and z each being independently chosen from a number between 0 and 50, and the sum of x, y and z being between 2 and 50;

(ii) an unsubstituted, mono-, di-, or tri-substituted aryl group, phenyl or naphthyl;
(iii) 9-julolidinyl or the unsubstituted, mono- or di-substituted heteroaromatic group chosen from pyridyl furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl or fluorenyl, each of said aryl and heteroaromatic substituents in (ii) and (iii) being independently chosen from hydroxy, —C(O)U, wherein U being hydroxy, $C_1$–$C_6$ alkyl, $C_1$–$C_6$ alkoxy, phenyl, mono-substituted phenyl, amino, mono ($C_1$–$C_6$)alkylamino, di-($C_1$–$C_6$) alkylamino, morpholino, piperidino or pyrrolidyl; aryl, mono($C_1$–$C_6$)alkoxyaryl, di($C_1$–$C_6$)alkoxyaryl, mono ($C_1$–$C_6$)alkylaryl, di($C_1$–$C_6$)alkylaryl, chloroaryl, fluoroaryl, $C_3$–$C_7$ cycloalkylaryl, $C_3$–$C_7$ cycloalkyl, $C_3$–$C_7$ cycloalkyloxy, $C_3$–$C_7$ cycloalkyloxy($C_1$–$C_6$)alkyl, $C_3$–$C_7$ cycloalkyloxy($C_1$–$C_6$)alkoxy, aryl($C_1$–$C_6$)alkyl, aryl($C_1$–$C_6$)alkoxy, aryloxy, aryloxy($C_1$–$C_6$)alkyl, aryloxy($C_1$–$C_6$)alkoxy, mono- or di-($C_1$–$C_6$)alkylaryl ($C_1$–$C_6$)alkyl, mono- or di-($C_1$–$C_6$)alkoxyaryl($C_1$–$C_6$) alkyl, mono- or di-($C_1$–$C_6$)alkylaryl($C_1$–$C_6$)alkoxy, mono- or di-($C_1$–$C_6$)alkoxyaryl($C_1$–$C_6$)alkoxy, amino, mono($C_1$–$C_6$)alkylamino, di($C_1$–$C_6$)alkylamino, diarylamino, piperazino, N-($C_1$–$C_6$)alkylpiperazino, N-arylpiperazino, aziridino, indolino, piperidino, morpholino, thiomorpholino, tetrahydroquinolino, tetrahydroisoquinolino, pyrrolidyl, $C_1$–$C_6$ alkyl, $C_1$–$C_6$ chloroalkyl, $C_1$–$C_6$ fluoroalkyl, $C_1$–$C_6$ alkoxy, mono ($C_1$–$C_6$)alkoxy($C_1$–$C_4$)alkyl, acryloxy, methacryloxy, bromo, chloro or fluoro, said aryl being chosen from phenyl or naphthyl;
(iv) an unsubstituted or mono-substituted group chosen from pyrazolyl, imidazolyl, pyrazolinyl, imidazolinyl, pyrrolinyl, phenothiazinyl, phenoxazinyl, phenazinyl or acridinyl, each of said substituents being independently chosen from $C_1$–$C_6$ alkyl, $C_1$–$C_6$ alkoxy, phenyl, fluoro, chloro or bromo;

(v) a monosubstituted phenyl, said phenyl having a substituent located at the para position being a linking group, —($CH_2$)$_r$— or —O—($CH_2$)$_r$—, connected to an aryl group which is a member of another photochromic material, and r being chosen from the integer 1, 2, 3, 4, 5 or 6;
(vi) a group represented by one of the following graphic formulae:

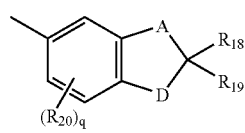 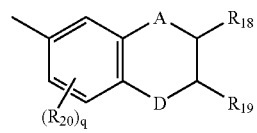

wherein A being independently chosen in each formula from methylene or oxygen and D being independently chosen in each formula from oxygen or substituted nitrogen, provided that when D is substituted nitrogen, A is methylene; said nitrogen substituents being chosen from hydrogen, $C_1$–$C_6$ alkyl, or $C_2$–$C_6$ acyl; each $R_{20}$ being independently chosen for each occurrence in each formula from $C_1$–$C_6$ alkyl, $C_1$–$C_6$ alkoxy, hydroxy, chloro or fluoro; $R_{18}$ and $R_{19}$ each being independently chosen in each formula from hydrogen or $C_1$–$C_6$ alkyl; and q being chosen from the integer 0, 1 or 2;

(vii) $C_1$–$C_6$ alkyl, $C_1$–$C_6$ chloroalkyl, $C_1$–$C_6$ fluoroalkyl, $C_1$–$C_6$ alkoxy($C_1$–$C_4$)alkyl, $C_3$–$C_6$ cycloalkyl, mono ($C_1$–$C_6$)alkoxy($C_3$–$C_6$)cycloalkyl, mono($C_1$–$C_6$)alkyl ($C_3$–$C_6$)-cycloalkyl, chloro($C_3$–$C_6$)cycloalkyl, fluoro ($C_3$–$C_6$)cyclo-alkyl or $C_4$–$C_{12}$ bicycloalkyl;
(viii) a group represented by the following graphic formula:

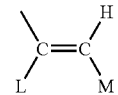

wherein L being chosen from hydrogen or $C_1$–$C_4$ alkyl and M being chosen from an unsubstituted, mono-, or di-substituted group chosen from naphthyl, phenyl, furanyl, or thienyl; each of said group substituents being independently chosen from $C_1$–$C_4$ alkyl, $C_1$–$C_4$ alkoxy, fluoro, or chloro; or
(ix) B and B' taken together form fluoren-9-ylidene, mono-, or di-substituted fluoren-9-ylidene or a group being independently chosen from saturated $C_3$–$C_{12}$ spiro-monocyclic hydrocarbon rings, saturated $C_7$–$C_{12}$ spiro-bicyclic hydrocarbon rings or saturated $C_7$–$C_{12}$ spiro-tricyclic hydrocarbon rings; each of said fluoren-9-ylidene substituents being independently chosen from $C_1$–$C_4$ alkyl, $C_1$–$C_4$ alkoxy, fluoro or chloro.

In one non-limiting embodiment, when the T group is a substituent on the photochromic materials as hereinbefore in (d) (i), polymerization of the photochromic polymerizable compounds can occur by mechanisms described in the definition of "polymerization" in *Hawley's Condensed Chemical Dictionary*, Thirteenth Edition, 1997, John Wiley & Sons, pages 901–902. Those mechanisms include by "addition", in which free radicals are the initiating agents that react with the double bond of the monomer by adding to it on one side at the same time producing a new free electron on the other side, by "condensation", involving the splitting out of water molecules by two reacting monomers and by so-called "oxidative coupling". Non-limiting examples of the polymerizable groups are hydroxy, (meth)acryloxy, 2-(methacryloxy)ethylcarbamyl, or epoxy, e.g., oxiranylmethyl. When there are 2 or more polymerizable groups on the naphthopyran, they may be the same or different.

The group, $—(OC_2H_4)_x—$, in the group T formulae, can represent poly(ethylene oxide); $—(OC_3H_6)_y—$, can represent poly(propylene oxide); and, $(OC_4H_8)_z—$, can represent poly(butylene oxide). When used in combination, the poly(ethylene oxide), poly(propylene oxide) and poly(butylene oxide) groups of T can be in a random or block order within the T moiety. The letters x, y and z are each a number between 0 and 50 and the sum of x, y and z is between 2 and 50. The sum of x, y and z can be any number that falls within the range of 2 to 50, e.g., 2, 3, 4 . . . 50. This sum can also range from any lower number to any higher number within the range of 2 to 50, e.g., 6 to 50, 31 to 50. The numbers for x, y, and z are average values and can be partial numbers, e.g., 9.5.

In another non-limiting embodiment, the naphthopyran is represented by graphic formula II wherein:
(a) $R_{12}$ is hydrogen;
(b) $R_{13}$ is hydrogen or the group, $—C(O)J$, J being $—OR_{15}$ or $—N(R_{10})R_{11}$, wherein $R_{15}$ is $C_1–C_6$ alkyl, phenyl$(C_1–C_3)$alkyl, or $C_1–C_6$ alkoxy$(C_2–C_4)$alkyl;
(c) $R_{14}$ is hydrogen, $C_1–C_6$ alkyl, phenyl$(C_1–C_3)$alkyl, $C_1–C_6$ alkoxy$(C_2–C_4)$alkyl, $C_5–C_7$ cycloalkyl, or the group, $—C(O)V$; wherein V is $C_1–C_6$ alkyl, $C_1–C_6$ alkoxy or $C_1–C_6$ alkylamino; and
(d) B and B' are each independently chosen from:
(i) an unsubstituted, mono-, di-, or tri-substituted phenyl group;
(ii) a mono-substituted heteroaromatic group chosen from benzofuran-2-yl, benzothien-3-yl, dibenzofuranyl, or carbazoyl; each of said phenyl and heteroaromatic substituents in (i) and (ii) being independently chosen from $—C(O)U$, wherein U being $C_1–C_6$ alkyl, $C_1–C_6$ alkoxy, mono-$(C_1–C_6)$alkylamino, di-$(C_1–C_6)$alkylamino, morpholino, or piperidino; or amino, mono$(C_1–C_6)$alkylamino, di$(C_1–C_6)$alkylamino, piperidino, morpholino or fluoro;
(iii) an unsubstituted or mono-substituted phenothiazinyl, said substituents being $C_1–C_6$ alkyl or $C_1–C_6$ alkoxy;
(iv) a monosubstituted phenyl, said phenyl having a substituent located at the para position being a linking group, $—O—(CH_2)_r—$, connected to an aryl group which is a member of another photochromic material, and r being chosen from the integer 3 or 6;
(v) a group represented by one of the following graphic formulae:

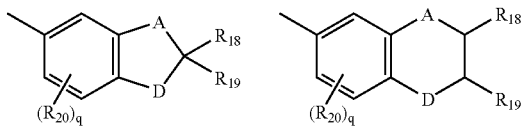

wherein A being independently chosen in each formula from methylene or oxygen and D being independently chosen in each formula from oxygen or substituted nitrogen, provided that when D is substituted nitrogen, A is methylene; said nitrogen substituents being $C_1–C_6$ alkyl; each $R_{20}$ being independently chosen for each occurrence in each formula from $C_1–C_6$ alkyl or $C_1–C_6$ alkoxy; $R_{18}$ and $R_{19}$ each being independently chosen in each formula from hydrogen or $C_1–C_6$ alkyl; and q being chosen from the integer 0, 1 or 2;
(vi) $C_1–C_6$ alkyl, $C_3–C_6$ cycloalkyl, or $C_4–C_{12}$ bicycloalkyl;
(vii) a group represented by the following graphic formula:

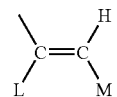

wherein L being hydrogen and M being an unsubstituted, mono-, or di-substituted phenyl; each of said group substituents being independently chosen from $C_1–C_4$ alkoxy or fluoro; or
(viii) B and B' taken together form fluoren-9-ylidene, mono-, or di-substituted fluoren-9-ylidene or a saturated $C_7–C_{12}$ spiro-bicyclic hydrocarbon rings; each of said fluoren-9-ylidene substituents being fluoro.

In further non-limiting embodiment, the naphthopyran represented by graphic formula II is chosen from:
(a) 3,3-diphenyl-8-hydroxy-9-carbopropoxy-3H-naphtho[2,1-b]pyran;
(b) 3-(2-fluorophenyl)-3-(4-methoxyphenyl)-8-hydroxy-9-carbopropoxy-3H-naphtho[2,1-b]pyran;
(c) 3-(2-fluorophenyl)-3-(4-methoxyphenyl)-8-hydroxy-9-carbomethoxy-3H-naphtho[2,1-b]pyran;
(d) 3-(2,4-dimethoxyphenyl)-3-(4-methoxyphenyl)-8-hydroxy-9-carbomethoxy-3H-naphtho[2,1-b]pyran;
(e) 3,3-diphenyl-8-methoxy-9-carbophenoxy-3H-naphtho[2,1-b]pyran;
(f) 3-(2-fluorophenyl)-3-(4-methoxyphenyl)-8-methoxy-9-carbophenoxy-3H-naphtho[2,1-b]pyran;
(g) 3-(2-fluorophenyl)-3-(4-methoxyphenyl)-8-methoxy-9-carbomethoxy-3H-naphtho[2,1-b]pyran;
(h) 3-(2,4-dimethoxyphenyl)-3-(4-methoxyphenyl)-8-acetoxy-9-carbomethoxy-3H-naphtho[2,1-b]pyran;
(i) 3,3-diphenyl-7-methyl-8-methoxy-3H-naphtho[2,1-b]pyran;
(j) 3-(2-methoxy,4-acryloxyphenyl)-3-(4-methacryloxyphenyl)-8-benzyloxy-9-(carbo-1-indolinyl)-3H-naphtho[2,1-b]pyran;
(k) 3-(2,4,6-trifluorophenyl)-3-(2,4,6-trimethoxy-1-naphthyl)-8-acetyl-9-carboniloyl-3H-naphtho[2,1-b]pyran;
(l) 3-(2-fluorophenyl)-3-(3-methoxy-2-thienyl)-7-h-pentyl-8-benzoyloxy-3H-naphtho[2,1-b]pyran;
(m) 3,3-spiroadamantylene-8-acetoxy-9-carbomethoxy-3H-naphtho[2,1-b]pyran;
(n) 3-(4-methoxyphenyl)-3-(2-methyl-2,3-dihydrobenzofur-5-yl)-8-methoxy-9-carbomethoxy-3H-naphtho[2,1-b]pyran;
(o) 3-(4-methoxyphenyl)-3-(2-phenyl-1-methylvinyl)-8-acetoxy-9-carbomethoxy-3H-naphtho[2,1-b]pyran;
(p) 3-(4-methoxyphenyl)-3-(9-ethylcarbozol-2-yl)-8-methoxy-9-carbomethoxy-3H-naphtho[2,1-b]pyran;
(q) 3,3-spirofluoren-9-ylidene-8-methoxy-9-carbomethoxy-3H-naphtho[2,1-b]pyran;
(r) 3,3-diphenyl-8-morpholino-9-carbomethoxy-3H-naphtho[2,1-b]pyran; or
(s) mixtures thereof.

The materials represented by graphic formula II can be produced by methods known to those skilled in the art, for example, as disclosed in U.S. Pat. Nos. 5,466,398, 5,578,252 and 5,637,262.

In one non-limiting embodiment, a photochromic material is chosen from a naphthopyran represented by the following graphic formula III:

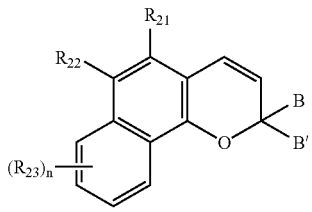

III wherein, (a) $R_{21}$ is the group, —C(O)W or $CH_2Q$, described hereinbefore in (d) for the material represented by graphic formula I;

(b) $R_{22}$ and each $R_{23}$ are independently chosen for each occurrence from hydroxy, $NH_2$ or N(R)H; wherein R is $C_1$–$C_6$ alkyl or aryl and n is chosen from the integers 0, 1, 2, or 3; and (c) B and B' are each independently chosen from the groups described hereinbefore in (d) for the material represented by graphic formula II.

In another non-limiting embodiment, the naphthopyran is represented by graphic formula III wherein:

(a) $R_{21}$ is the group, —C(O)W or $CH_2Q$, described hereinbefore in (d) for the material represented by graphic formula I;

(b) $R_{22}$ and each $R_{23}$ are independently chosen for each occurrence from hydroxy, $NH_2$ or N(R)H; wherein R is $C_1$–$C_3$ alkyl or phenyl and n is chosen from the integers 0, 1 or 2; and (c) B and B' are each independently chosen from the groups described hereinbefore in (d) for the material represented by graphic formula II.

In further non-limiting embodiment, the naphthopyran represented by graphic formula III is chosen from:
(a) 2,2-di(4-methoxyphenyl)-5-methoxycarbonyl-6-hydroxy-2H-naphtho[1,2-b]pyran;
(b) 2,2-di(4-methoxyphenyl)-5-methoxycarbonyl-6-amino-2H-naphtho[1,2,-b]pyran;
(c) 2,2-di(4-methoxyphenyl)-5-methoxycarbonyl-6-propylamino-2H-naphtho[1,2-b]pyran;
(d) 2-(4-methoxyphenyl)-2-t-butyl-5-methoxycarbonyl-6-hydroxy-2H-naphtho[1,2-b]pyran;
(e) 2-(4-methoxyphenyl)-2-phenyl-5-methoxycarbonyl-6-amino-2H-naphtho[1,2-b]pyran;
(f) 2,2-di(4-methylphenyl)-5-methoxycarbonyl-6-methylamino-2H-naphtho[1,2-b]pyran;
(g) 2,2-diphenyl-5-methoxycarbonyl-6-hydroxy-2H-naphtho[1,2-b]pyran;
(h) 2,2-di(4-methoxyphenyl)-5-methoxycarbonyl-6-phenylamino-2H-naphtho[1,2-b]pyran;
(i) 2,2-di(4-methoxyphenyl)-5-methoxycarbonyl-6-hydroxy-9-methoxy-2H-naphtho[1,2-b]pyran;
(j) 2,2-diphenyl-5-methoxycarbonyl-6-phenylamino-2H-naphtho[1,2-b]pyran;
(k) 2,2-di(3-trifluoromethylphenyl)-5-methoxycarbonyl-6-hydroxy-2H-naphtho[1,2-b]pyran;
(l) 2-(4-methoxyphenyl)-2-(2-methyl,2,3-dihydrobenzofur-5-yl)-5-methoxycarbonyl-6-amino-2H-naphtho[1,2-b]pyran;
(m) 2,2'-spiroadamantylene-5-methoxycarbonyl-6-methoxy-2H-naphtho[1,2-b]pyran; or
(n) mixtures thereof.

The materials represented by graphic formula III can be produced by methods known to those skilled in the art, for example, as disclosed in U.S. Pat. Nos. 5,458,814; 5,573,712; 5,650,098; and 5,651,923.

In one non-limiting embodiment, a photochromic material is chosen from a naphthopyran represented by the following graphic formula IV:

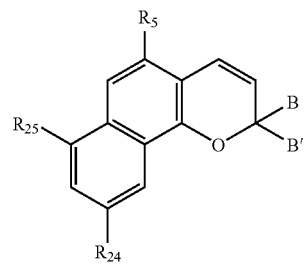

IV wherein, (a) $R_5$ is the same group described hereinbefore in (d) for the material represented by graphic formula I;

(b) $R_{24}$ and $R_{25}$ are each chosen from hydrogen or an amino group defined hereinafter, provided that $R_{24}$ and $R_{25}$ are not both hydrogen; said amino group being:

(i) —N($R_{16}$)$R_{17}$, $R_{16}$ and $R_{17}$ each being independently chosen from hydrogen, $C_1$–$C_8$ alkyl, aryl, furanyl, benzofuran-2-yl, benzofuran-3-yl, thienyl, benzothien-2-yl, benzothien-3-yl, dibenzofuranyl, dibenzothienyl, benzopyridyl, fluorenyl, $C_1$–$C_8$ alkylaryl, $C_3$–$C_{20}$ cycloalkyl, $C_4$–$C_{20}$ bicycloalkyl, $C_5$–$C_{20}$ tricycloalkyl or $C_1$–$C_{20}$ alkoxyalkyl and said aryl group being phenyl or naphthyl;

(ii) a nitrogen containing ring represented by the following graphic formula:

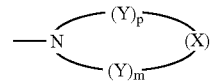

wherein each Y being independently chosen for each occurrence from —$CH_2$—, —CH($R_{26}$)—, —C($R_{26}$)($R_{26}$)—, —CH(aryl)-, —C(aryl)$_2$— or —C($R_{26}$) (aryl)-; X being —Y—, —O—, —S—, —S(O)—, —S(O$_2$)—, —NH—, —N($R_{26}$)— or —N(aryl)-; $R_{26}$ being $C_1$–$C_6$ alkyl; said aryl group being phenyl or naphthyl, m being chosen from the integer 1, 2 or 3 and p being chosen from the integer 0, 1, 2 or 3; provided that when p is 0, X is Y;

(iii) a group represented by one of the following graphic formulae:

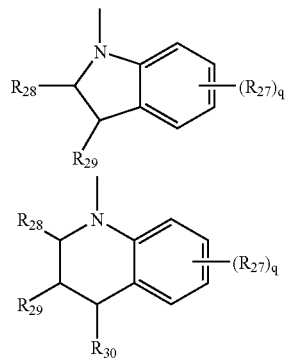

wherein each $R_{28}$, $R_{29}$ and $R_{30}$ being chosen independently for each occurrence in each formula from hydrogen, $C_1$–$C_5$ alkyl, phenyl or naphthyl; or the groups $R_{28}$ and $R_{29}$ together form a ring of 5 to 8 carbon atoms; $R_{27}$ being chosen independently for each occurrence from $C_1$–$C_6$ alkyl, $C_1$–$C_6$ alkoxy, fluoro or chloro and q being chosen from the integer 0, 1 or 2;

(iv) unsubstituted, mono- or di-substituted $C_4$–$C_{18}$ spirobicyclic amine; or (v) unsubstituted, mono- or di-substituted $C_4$–$C_{18}$ spirotricyclic amine; said substituents for (iv) and (v) being independently chosen for each occurrence from aryl, $C_1$–$C_6$ alkyl, $C_{1-6}$ alkoxy or phenyl($C_1$–$C_6$)alkyl; and (c) B and B' are each independently chosen from the groups described hereinbefore in (d) for the material represented by graphic formula II.

In another non-limiting embodiment, the naphthopyran represented by graphic formula IV wherein:

(a) $R_5$ is chosen from the groups described hereinbefore in (d) for the material represented by graphic formula I;

(b) $R_{24}$ and $R_{25}$ are each chosen from hydrogen or an amino group defined hereinafter, provided that $R_{24}$ and $R_{25}$ are not both hydrogen; said amino group being:

(i) —N($R_{16}$)$R_{17}$, $R_{16}$ and $R_{17}$ each being independently chosen from $C_1$–$C_8$ alkyl, aryl, or $C_3$–$C_{20}$ cycloalkyl; and said aryl group being phenyl or naphthyl;

(ii) a nitrogen containing ring represented by the following graphic formula:

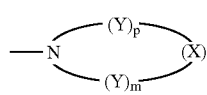

wherein each Y being independently chosen for each occurrence from —CH$_2$—, ; X being —Y—, —O—, —S—, or —N($R_{26}$)—; $R_{26}$ being $C_1$–$C_6$ alkyl; said aryl group being phenyl or naphthyl, m being chosen from the integer 1, 2 or 3 and p being chosen from the integer 0, 1, 2 or 3; provided that when p is 0, X is Y; or (iii) a group represented by one of the following graphic formulae:

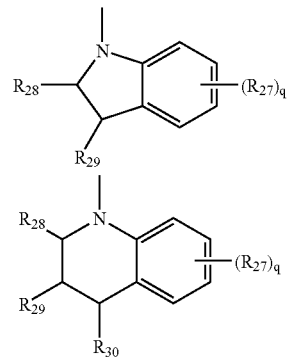

wherein each $R_{28}$, $R_{29}$ and $R_{30}$ being chosen independently for each occurrence in each formula from hydrogen; $R_{27}$ being chosen independently for each occurrence from $C_1$–$C_6$ alkyl, and q being chosen from the integer 0, 1 or 2; and (c) B and B' are each independently chosen from the groups described hereinbefore in (d) for the material represented by graphic formula II.

In a further non-limiting embodiment, the naphthopyran represented by graphic formula IV is chosen from:
(a) 2-phenyl-2-(4-morpholinophenyl)-5-carbomethoxy-9-dimethylamino-2H-naphtho[1,2-b]pyran;
(b) 2,2-di(4-methoxyphenyl)-5-methoxymethyl-9-morpholino-2H-naphtho[1,2-b]pyran;
(c) 2-(4-methoxyphenyl)-2-(4-piperidinophenyl)-5-carbomethoxy-9-dimethylamino-2H-naphtho[1,2-b]pyran; or
(d) mixtures thereof.

The materials represented by graphic formula IV can be produced by methods known to those skilled in the art, for example, as disclosed in U.S. Pat. Nos. 6,248,264 and 6,348,604.

In one non-limiting embodiment, a photochromic material is chosen from a phenanthropyran represented by one of the following graphic formula VA or VB:

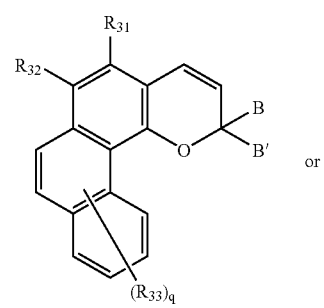

VA or

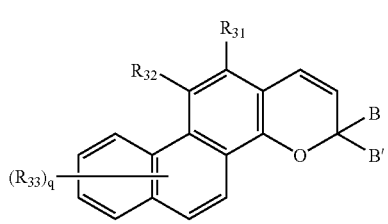

VB wherein, (a) $R_{31}$ is the group $R_5$, described hereinbefore in (d) for the material represented by graphic formula I;

(b) $R_{32}$ is hydrogen, $C_1$–$C_6$ alkyl, $C_1$–$C_6$ alkoxy, $C_3$–$C_7$ cycloalkyl, pyridyl, phenyl, mono-substituted or di-substituted phenyl, said phenyl substituents being $C_1$–$C_6$ alkyl, $C_1$–$C_6$ alkoxy, hydroxy, amino, chloro, or fluoro;

(c) each $R_{33}$ is independently chosen for each occurrence from chloro, fluoro, amino, $C_1$–$C_6$ monoalkylamino, —N($R_{10}$)$R_{11}$, as described hereinbefore in (d) for the material represented by graphic formula I, phenyl, $C_1$–$C_6$ alkyl, or —O$R_{34}$, wherein $R_{34}$ is hydrogen, $C_1$–$C_6$ alkyl, allyl, or acetyl, and q is the integer 0, 1, or 2; and (d) B and B' are each independently chosen from the groups described hereinbefore in (d) for the material represented by graphic formula II.

In another non-limiting embodiment, the phenanthropyran is represented by graphic formula VA or VB wherein:

(a) $R_{31}$ is the group, $R_5$ described hereinbefore in (d) for the material represented by graphic formula I;

(b) $R_{32}$ is hydrogen or $C_1$–$C_6$ alkyl;

(c) each $R_{33}$ is independently chosen for each occurrence from —N($R_{10}$)$R_{11}$, which was described hereinbefore in (d) for the material represented by graphic formula I, $C_1$–$C_6$ alkyl, or —O$R_{34}$, wherein $R_{34}$ is $C_1$–$C_6$ alkyl, and q is the integer 0, 1, or 2; and (d) B and B' are each independently chosen from the groups described hereinbefore in (d) for the material represented by graphic formula II.

In a further non-limiting embodiment, the phenanthropyran represented by graphic formula VA or VB is chosen from:

(a) 3,3-diphenyl-12-methoxycarbonyl-11-methyl-3H-phenanthro[1,2-b]pyran;

(b) 2,2-diphenyl-5-methoxycarbonyl-6-methyl-2H-phenanthro[4,3-b]pyran;

(c) 2-(4-methoxyphenyl)-2-phenyl-5-methoxycarbonyl-6-methyl-2H-phenanthro[4,3-b]pyran;

(d) 3-(2-fluorophenyl)-3-(4-methoxyphenyl)-6-methoxy-12-methoxycarbonyl-3H-phenanthro[1,2-b]pyran;

(e) spiro[3H-6-methoxy-12-methoxycarbonylphenanthro[1,2-b]pyran-3-9'-fluorene];

(f) 2,2-di(4-methoxyphenyl)-10-methoxy-5-methoxycarbonyl-6-methyl-2H-phenanthro[4,3-b]pyran;

(g) 3-(2,3-dihydrobenzofur-5-yl)-3-(4-methoxyphenyl)-6-methoxy-12-methoxycarbonyl-11-methyl-3H-phenanthro[1,2-b]pyran;

(h) 3,3-diphenyl-6-methoxy-12-methoxycarbonyl-11-phenyl-3H-phenanthro[1,2-b]pyran;

(i) 3-(4-methoxyphenyl)-3-(2-methyl-2,3-dihydrobenzofur-5-yl)-6-methoxy-12-methoxycarbonyl-11-phenyl-3H-phenanthro[1,2-b]pyran;

(j) 3-(4-methoxyphenyl)-3-(2-methyl-2,3-dihydrobenzofur-5-yl)-6-methoxy-12-hydroxymethyl-11-phenyl-3H-phenanthro[1,2-b]pyran;

(k) 2,2-diphenyl-5-N,N-dimethylaminocarbonyl-2H-phenanthro[4,3-b]pyran; or (l) mixtures thereof.

The materials represented by graphic formula V can be produced by methods known to those skilled in the art, for example, as disclosed in U.S. Pat. No. 5,514,817.

In one non-limiting embodiment, a photochromic material is chosen from a fluoranthenopyran represented by the following graphic formula VI:

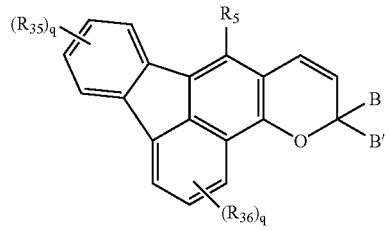

wherein, (a) $R_{35}$ and $R_{36}$ are each independently chosen for each occurrence from hydroxy, aryl, mono($C_1$–$C_6$)alkoxyaryl, di($C_1$–$C_6$)alkoxyaryl, mono($C_1$–$C_6$)alkylaryl, di($C_1$–$C_6$)alkylaryl, bromoaryl, chloroaryl, fluoroaryl, $C_3$–$C_7$ cycloalkylaryl, $C_3$–$C_7$ cycloalkyl, $C_3$–$C_7$ cycloalkyloxy, $C_3$–$C_7$ cycloalkyloxy($C_1$–$C_6$)alkyl, $C_3$–$C_7$ cycloalkyloxy($C_1$–$C_6$)alkoxy, aryl($C_1$–$C_6$)alkyl, aryl($C_1$–$C_6$)alkoxy, aryloxy, aryloxy($C_1$–$C_6$)alkyl, aryloxy($C_1$–$C_6$)alkoxy, mono- or di($C_1$–$C_6$)alkylaryl($C_1$–$C_6$)alkyl, mono- or di($C_1$–$C_6$) alkoxyaryl($C_1$–$C_6$)alkyl, mono- or di($C_1$–$C_6$)alkylaryl ($C_1$–$C_6$)alkoxy, mono- or di($C_1$–$C_6$)alkoxyaryl($C_1$–$C_6$) alkoxy, $C_1$–$C_6$ alkyl, $C_1$–$C_6$ bromoalkyl, $C_1$–$C_6$ chloroalkyl, $C_1$–$C_6$ fluoroalkyl, $C_1$–$C_6$ alkoxy, mono($C_1$–$C_6$)alkoxy ($C_1$–$C_4$)alkyl, acryloxy, methacryloxy, bromo, chloro, fluoro, amino, mono($C_1$–$C_6$)alkylamino, di($C_1$–$C_6$)alkylamino, phenylamino, mono- or di-($C_1$–$C_6$)alkyl substituted phenylamino or mono- or di-($C_1$–$C_6$)alkoxy substituted phenylamino, and q is the integer 0, 1 or 2;

(b) $R_5$ is chosen from the group described hereinbefore in (d) for the material represented by graphic formula I; and (c) B and B' are each independently chosen from the groups described hereinbefore in (d) for the material represented by graphic formula II.

In another non-limiting embodiment, the fluoranthenopyran is represented by graphic formula VI wherein:

(a) $R_{35}$ and $R_{36}$ are each independently chosen for each occurrence from $C_1$–$C_6$ alkyl, $C_1$–$C_6$ alkoxy, fluoro, amino, mono($C_1$–$C_6$)alkylamino, di($C_1$–$C_6$)alkylamino, phenylamino, mono- or di-($C_1$–$C_6$)alkyl substituted phenylamino or mono- or di-($C_1$–$C_6$)alkoxy substituted phenylamino, and q is the integer 0, 1 or 2;

(b) $R_5$ is chosen from the group described hereinbefore in (d) for the material represented by graphic formula I; and (c) B and B' are each independently chosen from the groups described hereinbefore in (d) for the material represented by graphic formula II.

In a further non-limiting embodiment, the fluoranthenopyran represented by graphic formula VI is chosen from:

(a) 5,5-bis(4-methoxyphenyl)-8-ethoxycarbonyl-5H-fluorantheno[3,2-b]pyran;

(b) 5-(4-methoxyphenyl)-5-(4-morpholinophenyl)-8-ethoxycarbonyl-5H-fluorantheno[3,2-b]pyran;

(c) 5,5-diphenyl-8-ethoxycarbonyl-5H-fluorantheno[3,2-b]pyran;

(d) 5,5-bis(4-methoxyphenyl)-8-methylol-5H-fluorantheno[3,2-b]pyran;

(e) 5,5-bis(4-methoxyphenyl)-2-methoxy-8-methoxycarbonyl-5H-fluorantheno[3,2-b]pyran; or (f) mixtures thereof.

The materials represented by graphic formula VI can be produced by methods known to those skilled in the art, for example, as disclosed in U.S. Pat. No. 5,891,368.

In one non-limiting embodiment, a photochromic material is chosen from a naphthopyran represented by the following graphic formula VII:

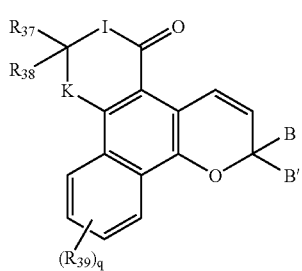

wherein, (a) $R_{37}$ and $R_{38}$ together form an oxo group or $R_{37}$ and $R_{38}$ each are independently chosen for each occurrence from hydrogen, $C_1$–$C_6$ alkyl, $C_3$–$C_7$ cycloalkyl, allyl, phenyl, mono- or di-substituted phenyl, benzyl, mono-substituted benzyl, naphthyl, mono- or di-substituted naphthyl, $C_4$–$C_{12}$ bicycloalkyl, linear or branched $C_3$–$C_{12}$ alkenyl, $C_1$–$C_6$ alkoxy carbonyl($C_1$–$C_6$)alkyl, methacryloxy($C_1$–$C_6$)alkyl, acryloxy($C_1$–$C_6$)alkyl, $C_1$–$C_4$ acyloxy($C_1$–$C_6$)alkyl, $C_1$–$C_6$ alkoxy($C_1$–$C_6$)alkyl or the unsubstituted, mono- or di-substituted heteroaromatic groups pyridyl, furanyl, benzofuran-2-yl, benzyfuran-3-yl, thienyl, benzothien-2-yl, benzothien-3-yl, dibenzofuranyl, dibenzothienyl, carbazolyl, benzopyridyl and indolyl, each of said phenyl, benzyl, naphthyl and heteroaromatic group substituents being $C_1$–$C_6$ alkyl, $C_1$–$C_6$ alkoxy, morpholino, di($C_1$–$C_6$)alkylamino, chloro or fluoro;

(b) $R_{39}$ is chosen from $C_1$–$C_6$ alkyl, $C_1$–$C_6$ alkoxy, chloro, fluoro, phenyl, mono- and di-substituted phenyl, benzyl or mono-substituted benzyl, $C_3$–$C_7$ cycloalkyl, aryloxy, di($C_1$–$C_6$)alkylamino, morpholino, thiomorpholino, piperidino, pyridyl, tetrahydroquinolino, isoquinolino, aziridino, diarylamino, N-($C_1$–$C_6$)alkyl piperizino or N-aryl piperizino, wherein the aryl groups are phenyl or naphthyl, each of said phenyl and benzyl substituents being $C_1$–$C_6$ alkyl, $C_1$–$C_6$ alkoxy, fluoro or chloro, and q is the integer 0, 1 or 2;

(c) I is oxygen or —N($R_{40}$)—, wherein $R_{40}$ is hydrogen $C_1$–$C_6$ alkyl, $C_3$–$C_7$ cycloalkyl, allyl, vinyl, $C_1$–$C_5$ acyl, phenyl, mono- and di-substituted phenyl, benzyl, mono-substituted benzyl, $C_1$–$C_4$ alkoxycarbonyl($C_1$–$C_6$)alkyl, methacryloxy($C_1$–$C_6$)alkyl, acryloyloxy($C_1$–$C_6$)alkyl, phenyl($C_1$–$C_6$)alkyl, naphthyl, $C_4$–$C_{12}$ bicycloalkyl, $C_2$–$C_4$ acyloxy or the unsubstituted or substituted heteroaromatic groups pyridyl, furanyl, benzofuran-2-yl, benzofuran-3-yl, thienyl, benzothien-2-yl, benzothien-3-yl, dibenzofuranyl, dibenzothienyl, carbazolyl, benzopyridyl or indolyl, each of said phenyl, benzyl and heteroaromatic group substituents being $C_1$–$C_6$ alkyl or $C_1$–$C_6$ alkoxy;

(d) K is oxygen, —N($R_{40}$)— or —C($R_{41}$)($R_{42}$)—, wherein $R_{41}$ and $R_{42}$ are each hydrogen, $C_1$–$C_6$ alkyl or $C_3$–$C_7$ cycloalkyl; and (e) B and B' are each independently chosen from the groups described hereinbefore in (d) for the material represented by graphic formula II.

In another non-limiting embodiment, the naphthopyran is represented by graphic formula VII wherein:

(a) $R_{37}$ and $R_{38}$ together form an oxo group or $R_{37}$ and $R_{38}$ each are independently chosen for each occurrence from hydrogen, $C_1$–$C_6$ alkyl, $C_3$–$C_7$ cycloalkyl, phenyl or methacryloxy($C_1$–$C_6$)alkyl;

(b) $R_{39}$ is chosen from $C_1$–$C_6$ alkyl, $C_1$–$C_6$ alkoxy, fluoro, or morpholino, and q is the integer 0, 1 or 2;

(c) I is oxygen or —N($R_{40}$)—, wherein $R_{40}$ is $C_1$–$C_6$ alkyl, $C_3$–$C_7$ cycloalkyl or phenyl;

(d) K is oxygen, —N($R_{40}$)— or —C($R_{41}$)($R_{42}$)—, wherein $R_{41}$ and $R_{42}$ are each hydrogen or $C_1$–$C_6$ alkyl; and (e) B and B' are each independently chosen from the groups described hereinbefore in (d) for the material represented by graphic formula II.

In a further non-limiting embodiment, the naphthopyran represented by graphic formula VII is chosen from:

a) 7,7-diphenyl-4-oxo-4H-7H-[1,3]dioxino[5',4':3,4]naphtho[1,2-b]pyran;

b) 7,7-di(4-methoxyphenyl)-4-oxo-4H-7H-[1,3]dioxino [5',4':3,4]naphtho[1,2-b]pyran;

c) 7-(4-methoxyphenyl)-7-phenyl-2-pentyl-4-oxo-4H-7H-[1,3]dioxino[5',4':3,4]naphtho[1,2-b]pyran;

d) 7,7-diphenyl-2-ethyl-4-oxo-4H-7H-[1,3]dioxino [5',4':3,4]naphtho[1,2-b]pyran;

e) 7,7-diphenyl-2-pentyl-4-oxo-4H-7H-[1,3]dioxino [5',4':3,4]naphtho[1,2-b]pyran;

f) 7,7-diphenyl-2-(2-methylpropyl)-4-oxo-4H-7H-[1,3]dioxino[5',4':3,4]naphtho[1,2-b]pyran;

g) 2,7,7-triphenyl-4-oxo-4H-7H-[1,3]dioxino [5',4':3,4] naphtho[1,2-b]pyran;

h) 7,7-diphenyl-2-(1-phenylethyl)-4-oxo-4H-7H-[1,3]dioxino[5',4':3,4]naphtho[1,2-b]pyran;

i) 3-methyl-7,7-diphenyl-2,4-dioxo-2,3,4,7-tetrahydro [1,3] oxazino[5',6':3,4]naphtho[1,2-b]pyran;

j) 3-(2-ethoxycarbonylethyl)-7,7-diphenyl-2,4-dioxo-2,3,4,7-tetrahydro[1,3]oxazino[5',6':3,4]naphtho[1,2-b]pyran;

k) 3-hexyl-7,7-diphenyl-2,4-dioxo-2,3,4,7-tetrahydro[1,3]oxazino[5',6':3,4]naphtho[1,2-b]pyran;

l) 3-(2-methacryloyloxyethyl)-7,7-diphenyl-2,4-dioxo-2,3,4,7-tetrahydro[1,3]oxazino[5',6':3,4]naphtho[1,2-b]pyran;

m) 2,2,7,7-tetraphenyl-4-oxo-2,3,4,7-tetrahydro-1H-pyrimidino[5',4':3,4]naphtho[1,2-b]pyran;

n) 2,2,7,7-tetraphenyl-4-oxo-2,3,4,7-tetrahydro-1H-[1,3]oxazino[5',4':3,4]naphtho[1,2-b]pyran;

o) 7,7-diphenyl-1,2,4,7-tetrahydro-2,2-dimethylpyrano[3',4':3,4]naphtho[1,2-b]pyran;

p) 7-phenyl-7-(4-morpholinophenyl)-2-pentyl-4-oxo-4H-7H-[1,3]dioxino[5',4':3,4]naphtho[1,2-b]pyran;

q) 7-(2-fluorophenyl)-7-(3-methyl-4-methoxyphenyl)-2-pentyl-4-oxo-4H-7H-[1,3]dioxino[5',4':3,4]naphtho[1,2-b]pyran;

r) 7-(4-methoxyphenyl)-7-(2,4-dimethoxyphenyl)-2-pentyl-4-oxo-4H-7H-[1,3]dioxino[5',4':3,4]naphtho[1,2-b]pyran;

s) 7-(4-morpholino-2-fluorophenyl)-7-(4-methoxyphenyl)-2-pentyl-4-oxo-4H-7H-[1,3]dioxino[5',4':3,4]naphtho[1,2-b]pyran;

t) 7-(2-fluoro-4-methoxyphenyl)-7-(4-morpholinophenyl)-2-pentyl-4-oxo-4H-7H-[1,3]dioxino[5',4':3,4]naphtho[1,2-b]pyran;

u) 7-(4-morpholino-2-fluorophenyl)-7-(3,4-dimethoxyphenyl)-2-pentyl-4-oxo-4H-7H-[1,3]dioxino[5',4':3,4]naphtho[1,2-b]pyran; or v) mixtures thereof.

The materials represented by graphic formula VII can be produced by methods known to those skilled in the art, for example, as disclosed in U.S. Pat. No. 6,022,497.

In one non-limiting embodiment, a photochromic material is chosen from a naphthopyran represented by the following graphic formula VIII:

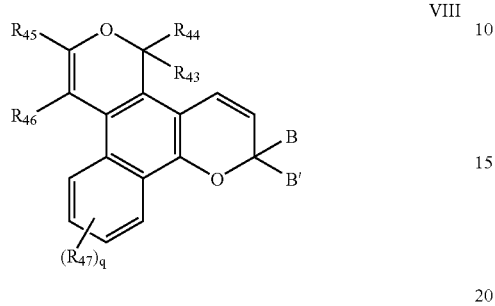

VIII wherein, (a) $R_{43}$ and $R_{44}$ together form an oxo group or $R_{43}$ and $R_{44}$ are both hydrogen, $C_1$–$C_6$ alkyl, $C_3$–$C_7$ cycloalkyl, allyl, phenyl, mono-substituted phenyl, benzyl or mono-substituted benzyl each of said phenyl and benzyl group substituents being $C_1$–$C_6$ alkyl or $C_1$–$C_6$ alkoxy;

(b) $R_{45}$ is hydrogen, $C_1$–$C_6$ alkyl, $C_3$–$C_7$ cycloalkyl, or the group, CH(B)B', wherein B and B' are each independently chosen from the groups described hereinbefore in (d) for the material represented by graphic formula II;

(c) $R_{46}$ is hydrogen, $C_1$–$C_6$ alkyl, or $C_3$–$C_7$ cycloalkyl;

(d) each $R_{47}$ is $C_1$–$C_6$ alkyl, $C_1$–$C_6$ alkoxy, chloro or fluoro, and q is the integer 0, 1, or 2; and (e) B and B' are each independently chosen from the groups described hereinbefore in (d) for the material represented by graphic formula II.

In another non-limiting embodiment, the naphthopyran is represented by graphic formula VIII wherein:

(a) $R_{43}$ and $R_{44}$ together form an oxo group or $R_{43}$ and $R_{44}$ are both hydrogen, $C_1$–$C_6$ alkyl, $C_3$–$C_7$ cycloalkyl or phenyl;

(b) $R_{45}$ is hydrogen or $C_1$–$C_6$ alkyl;

(c) $R_{46}$ is hydrogen or $C_1$–$C_6$ alkyl, $C_3$–$C_7$ cycloalkyl;

(d) each $R_{47}$ is $C_1$–$C_6$ alkyl, $C_1$–$C_6$ alkoxy or fluoro, and q is the integer 0, 1 or 2; and (e) B and B' are each independently chosen from the groups described hereinbefore in (d) for the material represented by graphic formula II.

In a further non-limiting embodiment, the naphthopyran represented by graphic formula VIII is chosen from:

(a) 7,7-diphenyl-4-oxo-4H-7H-[1,3]dioxino[5',4':3,4]naphtho[1,2-b]pyran;

2-(4-methoxyphenyl)-2-(2,4-dimethoxy-phenyl)-7-diphenylmethyl-10-methyl-5-oxo-2H-5H-pyrano[3',4':3,4]naphtho[1,2-b]pyran.

The materials represented by graphic formula VIII can be produced by methods known to those skilled in the art, for example, as disclosed in U.S. Pat. No. 6,106,744.

In one non-limiting embodiment, a photochromic material is chosen from a naphthopyran represented by the following graphic formulae IXA, IXB, IXC, IXD, IXE, IXF, IXG or IXH:

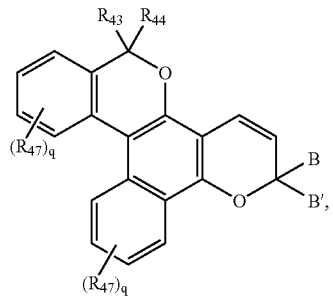

IXA

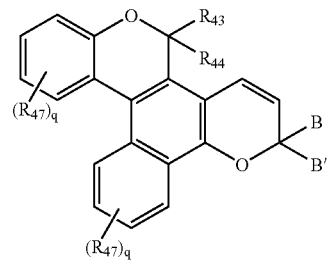

IXB

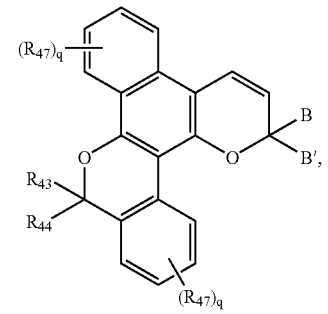

IXC

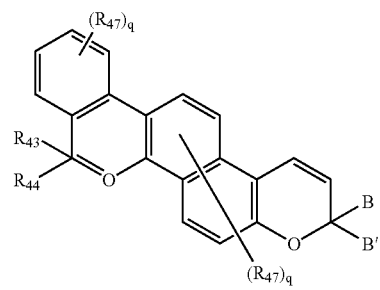

IXD

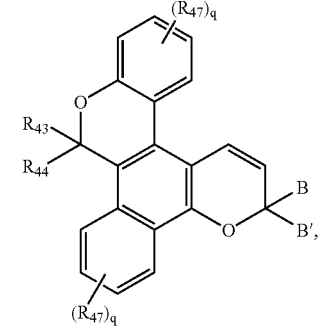

IXE

-continued

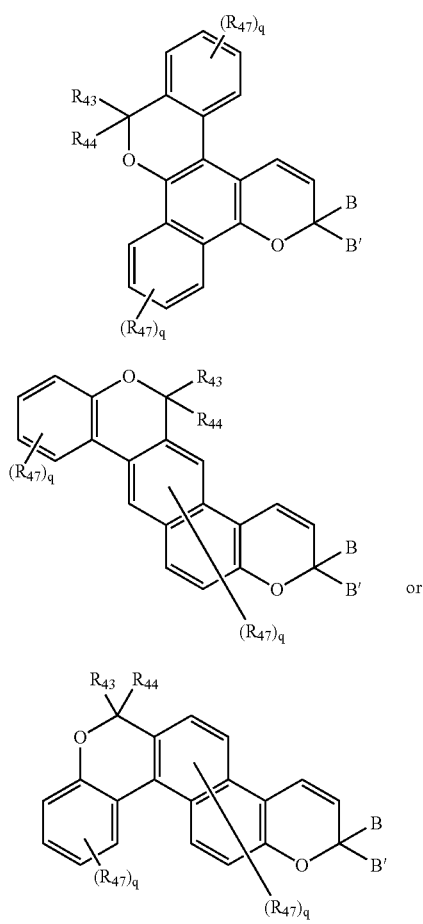

wherein, (a) $R_{43}$ and $R_{44}$ are the same groups described hereinbefore in (a) for the represented by graphic formula VIII;

(b) each $R_{47}$ and q are the same as described hereinbefore in (d) for the material represented by graphic formula VIII; and (c) B and B' are each independently chosen from the groups described hereinbefore in (d) for the material represented by graphic formula II.

In another non-limiting embodiment, the naphthopyran is represented by graphic formulae IXA, IXB, IXC, IXD, IXE, IXF, IXG or IXH wherein:

(a) $R_{43}$ and $R_{44}$ are the same groups described hereinbefore in (a) for the material represented by graphic formula VIII;

(b) each $R_{47}$ and q are the same as described hereinbefore in (d) for the material represented by graphic formula VIII; and (c) B and B' are each independently chosen from the groups described hereinbefore in (d) for the material represented by graphic formula II.

In a further non-limiting embodiment, the naphthopyran represented by graphic formula IXA, IXB, IXC or IXD is chosen from:

a) 2,2-bis(4-methoxyphenyl)-10-oxo-2,10-dihydro[2]benzopyrano[4',3':3,4]naphtho(2,1-b)pyran;

b) 6,6-bis(4-methoxyphenyl)-10-oxo-6,10-dihydro[2]benzopyrano[3',4':3,4]naphtho(1,2-b)pyran;

c) 6,6-bis(4-methoxyphenyl)-6,10-dihydro[2]benzopyrano-[3',4':3,4]naphtho(1,2-b)pyran;

d) 2-(4-methoxyphenyl)-2-(4-morpholinophenyl)-10-oxo-2,10-dihydro[2]benzopyrano[4',3':3,4]naphtho(2,1-b)pyran;

e) 6-(4-methoxyphenyl)-6-(4-morpholinophenyl)-10-oxo-6,10-dihydro[2]benzopyrano[3',4':3,4]naphtho(1,2-b)pyran;

f) 10,10-dimethyl-6-(4-methoxyphenyl)-6-(4-morpholinophenyl)-6,10-dihydro[2]benzopyrano[3',4':3,4]-naphtho (1,2-b) pyran;

g) 2-(4-morpholinophenyl)-2-phenyl-10-oxo-2,10-dihydro-[2]benzopyrano[4',3':3,4]naphtho(2,1-b)pyran;

h) 6-(4-morpholinophenyl)-6-phenyl-10-oxo-6,10-dihydro [2]benzopyrano[3',4':3,4]naphtho(1,2-b)pyran;

i) 2,2-bis(4-methoxyphenyl)-12,13-dimethoxy-10-oxo-2,10-dihydro[2]benzopyrano[4',3':3,4]naphtho(2,1-b)pyran;

j) 6,6-bis(4-methoxyphenyl)-12,13-dimethoxy-10-oxo-6,10-dihydro[2]benzopyrano[3',4':3,4]naphtho(1,2-b)pyran;

k) 6-(4-methoxyphenyl)-6-phenyl-12,13-dimethoxy-10-oxo-6,10-dihydro[2]benzopyrano[3',4':3,4]naphtho(1,2-b)-pyran;

l) 2-(4-methoxyphenyl)-2-phenyl-12,13-dimethoxy-10-oxo-2,10-dihydro[2]benzopyrano[4',3':3,4]naphtho(2,1-b) pyran;

m) 6-(4-methoxyphenyl)-6-phenyl-12,13-dimethoxy-10,10-dimethyl-6,10-dihydro[2]benzopyrano[3',4':3,4]naphtho (1,2-b)pyran;

n) 2,2-bis(4-methoxphenyl)-12-methoxy-10-oxo-2,10-dihydro[2]benzopyrano[4',3':3,4]naphtho(2,1-b)pyran;

o) 6,6-bis(4-methoxyphenyl)-12-methoxy-10-oxo-6,10-dihydro[2]benzopyrano[3',4':3,4]naphtho(1,2-b)pyran;

p) 6,6-diphenyl-9-oxo-6,9-dihydro[1]benzopyrano [3',4':3,4]naphtho(1,2-b)pyran;

q) 3,3-diphenyl-8-oxo-3,8-dihydro[2]benzopyrano[3',4':5,6] naphtho(2,1-b)pyran; or r) mixtures thereof.

The materials represented by graphic formula IXA, IXB, IXC, IXD, IXE, IXF, IXG or IXH can be produced by methods known to those skilled in the art, for example, as disclosed in U.S. Pat. Nos. 6,022,495 and 6,149,841.

In one non-limiting embodiment, a photochromic material is chosen from a naphthopyran represented by the following graphic formulae XA or XB:

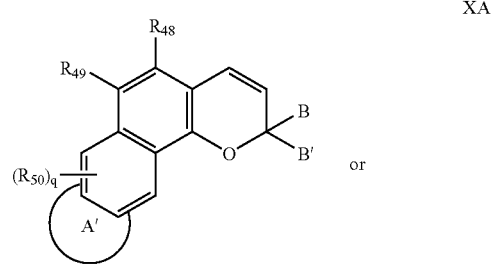

-continued

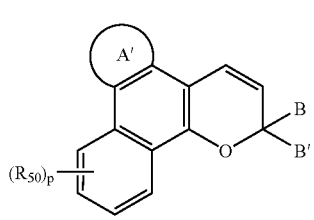

XB wherein,
(a) A' is chosen from:
  (i) an unsubstituted, mono-substituted or di-substituted heterocyclic ring chosen from benzothieno, benzofurano or indolo, the 2,3 or 3,2 positions of said heterocyclic ring being fused to the i, j or k side of said naphthopyran represented by graphic formula XA or said heterocyclic ring is fused to the f side of said naphthopyran represented by graphic formula XB; or
  (ii) an unsubstituted, mono-substituted or di-substituted indeno group fused to the i, j or k side of said naphthopyran represented by graphic formula XA or to the f side of said naphthopyran represented by graphic formula XB; each of said heterocyclic ring and indeno group substituents being $C_1$–$C_6$ alkyl, $C_5$–$C_7$ cycloalkyl, $C_1$–$C_6$ alkoxy, —N($R_{10}$)$R_{11}$, which was described hereinbefore in (d) for the material represented by graphic formula I, chloro, fluoro, benzo, mono- or di-substituted benzo group fused to the benzo portion of the benzothieno, benzofurano, indeno or indolo moiety, said benzo substitutent being $C_1$–$C_6$ alkyl, $C_5$–$C_7$ cycloalkyl, $C_1$–$C_6$ alkyl mono-substituted ($C_5$–$C_7$)cycloalkyl, $C_1$–$C_6$ alkoxy, —N($R_{10}$)$R_{11}$, chloro or fluoro;
(b) $R_{48}$ is chosen from:
  (i) —C(O)W', W' being —OR$_9$ or —N($R_{10}$)$R_{11}$, which groups were described hereinbefore in (d) for the material represented by graphic formula I; or
  (ii) —C($R_{51}$)$_2$X', wherein X' is —CN, chloro, fluoro, hydroxy, benzoyloxy, $C_1$–$C_6$ alkoxy, $C_2$–$C_6$ acyloxy, amino, $C_1$–$C_6$ mono-alkylamino, $C_1$–$C_6$ dialkylamino, morpholino, piperidino, 1-indolinyl, pyrrolidyl, or trimethylsilyloxy, $R_{51}$ is hydrogen, $C_1$–$C_6$ alkyl, phenyl or naphthyl, and each of said phenyl and heterocyclic ring substituents in this part (b) being $C_1$–$C_6$ alkyl or $C_1$–$C_6$ alkoxy;
(c) $R_{49}$ is hydrogen, $C_1$–$C_6$ alkyl, the mono-, di- or tri-substituted aryl groups phenyl or naphthyl, said aryl substituents being $C_1$–$C_6$ alkyl, $C_1$–$C_6$ alkoxy, chloro or fluoro; or
(d) each $R_{50}$ is chloro, fluoro, $C_1$–$C_6$ alkyl, $C_1$–$C_6$ alkoxy, phenyl, naphthyl, phenoxy, naphthoxy or the group, —N($R_{10}$)$R_{11}$, which was described hereinbefore in (d) for the material represented by graphic formula I, and q is selected from the integers 0, 1 or 2 in said naphthopyran represented by graphic XA, or each $R_{50}$ is chloro, fluoro, phenoxy, naphthoxy or the group, —N($R_{10}$)$R_{11}$, and p is selected from the integers 0, 1, 2 or 3 in said naphthopyran represented by graphic formula XB; and
(e) B and B' are each independently chosen from the groups described hereinbefore in (d) for the material represented by graphic formula II.

In another non-limiting embodiment, the naphthopyran is represented by graphic formulae XA or XB wherein:

(a) A' is chosen from:
  (i) an unsubstituted, mono- or di-substituted heterocyclic ring; and
  (ii) an unsubstituted or mono-substituted indeno group, each of said heterocyclic ring and indeno group substituents being $C_1$–$C_4$ alkyl, $C_1$–$C_3$ alkoxy, —N($R_{10}$)$R_{11}$, which was described hereinbefore in (d) for the material represented by graphic formula I, benzo, mono- or di-substituted benzo group fused to the indeno moiety, said benzo substitutents being $C_1$–$C_3$ alkyl, $C_1$–$C_3$ alkoxy or —N($R_{10}$)$R_{11}$;
(b) $R_{48}$ is chosen from:
  (i) —C(O)W', W' being —OR$_9$ or —N($R_{10}$)$R_{11}$, wherein said groups were described hereinbefore in (d) for the material represented by graphic formula I; or
  (ii) —C($R_{51}$)$_2$X', wherein X' is —CN, halogen, hydroxy, benzoyloxy, $C_1$–$C_4$ alkoxy, $C_2$–$C_4$ acyloxy, amino, $C_1$–$C_4$ mono-alkylamino, $C_1$–$C_4$ dialkylamino, morpholino, piperidino, 1-indolinyl or pyrrolidyl, and $R_{51}$ is hydrogen, $C_1$–$C_4$ alkyl, phenyl or naphthyl;
(c) $R_{49}$ is hydrogen, $C_1$–$C_4$ alkyl, the mono- or di-substituted aryl groups phenyl or naphthyl, said aryl substituents being $C_1$–$C_4$ alkyl or $C_1$–$C_4$ alkoxy, chloro or fluoro;
(d) each $R_{50}$ is fluoro, $C_1$–$C_4$ alkyl, $C_1$–$C_4$ alkoxy, phenyl, naphthyl, phenoxy, naphthoxy, or the group, —N($R_{10}$)$R_{11}$, which was described hereinbefore in (d) for the material represented by graphic formula I, and q is selected from the integers 0, 1 or 2 for the naphthopyran represented by graphic formula XA or p is selected from the integers 0, 1, 2 or 3 for the naphthopyran represented by graphic formula XB; and
(e) B and B' are each independently chosen from the groups described hereinbefore in (d) for the material represented by graphic formula II.

In a further non-limiting embodiment, the naphthopyran represented by graphic formula XA or XB is chosen from:
(a) 2,2-bis(4-methoxyphenyl)-5-methoxycarbonyl-6-methyl-2H-benzofuro[2',3':7,8]naphtho[12-b]pyran;
(b) 2-(4-methoxyphenyl)-2-(4-propoxyphenyl)-5-methoxycarbonyl-6-methyl-2H-benzofuro[2',3':7,8]naphtho[12-b]pyran;
(c) 2,2'-Spiroadamantylene-5-methoxycarbonyl-6-methyl-2H-benzofuro[2',3':7,8]naphtho[1,2-b]pyran;
(d) 3,3-Bis(4-methoxyphenyl)-10-methoxy-3H-naphtho[2'',1'':4',5']furo[2',3':3,4]naphtho[1,2-b]pyran;
(e) 3,3-Bis(4-methoxyphenyl)-3H-naphtho[1'',2'':4',5']furo[3',2':3,4]naphtho[1,2-b]pyran;
(f) 3,3'-Spiroadamantylene-3H-naphtho[1'',2'':4',5']furo[3',2':3,4]naphtho[1,2-b]pyran;
(g) 2,2-bis(4-methoxyphenyl)-5-methoxycarbonyl-6-methyl-2H-indeno[3',2':7:8]naphtho[1,2-b]pyran;
(h) 3,3-di(4-methoxyphenyl)-6,11-dimethoxy-13-butyl-13-ethoxy-13H-3H-indeno[2',3',3,4]naphtho[1,2-b]pyran;
(i) 3,3-di(4-methoxyphenyl)-10,11-dimethoxy-13,13-dimethyl-13H-3H-indeno[2',3',3,4]naphtho[1,2-b]pyran; or
(j) mixtures thereof.

The materials represented by graphic formula XA or XB can be produced by methods known to those skilled in the art, for example, as disclosed in U.S. Pat. No. 5,651,923.

In one non-limiting embodiment, a photochromic material is chosen from a indenonaphthopyran represented by the following graphic formulae XIA or XIB:

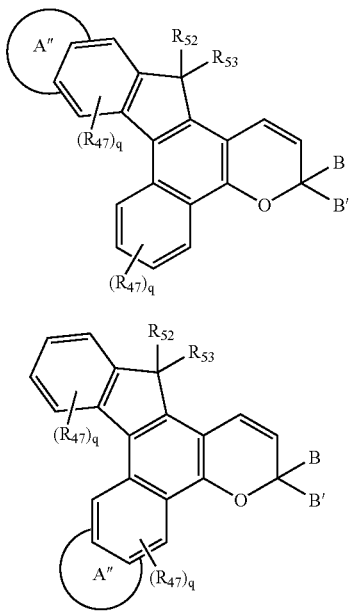

wherein, (a) A" is an unsubstituted, mono-substituted or di-substituted heterocyclic ring chosen from furo, thieno, benzothieno, benzofurano and indolo, the 2,3 or 3,2 positions of said heterocyclic ring being fused to the g, h, i, n, o or p side of said indenonaphthopyran, said heterocyclic ring substituents being $C_1$–$C_6$ alkyl, $C_5$–$C_7$ cycloalkyl, $C_1$–$C_6$ alkoxy, chloro or fluoro;

(b) $R_{52}$ and $R_{53}$ together form an oxo group, a spiro heterocyclic group having 2 oxygen atoms and from 3 to 6 carbon atoms including the spirocarbon atom, or $R_{52}$ and $R_{53}$ are each hydrogen, hydroxy, $C_1$–$C_6$ alkyl, $C_3$–$C_7$ cycloalkyl, allyl, phenyl, mono-substituted phenyl, benzyl, mono-substituted benzyl, chloro, fluoro or the group, —C(O)W", wherein each W" is hydroxy, $C_1$–$C_6$ alkyl, $C_1$–$C_6$ alkoxy, phenyl, mono-substituted phenyl, amino, mono($C_1$–$C_6$) alkylamino, di($C_1$–$C_6$)alkylamino, morpholino, piperidino or pyrrolidyl; or $R_{52}$ and $R_{53}$ are each the group, the group, —N($R_{10}$)$R_{11}$, as described hereinbefore in (d) for the material represented by graphic formula I, or —OR$_{54}$, wherein each $R_{54}$ is $C_1$–$C_6$ alkyl, phenyl($C_1$–$C_3$)alkyl, mono($C_1$–$C_6$)alkyl substituted phenyl($C_1$–$C_3$)alkyl, mono($C_1$–$C_6$)alkoxy substituted phenyl($C_1$–$C_3$)alkyl, $C_1$–$C_6$ alkoxy($C_2$–$C_4$)alkyl, $C_3$–$C_7$ cycloalkyl, mono($C_1$–$C_4$)alkyl substituted $C_3$–$C_7$ cycloalkyl, $C_1$–$C_6$ chloroalkyl, $C_1$–$C_6$ fluoroalkyl, allyl, the group, —CH($R_{55}$)X", wherein each $R_{55}$ is hydrogen or $C_1$–$C_3$ alkyl, each X" is —CN, —CF$_3$, or —COOR$_{55}$, or each $R_{54}$ is the group, —C(O)Y', wherein each Y' is hydrogen, $C_1$–$C_6$ alkyl, $C_1$–$C_6$ alkoxy, the unsubstituted, mono- or di-substituted aryl groups, phenyl and naphthyl, phenoxy, mono- or di-($C_1$–$C_6$)alkyl substituted phenoxy, mono- or di-($C_1$–$C_6$)alkoxy substituted phenoxy, amino, mono ($C_1$–$C_6$)alkylamino, di($C_1$–$C_6$)alkylamino, phenylamino, mono- or di-($C_1$–$C_6$)alkyl substituted phenylamino or mono- or di-($C_1$–$C_6$)alkoxy substituted phenylamino, each of said phenyl, benzyl and aryl group substituents being $C_1$–$C_6$ alkyl or $C_1$–$C_6$ alkoxy;

(c) each $R_{47}$ and q are the same as described hereinbefore in (d) for the material represented by graphic formula VIII; and (d) B and B' are each independently chosen from the groups described hereinbefore in (d) for the material represented by graphic formula II.

In another non-limiting embodiment, the naphthopyran is represented by graphic formulae XIA or XIB wherein:

(a) A" is an unsubstituted, mono-substituted or di-substituted heterocyclic ring chosen from furo, thieno, benzothieno, benzofurano or indolo, the 2,3 or 3,2 positions of said heterocyclic ring being fused to the p side of said indenonaphthopyran, said heterocyclic ring substituents being $C_1$–$C_6$ alkyl;

(b) $R_{52}$ and $R_{53}$ together form an oxo group, a spiro heterocyclic group having 2 oxygen atoms and from 3 to 6 carbon atoms including the spirocarbon atom, or $R_{52}$ and $R_{53}$ are each hydrogen, hydroxy, $C_1$–$C_6$ alkyl, $C_3$–$C_7$ cycloalkyl, phenyl or the group, —C(O)W", wherein each W" is $C_1$–$C_6$ alkoxy, mono($C_1$–$C_6$)alkylamino or di($C_1$–$C_6$)alkylamino, or $R_{52}$ and $R_{53}$ are each the group, —N($R_{10}$)$R_{11}$, as described hereinbefore in (d) for the material represented by graphic formula I, or —OR$_{54}$, wherein each $R_{54}$ is $C_1$–$C_6$ alkyl, phenyl($C_1$–$C_3$)alkyl, the group, —CH($R_{55}$)X", wherein each $R_{55}$ is hydrogen or $C_1$–$C_3$ alkyl, each X" is —COOR$_{55}$, or each $R_{54}$ is the group, —C(O)Y', wherein each Y' is $C_1$–$C_6$ alkyl;

(c) each $R_{47}$ and q are the same as described hereinbefore in (d) for the material represented by graphic formula VIII; and (d) B and B' are each independently chosen from the groups described hereinbefore in (d) for the material represented by graphic formula II.

In a further non-limiting embodiment, the naphthopyran represented by graphic formula XIA or XIB is chosen from:

(a) 3,3-di(4-methoxyphenyl)-16-hydroxy-16-ethyl-16H-benzofuro[2',3':7,8]indeno[2',3':3,4]naphtho[1,2-b]pyran;

(b) 3,3-di(4-methoxyphenyl)-16-hydroxy-16H-benzofuro [2",3":6',7']indeno[3',2':4,3]naphtho[1,2-b]pyran;

(c) 3,3-di(4-methoxyphenyl)-16-hydroxy-16-ethyl-16H-benzofuro[2",3":6',7']indeno[3',2':4,3]naphtho[1,2-b]pyran; or (d) mixtures thereof.

The materials represented by graphic formula XIA or XIB can be produced by methods known to those skilled in the art, for example, as disclosed in U.S. Pat. No. 5,698,141.

In one non-limiting embodiment, a photochromic material is chosen from an indenonaphthopyran represented by graphic formulae XIIA or XIIB wherein:

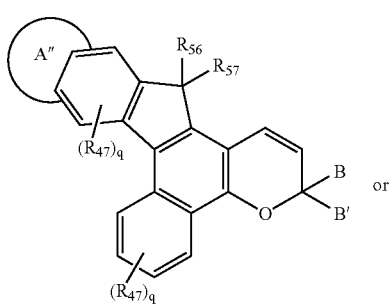

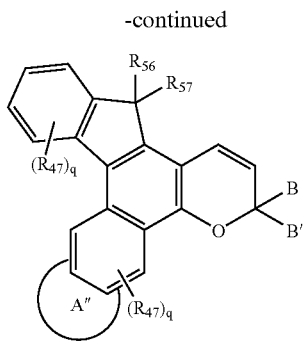

XIIB (a) A" is the same as described hereinbefore in (a) for the material represented by graphic formula XIA or XIB;

(b) $R_{56}$ is hydrogen, hydroxy, bromo, fluoro or chloro and $R_{57}$ is the group, —CH(V')$_2$, wherein V' is —CN or —COOR$_{58}$, and each $R_{58}$ is hydrogen, $C_1$–$C_6$ alkyl, phenyl ($C_1$–$C_3$)alkyl, mono($C_1$–$C_6$)alkyl substituted phenyl ($C_1$–$C_3$)alkyl, mono($C_1$–$C_6$)alkoxy substituted phenyl ($C_1$–$C_3$)alkyl or the unsubstituted, mono- or di-substituted aryl groups phenyl or naphthyl, or $R_{57}$ is the group, —CH($R_{59}$)Y", wherein $R_{59}$ is hydrogen, $C_1$–$C_6$ alkyl or the unsubstituted, mono- or di-substituted aryl groups phenyl or naphthyl, and Y" is —COOR$_{58}$, —COR$_{59}$, or —CH$_2$OR$_{60}$, wherein $R_{59}$ is hydrogen, $C_1$–$C_6$ alkyl, the unsubstituted, mono- or di-substituted aryl groups phenyl or naphthyl, amino, mono($C_1$–$C_6$)alkylamino, di($C_1$–$C_6$)alkylamino, phenylamino, mono- or di-($C_1$–$C_6$)alkyl substituted phenylamino, mono- or di-($C_1$–$C_6$)alkoxy substituted phenylamino, diphenylamino, mono- or di-($C_1$–$C_6$)alkyl substituted diphenylamino, mono- or di-($C_1$–$C_6$)alkoxy substituted diphenylamino, morpholino, or piperidino; $R_{60}$ is hydrogen, —COR$_{58}$, $C_1$–$C_6$ alkyl, $C_1$–$C_3$ alkoxy($C_1$–$C_6$) alkyl, phenyl($C_1$–$C_3$)alkyl, mono($C_1$–$C_6$)alkyl substituted phenyl($C_1$–$C_3$)alkyl, mono($C_1$–$C_6$)alkoxy substituted phenyl($C_1$–$C_3$)alkyl, or the unsubstituted, mono- or di-substituted aryl groups phenyl or naphthyl, each of said aryl group substituents being $C_1$–$C_6$ alkyl or $C_1$–$C_6$ alkoxy; or (c) $R_{56}$ and $R_{57}$ together form the group, =C(V')$_2$ or =C($R_{59}$)W''', wherein W''' is —COOR$_{58}$ or —COR$_{59}$;

(d) each $R_{47}$ and q are the same as described hereinbefore in (d) for the material represented by graphic formula VIII; and (e) B and B' are each independently chosen from the groups described hereinbefore in (d) for the material represented by graphic formula II.

In another non-limiting embodiment, the naphthopyran is represented by graphic formulae XIIA or XIIB wherein:

(a) A" is the same as described hereinbefore in (a) for the material represented by graphic formula XIA or XIB;

(b) $R_{56}$ is hydrogen or hydroxy and $R_{57}$ is the group, —CH(V')$_2$, wherein V' is —COOR$_{58}$, and each $R_{58}$ is $C_1$–$C_6$ alkyl or phenyl($C_1$–$C_3$)alkyl; or $R_{57}$ is the group, —CH($R_{59}$)Y", wherein $R_{59}$ is hydrogen and Y" is —COOR$_{58}$, or —CH$_2$OR$_{60}$ wherein $R_{59}$ is $C_1$–$C_6$ alkyl or di($C_1$–$C_6$)alkylamino; and $R_{60}$ is $C_1$–$C_6$ alkyl; or (c) $R_{56}$ and $R_{57}$ together form the group, =C($R_{59}$)W''', wherein W''' is —COOR$_{58}$;

(d) each $R_{47}$ and q are the same as described hereinbefore in (d) for the material represented by graphic formula VIII; and (e) B and B' are each independently chosen from the groups described hereinbefore in (d) for the material represented by graphic formula II.

In a further non-limiting embodiment, the naphthopyran represented by graphic formula XIIA or XIIB is chosen from:

(a) 3,3-di-(4-methoxyphenyl)-16-(ethoxycarbonyl) methyl-16-hydroxy-3,16-di[H]-benzofuro[2',3':7,8]indeno [2',3':3,4]naphtho[1,2-b]pyran;

(b) 3-(4-methoxyphenyl)-3-(4-morpholinophenyl)-16-(ethoxycarbonyl)methyl-16-hydroxy-3,16-di[H]-benzofuro [2',3':7,8]indeno[2',3':3,4]naphtho[1,2-b]pyran;

(c) 3-phenyl-3-(4-methoxyphenyl)-16-(ethoxycarbonyl)methyl-16-hydroxy-3,16-di[H]-benzofuro [2",3":6',7']indeno[3',2':4,3]naphtho[1,2-b]pyran;

(d) 3-phenyl-3-(4-morpholinophenyl)-16-(ethoxycarbonyl) methyl-16-hydroxy-3,16-di[H]-benzofuro [2",3":6',7']indeno[3',2':4,3]naphtho[1,2-b]pyran; or (e) mixtures thereof.

The materials represented by graphic formula XIIA or XIIB can be produced by methods known to those skilled in the art, for example, as disclosed in U.S. Pat. No. 5,723,072.

In one non-limiting embodiment, the Behind The Windshield (BWS) photochromic material is chosen from an indenonaphthopyran represented by the following graphic formula XIII:

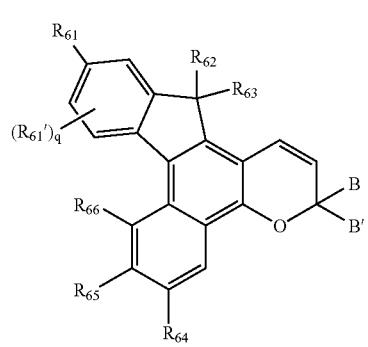

XIII wherein, (a) $R_{61}$ is represented by:

(i) —SR$_{67}$, $R_{67}$ being chosen from $C_1$–$C_6$ alkyl, aryl, mono- or di-substituted aryl, said aryl group being phenyl or naphthyl and each of said aryl substituents being chosen independently from $C_1$–$C_6$ alkyl, $C_1$–$C_6$ alkoxy or halogen;

(ii) an amino group described hereinbefore in (b) (i), (ii), (iii) (iv) or (v) for the material represented by graphic formula IV;

(b) R61' is independently chosen for each occurrence from $C_1$–$C_6$ alkyl or $C_1$–$C_6$ alkoxy and q being chosen from the integer 0, 1 or 2;

(c) $R_{62}$ and $R_{63}$ are each independently chosen from:

(i) hydrogen, hydroxy, amino, mono- or di-substituted amino, $C_1$–$C_{12}$ alkyl, $C_3$–$C_{12}$ alkylidene, $C_2$–$C_{12}$ alkylidyne, vinyl, $C_3$–$C_7$ cycloalkyl, $C_1$–$C_6$ alkoxyalkyl, allyl, benzyl, mono-substituted benzyl, chloro, fluoro or -C(O)W", wherein W" being the same group described hereinbefore in (b) for the material represented by graphic formula XIA or XIB; said amino substituents in (c) (i) being $C_1$–$C_6$ alkyl, phenyl, benzyl or naphthyl; each of said benzyl substituents being $C_1$-$C_6$ alkyl or $C_1$-$C_6$ alkoxy;
(ii) an unsubstituted, mono- di- or tri-substituted group chosen from phenyl, naphthyl, phenanthryl, pyrenyl, quinolyl, isoquinolyl, benzofuranyl, thienyl, benzothienyl, dibenzofuranyl, dibenzothienyl, carbazolyl or indolyl; each of said group substituents in (c) (ii) being chosen independently for each occurrence from chloro, fluoro, $C_1$-$C_6$ alkyl or $C_1$-$C_6$ alkoxy;
(iii) a monosubstituted phenyl, said phenyl having a substituent located at the para position being as described hereinbefore in (d) (v) for the material represented by graphic formula II;
(iv) $OR_{67'}$, $R_{67'}$ being chosen from $C_1$-$C_6$ alkyl, $C_1$-$C_6$ acyl, phenyl($C_1$-$C_3$)alkyl, mono($C_1$-$C_6$)alkyl substituted phenyl($C_1$-$C_3$)alkyl, mono($C_1$-$C_6$)alkoxy substituted phenyl($C_1$-$C_3$)alkyl, $C_1$-$C_6$ alkoxy($C_2$-$C_4$)alkyl, $C_3$-$C_7$ cycloalkyl, mono($C_1$-$C_4$)alkyl substituted $C_3$-$C_7$ cycloalkyl, $C_1$-$C_6$ chloroalkyl, $C_1$-$C_6$ fluoroalkyl, allyl, tri($C_1$-$C_6$)alkylsilyl, tri($C_1$-$C_6$)alkoxysilyl, di($C_1$-$C_6$)alkyl ($C_1$-$C_6$)alkoxysilyl, di($C_1$-$C_6$)alkoxy ($C_1$-$C_6$)alkylsilyl, benzoyl, mono-substituted benzoyl, naphthoyl or mono-substituted naphthoyl; each of said benzoyl and naphthoyl substituents being independently chosen from $C_1$-$C_6$ alkyl or $C_1$-$C_6$ alkoxy; or $R_{67'}$ being —$CH(R_{68})Q''$, wherein $R_{68}$ being chosen from hydrogen or $C_1$-$C_3$ alkyl and $Q''$ being chosen from —CN, —$CF_3$, or —$COOR_{68}$; or $R_{67'}$ being —$C(O)V''$, wherein $V''$ being chosen from hydrogen, $C_1$-$C_6$ alkoxy, phenoxy, mono- or di-($C_1$-$C_6$)alkyl substituted phenoxy, mono- or di-($C_1$-$C_6$)alkoxy substituted phenoxy, an unsubstituted, mono- or di-substituted aryl group, phenyl or naphthyl, amino, mono ($C_1$-$C_6$)alkylamino, di($C_1$-$C_6$)alkylamino, phenylamino, mono- or di-($C_1$-$C_6$)alkyl substituted phenylamino, or mono- or di-($C_1$-$C_6$)alkoxy substituted phenylamino; each of said aryl group substituents being independently chosen from $C_1$-$C_6$ alkyl or $C_1$-$C_6$ alkoxy;
(v)-$CH(Q''')_2$, $Q'''$ being chosen from —-CN or —$COOR_{69}$ and $R_{69}$ being chosen from hydrogen, $C_1$-$C_6$ alkyl, phenyl($C_1$-$C_3$)alkyl, mono($C_1$-$C_6$)alkyl substituted phenyl ($C_1$-$C_3$)alkyl, mono($C_1$-$C_6$)alkoxy substituted phenyl($C_1$-$C_3$)alkyl or an unsubstituted, mono- or di-substituted aryl group, phenyl or naphthyl; each of said aryl group substituents being independently chosen from $C_1$-$C_6$ alkyl or $C_1$-$C_6$ alkoxy;
(vi) —$CH(R_{70})G''$, $R_{70}$ being chosen from hydrogen, $C_1$-$C_6$ alkyl or an unsubstituted, mono- or di-substituted aryl group, phenyl or naphthyl, and $G''$ being chosen from —$COOR_{69}$, —$COR_{71}$ or —$CH_2OR_{72}$, wherein $R_{71}$ being chosen from hydrogen, $C_1$-$C_6$ alkyl, an unsubstituted, mono- or di-substituted aryl group, phenyl or naphthyl, amino, mono($C_1$-$C_6$)alkylamino, di($C_1$-$C_6$)alkylamino, phenylamino, mono- or di-($C_1$-$C_6$)alkyl substituted phenylamino, mono- or di-($C_1$-$C_6$)alkoxy substituted phenylamino, diphenylamino, mono- or di($C_1$-$C_6$)alkyl substituted diphenylamino, mono- or di($C_1$-$C_6$)alkoxy substituted diphenylamino, morpholino or piperidino; $R_{72}$ being chosen from hydrogen, —$C(O)R_{69}$, $C_1$-$C_6$ alkyl, $C_1$-$C_3$ alkoxy($C_1$-$C_6$)alkyl, phenyl($C_1$-$C_3$)alkyl, mono ($C_1$-$C_6$)alkoxy substituted phenyl($C_1$-$C_3$)alkyl or an unsubstituted, mono- or di-substituted aryl group, phenyl or naphthyl, each of said aryl group substituents being independently chosen from $C_1$-$C_6$ alkyl or $C_1$-$C_6$ alkoxy;
(vii) the group T being the same as described hereinbefore in (d) (i) for the material represented by graphic formula II; or
(viii) $R_{62}$ and $R_{63}$ together form an oxo group or a substituted or unsubstituted spiro-carbocyclic ring containing 3 to 6 carbon atoms or a substituted or unsubstituted spiro-heterocyclic group containing 1 or 2 oxygen atoms and 3 to 6 carbon atoms including the spirocarbon atom, said spiro-carbocyclic ring and spiro-heterocyclic group being annellated with 0, 1 or 2 benzene rings, said substituents being hydrogen or $C_1$-$C_6$ alkyl;
(d) $R_{64}$ is chosen from hydrogen, $C_1$-$C_6$ alkyl or the group $R_a$ chosen from:
(i) —$OR_{73}$, $R_{73}$ being chosen from phenyl($C_1$-$C_3$)alkyl, $C_1$-$C_6$ alkyl, mono($C_1$-$C_6$)alkyl substituted phenyl ($C_1$-$C_3$)alkyl, mono($C_1$-$C_6$)alkoxy substituted phenyl ($C_1$-$C_3$)alkyl, $C_1$-$C_6$ alkoxy($C_2$-$C_4$)alkyl, $C_3$-$C_7$ cycloalkyl, mono($C_1$-$C_4$)alkyl substituted $C_3$-$C_7$ cycloalkyl, $C_1$-$C_6$ chloroalkyl, $C_1$-$C_6$ fluoroalkyl, allyl or —$CH(R_{68})Q''$ described in (c) (i); or
(ii) an amino group described hereinbefore in (b) (i), (ii), (iii), (iv) or (v) for the material represented by graphic formula IV;
(e) $R_{65}$ is chosen from hydrogen, $C_1$-$C_6$ alkyl or $R_a$, said $R_a$ being the same as described hereinbefore in (d);
(f) $R_{66}$ is chosen from hydrogen, $C_1$-$C_6$ alkyl or $R_a$, said $R_a$ being the same as described hereinbefore in (d); or
(g) $R_{65}$ and $R_{66}$ together form one of the following graphic formulae:

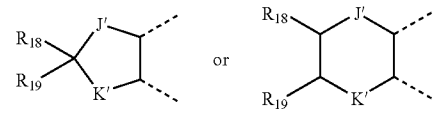

wherein $J'$ and $K'$ being independently chosen for each occurrence in each formula from oxygen or —$N(R_{15})$—, said groups $R_{15}$ $R_{18}$ and $R_{19}$ each being the same as described hereinbefore in (b) and (d) (vi) for the material represented by graphic formula II;
(h) B and B' are each independently chosen from the groups described hereinbefore in Cd) for the material represented by graphic formula II.
In another non-limiting embodiment, the indenonaphthopyran is represented by graphic formula XIII wherein:
(a) $R_{61}$ is represented by:
(i) —$SR_{67}$, $R_{67}$ being $C_1$-$C_6$ alkyl or aryl;
(ii) an amino group described hereinbefore in (b) (i), (ii) or (iii) for the material represented by graphic formula IV;
(b) $R_{61}'$ is independently chosen for each occurrence from $C_1$-$C_6$ alkyl or $C_1$-$C_6$ alkoxy and q being the integer 1;
(c) $R_{62}$ and $R_{63}$ are each independently chosen from:
(i) hydrogen, hydroxy, $C_1$-$C_{12}$ alkyl, $C_3$-$C_{12}$ alkylidene, $C_3$-$C_7$ cycloalkyl, or —$C(O)W''$, wherein $W''$ being the same group described hereinbefore in (b) for the material represented by graphic formula XIA or XIB;
(ii) an unsubstituted, mono- di- or tri-substituted group chosen from phenyl; each of said phenyl substituents in (c) (ii) being chosen independently for each occurrence from chloro, fluoro, $C_1$-$C_6$ alkyl or $C_1$-$C_6$ alkoxy;
(iii) a monosubstituted phenyl, said phenyl having a substituent located at the para position being as described hereinbefore in (d) for the material represented by graphic formula II;

(iv) $OR_{67}R_{67}$, being chosen from $C_1–C_6$ alkyl, phenyl $(C_1–C_3)$alkyl, $C_1–C_6$ alkoxy$(C_2–C_4)$alkyl or tri$(C_1–C_6)$ alkylsilyl;

(v) —CH(Q''')$_2$, Q''' being chosen from —COOR$_{69}$ and R$_{69}$ being $C_1–C_6$ alkyl;

(vi) —CH(R$_{70}$)G'', R$_{70}$ being chosen from hydrogen, $C_1–C_6$ alkyl or an unsubstituted, mono- or di-substituted aryl group, phenyl or naphthyl, and G'' being chosen from —COOR$_{69}$, —COR$_{71}$ or —CH$_2$OR$_{72}$, wherein R$_{71}$ being chosen from hydrogen, $C_1–C_6$ alkyl, an unsubstituted, mono- or di-substituted aryl group, phenyl or naphthyl, amino, mono($C_1–C_6$)alkylamino, di($C_1–C_6$)alkylamino, phenylamino, mono- or di-($C_1–C_6$)alkyl substituted phenylamino, mono- or di-($C_1–C_6$)alkoxy substituted phenylamino, diphenylamino, mono- or di($C_1–C_6$)alkyl substituted diphenylamino, mono- or di($C_1–C_6$)alkoxy substituted diphenylamino, morpholino or piperidino; R$_{72}$ being chosen from hydrogen, —C(O)R$_{69}$, $C_1–C_6$ alkyl, $C_1–C_3$ alkoxy($C_1–C_6$)alkyl, phenyl($C_1–C_3$)alkyl, mono ($C_1–C_6$)alkoxy substituted phenyl($C_1–C_3$)alkyl or an unsubstituted, mono- or di-substituted aryl group, phenyl or naphthyl, each of said aryl group substituents being independently chosen from $C_1–C_6$ alkyl or alkoxy;

(vii) the group T described hereinbefore in (d) (i) for the material represented by graphic formula II; or (viii) R$_{62}$ and R$_{63}$ together form an oxo group or a substituted or unsubstituted spiro-carbocyclic ring containing 3 to 6 carbon atoms or a substituted or unsubstituted spiro-heterocyclic group containing 1 or 2 oxygen atoms and 3 to 6 carbon atoms including the spirocarbon atom, said spiro-carbocyclic ring and spiro-heterocyclic group being annellated with 0, 1 or 2 benzene rings, said substituents being hydrogen or $C_1–C_6$ alkyl;

(d) R$_{64}$ is chosen from hydrogen, $C_1–C_6$ alkyl or the group R$_a$ chosen from:

(i) —OR$_{73}$, R$_{73}$ being chosen from phenyl($C_1–C_3$)alkyl, $C_1–C_6$ alkyl, mono($C_1–C_6$)alkyl substituted phenyl ($C_1–C_3$)alkyl, mono($C_1–C_6$)alkoxy substituted phenyl $(C_1–C_3)$alkyl, $C_1–C_6$ alkoxy($C_2–C_4$)alkyl, $C_3–C_7$ cycloalkyl, mono($C_1–C_4$)alkyl substituted $C_3–C_7$ cycloalkyl, $C_1–C_6$ chloroalkyl, $C_1–C_6$ fluoroalkyl, allyl or —CH(R$_{68}$)Q''; or (ii) an amino group described hereinbefore in (b) (i), (ii) or (iii) for the material represented by graphic formula IV;

(e) R$_{65}$ is chosen from hydrogen, $C_1–C_6$ alkyl or R$_a$, said R$_a$ being the same as described hereinbefore in (d);

(f) R$_{66}$ is chosen from hydrogen, $C_1–C_6$ alkyl or R$_a$, said R$_a$ being the same as described hereinbefore in (d); or (g) R$_{65}$ and R$_{66}$ together form one of the following graphic formulae:

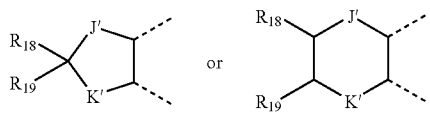

wherein J' and K' being independently chosen for each occurrence in each formula from oxygen or —N(R$_{15}$)—, said groups R$_{15}$, R$_{19}$ and R$_{20}$ each being the same as described hereinbefore in (b) and (d) (vi) for the material represented by graphic formula II;

(h) B and B' are each independently chosen from the groups described hereinbefore in (d) for the material represented by graphic formula II.

In a further non-limiting embodiment, the indenonaphthopyran represented by graphic formula XIII is chosen from:

(a) 3,3-di(4-methoxyphenyl)-11-morpholino-13,13-dimethyl-3H,13H-indeno[2',3':3,4]naphtho[1,2-b]pyran;

(b) 3-phenyl-3-(4-morpholino-phenyl)-11-morpholino-13,13-dimethyl-3H,13H-indeno[2',3':3,4]naphtho-[1,2-b]pyran;

(c) 3,3-di(4-(2-methoxyethoxyphenyl))-11-morpholino-13,13-dimethyl-3H, 13H-indeno[2',3':3,4]naphtho[1,2-b]pyran;

(d) 3,3-di(4-methoxyphenyl)-11-morpholino-13-hydroxy-13-ethyl-3H,13H-indeno[2',3':3,4]naphtho[1,2-b]pyran;

(e) 3,3-di(4-methoxyphenyl)-10-methoxy-11-morpholino-13,13-dimethyl-3H,13H-indeno[2',3':3,4]naphtho[1,2-b]pyran;

(f) 3-(4-methoxyphenyl)-3-(4-morpholinophenyl)-10-methoxy-11-morpholino-13,13-dimethyl-3H, 13H-indeno[2', 3':3,4]naphtho[1,2-b]pyran;

(g) 3-(3,4-dimethoxyphenyl)-3-(4-methoxyphenyl)-11-morpholino-13,13-dimethyl-3H,13H-indeno[2',3':3,4]naphtho[1,2-b]pyran;

(h) 3-(4-methoxyphenyl)-3-(4-morpholinophenyl)-11-morpholino-13,13-dimethyl-3H, 13H-indeno[2',3':3,4]naphtho[1,2-b]pyran;

(i) 3,3-di(2-methoxyethoxyphenyl)-11-morpholino-13,13-dimethyl-13H-3H-indeno[2',3',3,4]naphtho[1,2-b]pyran; or (j) mixtures thereof.

The materials represented by graphic formula XIII can be produced by the methods disclosed in U.S. patent application Ser. No. 10/393,177 filed even herewith on Mar. 20, 2003, which disclosure is incorporated herein by reference.

In one non-limiting embodiment, a photochromic material is chosen from a indenonaphthopyran represented by the following graphic formula XIV:

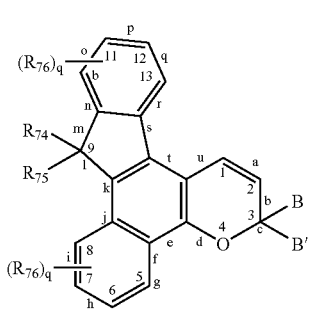

wherein, (a) R$_{74}$ and R$_{75}$ are each the same as R$_{62}$ and R$_{63}$ groups described hereinbefore in (c) for the material represented by graphic formula XIII;

(b) each R$_{76}$ is independently chosen for each occurrence from di($C_1–C_6$)alkylamino, dicyclohexylamino, diphenylamino, piperidyl, morpholinyl, pyridyl, a group T, described hereinbefore in (d) (i) for the material represented by graphic formula II, and group —C(O)W'' described hereinbefore in (b) for the material represented by graphic formula XIII, and q is the integer 0, 1, or 2; or when q is 2, and the $R_{76}$ substituents are adjacent, each pair of substituents independently forms a substituted or unsubstituted fused carbocyclic or heterocyclic ring chosen from benzo, pyridino, pyrazino, pyrimidino, furano, dihydrofurano, 1,3-dioxolo, 1,4-dioxolo, 1,3-dioxino, 1,4-dioxino, thiopheno, benzofuro, benzothieno, indolo, or indeno, the substituents of said fused carbocyclic or heterocyclic ring being chosen from halogen, $C_1$–$C_6$ alkyl, $C_1$–$C_6$ alkoxy, amino, mono- or di-substituted amino, said amino substituents being chosen from $C_1$–$C_6$ alkyl, phenyl, benzyl or naphthyl; said first $R_{76}$ ring being fused to the o, p or q side and said second $R_{76}$ ring being fused to the g, h, or i side of the indenonaphthopyran;

(c) B and B' are each independently chosen from the groups described hereinbefore in (d) for the material represented by graphic formula II.

In another non-limiting embodiment, the indenonaphthopyran is represented by graphic formula XIV wherein:

(a) $R_{74}$ and $R_{75}$ are each the same as $R_{62}$ and $R_{63}$ groups described hereinbefore in (c) for the material represented by graphic formula XIII;

(b) each $R_{76}$ is independently chosen from di($C_1$–$C_6$) alkylamino, dicyclohexylamino, diphenylamino, piperidyl, morpholinyl, pyridyl, halogen, or group —C(O)W" described hereinbefore in (d) for the material represented by graphic formula XIII, and q is the integer 0, 1, or 2; or when q is 2, and the $R_{76}$ substituents are adjacent, each pair of substituents independently forms a substituted or unsubstituted fused carbocyclic or heterocyclic ring chosen from benzo, dihydrofurano, 1,4-dioxolo, 1,3-dioxino, or benzofuro, the substituents of said fused carbocyclic or heterocyclic ring being chosen from the group consisting of $C_1$–$C_6$ alkyl or $C_1$–$C_6$ alkoxy;

(c) B and B' are each independently chosen from the groups described hereinbefore in (d) for the material represented by graphic formula II.

In a further non-limiting embodiment, the indenonaphthopyran represented by graphic formula XIV is chosen from:

(a) 3,3,9-triphenyl-3H-9H-benzo[4",5"]indeno[3',2':3,4]naphtho[1,2-b]pyran;
(b) 3,3-di(4-methoxyphenyl)-9-phenyl-3H-9H-benzo[4",5"]indeno[3',2':3,4]naphtho[1,2-b]pyran;
(c) 3-(4-methoxyphenyl)-3,9-diphenyl-3H-9H-benzo[4",5"]indeno[3',2':3,4]naphtho[1,2-b]pyran;
(d) 3-(4-morpholinophenyl)-3,9-diphenyl-3H-9H-benzo[4",5"]indeno[3',2':3,4]naphtho[1,2-b]pyran;
(e) 3-(4-methoxyphenyl)-3-phenyl-9-methyl-13-methoxy-9-(3-methoxyphenyl)-3H-9H-benzo[4",5"]indeno[3',2':3,4]naphtho[1,2-b]pyran;
(f) 3,3-di(4-methoxyphenyl)-9-methyl-13-methoxy-9-(3-methoxyphenyl)-3H-9H-benzo[4",5"]indeno[3',2':3,4]naphtho[1,2-b]pyran;
(g) 3,3-di(4-methoxyphenyl)-9-methyl-11-methoxy-3H-9H-benzo[4",5"]indeno[3',2':3,4]naphtho [1,2-b]pyran;
(h) 3,3-di(4-methoxyphenyl)-9,9-dimethyl-11-methoxy-3H-9H-benzo[4",5"]indeno[3',2':3,4]naphtho[1,2-b]pyran;
(i) 3-(4-methoxyphenyl)-3-phenyl-9,9-dimethyl-11-methoxy-3H-9H-benzo[4",5"]indeno[3',2':3,4]naphtho[1,2-b]pyran;
(j) 3,3-di(4-methoxyphenyl)-9,9-dimethyl-7,11-dimethoxy-3H-9H-benzo[4",5"]indeno[3',2':3,4]naphtho[1,2-b]pyran;
(k) 3-(4-methoxyphenyl)-3-phenyl-9,9-dimethyl-7,11-dimethoxy-3H-9H-benzo[4",5"]indeno[3',2':3,4]naphtho[1,2-b]pyran;
(l) 3-(4-morpholinophenyl)-3-phenyl-9,9-dimethyl-7,11-dimethoxy-3H-9H-benzo[4",5"]indeno[3',2':3,4]naphtho[1,2-b]pyran;
(m) 3,3-di(4-methoxyphenyl)-9-methyl-11,13-dimethoxy-3H-9H-benzo[4",5"]indeno[3',2':3,4]naphtho[1,2-b]pyran;
(n) 3-(4-methoxyphenyl)-3-phenyl-9-methyl-11,13-dimethoxy-3H-9H-benzo[4",5"]indeno[3',2':3,4]naphtho[1,2-b]pyran;
(o) 3-(4-methoxyphenyl)-3-phenyl-9,9-dimethyl-3H-9H-benzo[4",5"]indeno[3',2':3,4]naphtho[1,2-b]pyran;
(p) 3,3-di(4-methoxyphenyl)-9,9-dimethyl-11-fluoro-3H-9H-benzo[4",5"]indeno[3',2':3,4]naphtho[1,2-b]pyran; or
(q) mixtures thereof.

The materials represented by graphic formula XIV can be produced by the methods disclosed in U.S. patent application Ser. No. 10/039,984 filed on Oct. 29, 2001, which disclosure is incorporated herein by reference.

BWS photochromic materials, including those represented by graphic formulae XIII or a mixture thereof can be used in various non-limiting applications in which photochromic materials can be employed, such as optical lenses, e.g., vision correcting ophthalmic lenses and plano lenses, face shields, goggles, visors, camera lenses, windows, automotive windshields, aircraft and automotive transparencies, e.g., T-roofs, sidelights and backlights, polymeric coatings, plastic films and sheets, textiles and pigmented liquids or pastes, e.g., paints and inks used as verification marks on security documents, e.g., documents such as banknotes, passports and drivers' licenses for which authentication or verification of authenticity may be desired.

In one non-limiting embodiment, it is contemplated that the BWS photochromic materials of the present invention can each be used alone or in combination with other BWS photochromic materials of the present invention, or in combination with one or more other photochromic materials, e.g., photochromic materials having at least one activated absorption maxima within the range of between about 400 and 700 nanometers, and can be incorporated, e.g., dissolved or dispersed, in a polymeric organic host material used to prepare photochromic articles, which become colored when activated to an appropriate hue.

In one non-limiting embodiment, the other photochromic materials can include the following classes of materials: chromenes, e.g., naphthopyrans, benzopyrans, indenonaphthopyrans and phenanthropyrans; spiropyrans, e.g., spiro (benzindoline)naphthopyrans, spiro(indoline)benzopyrans, spiro(indoline)naphthopyrans, spiro(indoline)quinopyrans and spiro(indoline)pyrans; oxazines, e.g., spiro(indoline) naphthoxazines, spiro(indoline)pyridobenzoxazines, spiro (benzindoline)pyridobenzoxazines, spiro(benzindoline) naphthoxazines and spiro(indoline)benzoxazines; mercury dithizonates, fulgides, fulgimides and mixtures of such photochromic materials.

Such photochromic materials and complementary photochromic materials are described in U.S. Pat. No. 4,931,220 at column 8, line 52 to column 22, line 40; U.S. Pat. No. 5,645,767 at column 1, line 10 to column 12, line 57; U.S. Pat. No. 5,658,501 at column 1, line 64 to column 13, line 17; U.S. Pat. No. 6,153,126 at column 2, line 18 to column 8, line 60; U.S. Pat. No. 6,296,785 at column 2, line 47 to column 31, line 5; U.S. Pat. No. 6,348,604 at column 3, line 26 to column 17, line 15; and U.S. Pat. No. 6,353,102 at column 1, line 62 to column 11, line 64, the disclosures of the aforementioned patents are incorporated herein by reference. Spiro(indoline)pyrans are also described in the text,

*Techniques in Chemistry*, Volume III, "Photochromism", Chapter 3, Glenn H. Brown, Editor, John Wiley and Sons, Inc., New York, 1971.

In another non-limiting embodiment, polymerizable photochromic materials, such as polymerizable naphthoxazines disclosed in U.S. Pat. No. 5,166,345 at column 3, line 36 to column 14, line 3; polymerizable spirobenzopyrans disclosed in U.S. Pat. No. 5,236,958 at column 1, line 45 to column 6, line 65; polymerizable spirobenzopyrans and spirobenzothiopyrans disclosed in U.S. Pat. No. 5,252,742 at column 1, line 45 to column 6, line 65; polymerizable fulgides disclosed in U.S. Pat. No. 5,359,085 at column 5, line 25 to column 19, line 55; polymerizable naphthacenediones disclosed in U.S. Pat. No. 5,488,119 at column 1, line 29 to column 7, line 65; polymerizable spirooxazines disclosed in U.S. Pat. No. 5,821,287 at column 3, line 5 to column 11, line 39; polymerizable polyalkoxylated naphthopyrans disclosed in U.S. Pat. No. 6,113,814 at column 2, line 23 to column 23, line 29; and the polymerizable photochromic compounds disclosed in WO97/05213 and application Ser. No. 09/828,260 filed Apr. 6, 2001 can be used. The disclosures of the aforementioned patents on polymerizable photochromic materials are incorporated herein by reference.

Other non-limiting embodiments of photochromic materials that can be used include organo-metal dithiozonates, e.g., (arylazo)-thioformic arylhydrazidates, e.g., mercury dithizonates which are described in, for example, U.S. Pat. No. 3,361,706 at column 2, line 27 to column 8, line 43; and fulgides and fulgimides, e.g., the 3-furyl and 3-thienyl fulgides and fulgimides, which are described in U.S. Pat. No. 4,931,220 at column 1, line 39 through column 22, line 41, the disclosures of which are incorporated herein by reference.

An additional non-limiting embodiment is a form of organic photochromic material resistant to the effects of a polymerization initiator that can also be used in the photochromic articles of the present invention. Such organic photochromic materials include photochromic compounds encapsulated in metal oxides, the latter of which are described in U.S. Pat. Nos. 4,166,043 and 4,367,170 at column 1 line 36 to column 7, line 12, which disclosure is incorporated herein by reference.

In another non-limiting embodiment, inorganic photochromic systems contemplated for use with the BWS materials of the present invention typically contain crystallites of silver halide, cadmium halide and/or copper halide. Other non-limiting inorganic photochromic glass systems can be prepared by the addition of europium (II) and/or cerium (III) to a soda-silica glass. Such inorganic photochromic glass systems are described in Kirk Othmer Encyclopedia of Chemical Technology, 4th Edition, Volume 6, pages 322–325, which disclosure is incorporated herein by reference.

The photochromic materials described herein, e.g., the BWS materials of the present invention and other photochromic materials, can be chosen from a variety of materials. Non-limiting examples include: of course, a single photochromic compound; a mixture of photochromic compounds; a material comprising at least one photochromic compound, such as a plastic polymeric resin or an organic monomeric or oligomeric solution; a material such as a monomer or polymer to which at least one photochromic compound is chemically bonded; a material comprising and/or having chemically bonded to it at least one photochromic compound, the outer surface of the material being encapsulated (encapsulation is a form of coating), for example with a polymeric resin or a protective coating such as a metal oxide that prevents contact of the photochromic material with external materials such as oxygen, moisture and/or chemicals that have a negative effect on the photochromic material, such materials can be formed into a particulate prior to applying the protective coating as described in U.S. Pat. Nos. 4,166,043 and 4,367,170; a photochromic polymer, e.g., a photochromic polymer comprising photochromic compounds bonded together; or mixtures thereof.

The organic photochromic materials and BWS materials of the present invention to be used in a photochromic article can be associated with a polymeric organic host material or other substrate by various means. In a series of non-limiting embodiments, they can be incorporated, e.g., dissolved and/or dispersed, into the host material, polymerized with other components of the host material, e.g., in a reaction injection molding, and/or incorporated into an at least partial coating or film applied to a substrate, e.g., an at least partially cured polymeric coating or a film applied to one surface of the substrate.

In one non-limiting embodiment, a photochromic article adapted to retain at least 12 percent of the delta OD measured in the Outdoor Test when tested in the Behind the Windshield Test can be prepared by a method comprising:

a) obtaining a substrate;
   b) obtaining a photochromic material adapted to change from an unactivated form to an activated form by exposure to radiation substantially in the wavelength range from 380 to 410 nanometers when measured over a range of from 380 to 700 nanometers;
   c) introducing the photochromic material together with said substrate by a method chosen from:
      i) introducing photochromic material (b) with the starting materials used to form said substrate;
      ii) at least partially imbibing photochromic material (b) into at least one surface of said substrate;
      iii) applying at least a partial coating of a polymeric coating composition comprising photochromic material (b) to at least one surface of said substrate;
      iv) at least partially connecting a superstrate comprising photochromic material (b) to at least one surface of said substrate; or
      v) combinations of i), ii), ii) or iv).

In another non-limiting embodiment, the aforementioned method further comprises adding a photochromic material (c) that is different from photochromic material (b), in (c) (i), (ii), (iii), (iv) or (v). In a further non-limiting embodiment, the aforementioned method further comprises adding a fixed tint dye in (c) (i), (ii), (iii), (iv) or (v).

An alternate non-limiting embodiment for producing a photochromic article adapted to exhibit an unactivated state luminous transmittance of greater than 70 percent at 23° C., an activated state luminous transmittance at saturation less than 30 percent when activated at 23° C. by simulated sunlight from a xenon arc lamp set at 6.7 Watts/meter$^2$ UVA and 50,000 lumens/meter$^2$, and an activated state luminous transmittance at saturation less than 60 percent when activated at 28° C. by simulated sunlight from a xenon arc lamp through an UV blocking transparency rendering an irradiance integrated between 380 and 420 nanometers of 0.75 Watts/meter$^2$ and 1,700 lumens/meter$^2$; said method comprising:

a) obtaining a substrate;
   b) obtaining a photochromic material adapted to change from an unactivated form to an activated form by exposure to radiation substantially in the wavelength range from 380 to 410 nanometers when measured over a range of from 380 to 700 nanometers;

c) introducing the photochromic material with said substrate by a method chosen from:
  i) introducing photochromic material (b) with the starting materials used to form the substrate;
  ii) at least partially imbibing photochromic material (b) into at least one surface of the substrate;
  iii) applying at least a partial coating of a polymeric coating composition comprising photochromic material (b) to at least one surface of the substrate;
  iv) at least partially connecting a superstrate comprising photochromic material (b) to at least one surface of the substrate; or
  v) a combination of i), ii), ii) or iv).

In another non-limiting embodiment, the aforementioned method further comprises adding a photochromic material (c) that is different from photochromic material (b), in (c) (i), (ii), (iii), (iv) or (v). In a further non-limiting embodiment, the aforementioned method further comprises adding a fixed tint dye in (c) (i), (ii), (iii), (iv) or (v).

The photochromic articles prepared by the aforementioned methods can be substantially free of ultraviolet radiation absorbing materials adapted to substantially inhibit the activation of the photochromic material by radiation below 380 nm.

Potential substrates for the application of coatings containing BWS photochromic materials or a mixture of BWS photochromic materials and other photochromic include any type of material. Non-limiting examples include, paper, glass, ceramics, wood, masonry, textiles, metals and polymeric organic host materials.

Each of the BWS photochromic materials with or without the other photochromic materials described herein can be used in amounts (or in a ratio) such that a host material or substrate to which the BWS photochromic materials or mixture of BWS photochromic materials and other photochromics is associated, exhibits a desired resultant color, e.g., a substantially neutral color when activated with unfiltered sunlight, e.g., as near a neutral color as possible given the colors of the activated photochromic materials, and a retained coloration, measured as delta OD or $\Delta$OD, of at least 12 percent of that demonstrated under conditions of outdoor exposure when tested in the Behind the Windshield Test described herein in Example 13. In an alternate non-limiting embodiment, the photochromic articles of the present invention demonstrate an activated state luminous transmittance at saturation less than 60 percent when activated under the conditions in the Behind the Windshield Test. In one non-limiting embodiment, the BWS photochromic materials could be used to produce articles having a wide range of colors, e.g., pink. Further discussion of neutral colors and ways to describe colors can be found in U.S. Pat. No. 5,645,767 column 12, line 66 to column 13, line 19.

In one non-limiting embodiment, the amount of the BWS photochromic materials to be applied to or incorporated into a polymeric coating composition and/or polymeric host material of the photochromic article of the present invention can vary widely. Typically, a sufficient amount is used to produce the desired retained coloration behind an UV blocking transparency such as a vehicular windshield. Generally such an amount can be described as a behind the UV blocking transparency activating amount or behind the windshield activating amount. The particular amount used depends often upon the retained coloration desired upon irradiation thereof and upon the method used to incorporate or apply the BWS photochromic materials. Typically, in one non-limiting embodiment, the more BWS photochromic material applied or incorporated, the greater is the coloration retained behind the windshield up to a certain limit. There is a point after which the addition of any more material will not have a noticeable effect, although more material can be added, if desired In one non-limiting embodiment, the amount of the other photochromic materials to be incorporated into a polymeric coating composition and/or polymeric host material can vary widely. Typically, a sufficient amount is used to produce a photochromic effect discernible to the naked eye upon activation. Generally such amount can be described as a photochromic amount. The particular amount used depends often upon the intensity of color desired upon irradiation thereof and upon the method used to incorporate the photochromic materials. Typically, in one non-limiting embodiment, the more photochromic incorporated, the greater is the color intensity up to a certain limit. There is a point after which the addition of any more material will not have a noticeable effect, although more material can be added, if desired.

The relative amounts of the aforesaid BWS photochromic materials or combinations of BWS photochromic materials and other photochromic materials used will vary and depend in part upon the relative intensities of the color of the activated species of such materials, the ultimate color desired, the retained coloration desired and the method of application to the host material and/or substrate. In one non-limiting embodiment, the amount of total photochromic material which includes BWS photochromic materials, other photochromic materials or both, incorporated by imbibition into a photochromic optical host material can vary widely. In alternate non-limiting embodiments, it can range from about 0.01 to about 2.0, or from 0.05 to about 1.0, milligrams per square centimeter of surface to which the photochromic material is incorporated or applied. The amount of total photochromic material incorporated or applied to the host material can range between any combination of these values, inclusive of the recited range, e.g., 0.015 to 1.999 milligrams per square centimeter.

In another non-limiting embodiment, the total amount of photochromic material incorporated into a polymerizable composition for forming a coating, film or polymerizate can vary widely, e.g., it can range from 0.01 to 40 weight percent based on the weight of the solids in the polymerizable composition. In alternate non-limiting embodiments, the concentration of photochromic materials ranges from 0.1 to 30 weight percent, from 1 to 20 weight percent, from 5 to 15 weight percent, or from 7 to 14 weight percent. The amount of photochromic material in the coating can range between any combination of these values, inclusive of the recited range, e.g., 0.011 to 39.99 weight percent.

In one non-limiting embodiment, compatible (chemically and color-wise) tints, e.g., dyes, can be added or applied to the host material used to produce the photochromic article to achieve a more aesthetic result, for medical reasons, or for reasons of fashion. The particular dye selected will vary and depend on the aforesaid need and result to be achieved. In one non-limiting embodiment, the dye can be selected to complement the color resulting from the activated photochromic materials, e.g., to achieve a more neutral color or absorb a particular wavelength of incident light. In another non-limiting embodiment, the dye can be selected to provide a desired hue to the host material when the photochromic materials are in an unactivated state.

In various non-limiting embodiments, adjuvant materials can also be incorporated into host material used to produce the photochromic article. Such adjuvants can be used, prior to, simultaneously with or subsequent to application or incorporation of the photochromic material. For example, ultraviolet light absorbers can be admixed with photochromic materials before their addition to the composition or such absorbers can be superposed, e.g., superimposed, as a coating between the photochromic article and the incident light.

Further, stabilizers can be admixed with the photochromic materials prior to their addition to the composition to improve the light fatigue resistance of the photochromic materials provided that such stabilizers do not prevent the photochromic materials from activating. Non-limiting examples of stabilizers include hindered amine light stabilizers (HALS), asymmetric diaryloxalamide (oxanilide) compounds and singlet oxygen quenchers, e.g., a nickel ion complex with an organic ligand, polyphenolic antioxidants or mixtures of such stabilizers are contemplated. In one non-limiting embodiment, they can be used alone or in combination. Such stabilizers are described in U.S. Pat. Nos. 4,720,356, 5,391,327 and 5,770,115.

The BWS photochromic materials, other photochromic materials or combinations thereof can be associated with the host material by various methods described in the art. In various non-limiting embodiments, the total amount of photochromic material can be incorporated into the host material used to form the photochromic article by various methods such as by adding the photochromic materials to one or more of the materials used to form the host material. In one non-limiting embodiment when the host material is a polymeric coating or film, the photochromic materials can be dissolved and/or dispersed in an aqueous or organic solvent prior to being incorporated into one or more of the components of the coating or film composition used to form the coating Alternatively, the photochromic materials can be incorporated into the at least partially cured coating or film by imbibition, permeation or other transfer methods as known by those skilled in the art.

When at least partially cured polymers or polymerizates are used as the host material for the photochromic materials, various non-limiting embodiments include preparation of a photochromic article by injecting a polymerizable composition with photochromic materials into a mold and polymerizing it by what, for example, is commonly referred to in the art as a cast-in-place process. Polymerizates, e.g., lenses, prepared by cast polymerization in the absence of a photochromic amount of a photochromic material can be used to prepare photochromic articles by applying or incorporating photochromic materials into the polymerizate by art-recognized methods.

Such non-limiting art-recognized methods include: (a) dissolving or dispersing the photochromic materials within the polymerizate, e.g., imbibition of the photochromic materials into the polymerizate by immersion of the polymerizate in a hot solution of the photochromic materials or by thermal transfer; (b) providing the photochromic material as a separate layer between adjacent layers of the polymerizate, e.g., as a part of a polymer film; and (c) applying the photochromic material as part of a coating or film placed or laminated on the surface of the polymerizate. The term "imbibition" or "imbibe" is intended to mean and include permeation of the photochromic materials individually or with other non-photochromic materials into the polymerizate, solvent assisted transfer absorption of the photochromic materials into a polymerizate, vapor phase transfer, and other such transfer mechanisms.

In the context of the present invention, the nature of the polymeric substrate, polymeric film or polymeric coating, collectively referred to as the polymeric host, can vary widely. Generally the polymeric host is such that it allows the BWS materials of the present invention and other photochromic materials to reversibly transform between their "open" and "closed" forms. In one non-limiting embodiment, the polymer and/or polymeric coating composition used to produce the photochromic articles of the present invention comprises compositions adapted to provide thermoplastic or thermosetting organic polymeric materials that are described in the *Kirk-Othmer Encyclopedia of Chemical Technology*, Fourth Edition, Volume 6, pages 669 to 760, which disclosure is incorporated herein by reference. Such polymeric host materials can be transparent, translucent or opaque; but desirably are transparent. In another non-limiting contemplated embodiment is a polymeric material that upon curing forms an at least partially cured polymeric coating chosen from polyurethanes, aminoplast resins, poly(meth)acrylates, e.g., polyacrylates and polymethacrylates, polyanhydrides, polyacrylamides, epoxy resins and polysilanes.

The various coating compositions described below are well known and are made with components and according to methods well understood and appreciated to those skilled in the art. Suitable substrates for the application of coatings containing the BWS materials or a mixture of the BWS materials and other photochromic materials include any type of substrate. Non-limiting examples include, paper, glass, ceramics, wood, masonry, textiles, metals and polymeric organic host materials.

The photochromic polyurethane coatings that can be used to prepare the photochromic coated articles of the present invention, in one non-limiting embodiment, can be produced by the catalyzed or uncatalyzed reaction of an organic polyol component and an isocyanate component in the presence of photochromic compound(s). Materials and methods for the preparation of polyurethanes are described in *Ullmann's Encyclopedia of Industrial Chemistry*, Fifth Edition, 1992, Vol. A21, pages 665 to 716. Non-limiting examples of methods and materials, e.g., organic polyols, isocyanates and other components, which can be used to prepare the polyurethane coating are disclosed in U.S. Pat. Nos. 4,889,413 and 6,187,444B1.

The photochromic aminoplast resin coating composition that can be used to produce the photochromic coated articles of the present invention, in one non-limiting embodiment, can be prepared by combining a photochromic material with the reaction product of a functional component(s) having at least two functional groups chosen from hydroxyl, carbamate, urea or a mixture thereof and an aminoplast resin, e.g., crosslinking agent as described in U.S. Pat. Nos. 4,756,973, 6,432,544B1 and 6,506,488.

Photochromic polysilane coating compositions contemplated for use in preparing the photochromic coated articles of the present invention, in one non-limiting embodiment, are prepared by hydrolyzing at least one silane monomer such as glycidoxypropyltrimethoxysilane, vinyltrimethoxysilane, methacryloxypropyltrimethoxysilane, tetramethoxysilane, tetraethoxysilane and/or methyltrimethoxysilane and combining the hydrolyzate with at least one photochromic material as described in U.S. Pat. No. 4,556,605.

Photochromic poly(meth)acrylate coating compositions contemplated for use in preparing the photochromic coated articles of the present invention can be prepared, in one non-limiting embodiment, by combining photochromic compound(s) with mono-, di- or multi-functional (meth) acrylates as described in U.S. Pat. Nos. 6,025,026 and 6,150,430 and WO publication 01/02449 A2.

The polyanhydride photochromic coating composition that can be used to prepare the photochromic coated articles of the present invention can be prepared in one non-limiting embodiment, by the reaction of a hydroxyl-functional component and a polymeric anhydride-functional component in a composition including at least one organic photochromic material as described in U.S. Pat. No. 6,432,544B1. Non-limiting examples of hydroxyl-functional components, anhydride-functional component(s) and other components that can be used to prepare the polyanhydride photochromic coatings are disclosed in U.S. Pat. Nos. 4,798,745, 4,798,746 and 5,239,012.

Photochromic polyacrylamide coating compositions contemplated for use in preparing the photochromic coated articles of the present invention, in one non-limiting embodiment, can be prepared by combining a photochromic component with the free radical initiated reaction product of a polymerizable ethylenically unsaturated composition comprising N-alkoxymethyl(meth)acrylamide and at least one other copolymerizable ethylenically unsaturated monomer as described in U.S. Pat. No. 6,060,001. Methods for preparing N-alkoxymethyl(meth)acrylamide functional polymer are described in U.S. Pat. No. 5,618,586.

The photochromic epoxy resin coating compositions that can be used to prepare the photochromic coated articles of the present invention, in one non-limiting embodiment, can be prepared by combining photochromic compound(s), epoxy resins or polyepoxides and curing agents as described in U.S. Pat. Nos. 4,756,973 and 6,268,055B1.

In another non-limiting embodiment, the types of photochromic polymeric coatings comprising the film-forming polymers and the BWS photochromic materials of the present invention with or without other photochromic compounds include paints, e.g., a pigmented liquid or paste used for the decoration, protection and/or the identification of a substrate; and inks, e.g., a pigmented liquid or paste used for writing and printing on substrates such as in producing verification marks on security documents, e.g., documents such as banknotes, passport and drivers' licenses, for which authentication or verification of authenticity may be desired.

Application of the polymeric coating can be by any of the methods used in coating technology, non-limiting examples include, spray coating, spin coating, spin and spray coating, spread coating, curtain coating, dip coating, casting or roll-coating and methods used in preparing overlays, such as the method of the type described in U.S. Pat. No. 4,873,029. The application method selected also depends on the thickness of the desired coating.

The thickness of the coatings on the photochromic articles of the present invention can vary widely. Coating having a thickness ranging from 1 to 50 microns can be applied by the methods used in coating technology. Coating of a thickness greater than 50 microns can require the application of multiple coatings or molding methods typically used for overlays. In one non-limiting embodiment, the coating may range in thickness from 1 to 10,000 microns, e.g., from 5 to 1000, e.g., from 8 to 400, e.g., from 10 to 250 microns. The thickness of the polymeric coating can range between any combination of these values, inclusive of the recited range, e.g., a thickness of from 20 to 200 microns.

Following application of the polymeric coating to the surface of the substrate, in one non-limiting embodiment, the coating is at least partially cured. In another non-limiting embodiment, the methods used for curing the photochromic polymeric coating include the methods used for forming an at least partially cured polymer. Such methods include radical polymerization, thermal polymerization, photopolymerization or a combination thereof. Additional non-limiting methods include irradiating the coated substrate or at least partially cured polymer with infrared, ultraviolet, gamma or electron radiation so as to initiate the polymerization reaction of the polymerizable components. This can be followed by a heating step.

In one non-limiting embodiment, if required and if appropriate, the surface of the substrate to be coated is cleaned prior to applying the photochromic polymeric coating to produce the photochromic article of the present invention. This can be done for the purposes of cleaning and/or promoting adhesion of the coating. Effective treatment techniques for plastics and glass are known to those skilled in the art.

In some non-limiting embodiments, it may be necessary to apply a primer to the surface of the substrate before application of the photochromic polymeric coating. The primer can serve as a barrier coating to prevent interaction of the coating ingredients with the substrate and vice versa, and/or as an adhesive layer to adhere the photochromic polymeric coating to the substrate. Application of the primer can be by any of the methods used in coating technology such as, for example, spray coating, spin coating, spin and spray coating, spread coating, dip coating, casting or roll-coating.

The use of protective coatings, some of which can contain polymer-forming organosilanes, as primers to improve adhesion of subsequently applied coatings has been described in U.S. Pat. No. 6,150,430, which disclosure is incorporated herein by reference. In one non-limiting embodiment, non-tintable coatings are used. Non-limiting examples of commercial coating products include SIL-VUE® 124 and HI-GARD® coatings, available from SDC Coatings, Inc. and PPG Industries, Inc., respectively. In addition, depending on the intended use of the coated article, in one non-limiting embodiment, it can be necessary to apply an appropriate protective coating(s), such as an abrasion resistant coating and/or coatings that can serve as oxygen barriers, onto the exposed surface of the coating composition to prevent scratches from the effects of friction and abrasion and interactions of oxygen with the photochromic materials, respectively.

In some cases, the primer and protective coatings are interchangeable, e.g., the same coating can be used as the primer and the protective coating(s). Non-limiting examples of hardcoats include those based on inorganic materials such as silica, titania and/or zirconia as well as organic hardcoats of the type that are ultraviolet light curable.

In one non-limiting embodiment, such protective coatings can be applied to the surface of photochromic articles comprising at least partially cured polymers containing photochromic materials.

In another non-limiting embodiment, the article of the present invention comprises a substrate to which a primer is applied followed by the photochromic polymeric coating and a protective hardcoat. In a further non-limiting embodiment, the protective hardcoat is an organosilane hardcoat.

In additional non-limiting embodiments, other coatings or surface treatments, e.g., a tintable coating, antireflective surface, etc., can also be, applied to the photochromic articles of the present invention. An antireflective coating, e.g., a monolayer or multilayer of metal oxides, metal fluorides, or other such materials, can be deposited onto the photochromic articles, e.g., lenses, of the present invention through vacuum evaporation, sputtering, or some other method.

In a further non-limiting embodiment, the photochromic article comprising an at least partially cured polymer and at least one BWS material with or without other photochromic material further comprises a superstrate, e.g., a film or sheet comprising at least one organic polymeric material. The photochromic material can be located in the superstrate, the at least partially cured polymer or both. The organic polymeric material of the superstrate is the same as the organic polymeric material described hereinafter as the substrate or host material. Non-limiting examples of the organic polymeric materials include thermosetting or thermoplastic materials, for example a thermoplastic polyurethane superstrate.

In a still further non-limiting embodiment, the superstrate can be connected to the polymer surface directly, but does not become thermally fused to the substrate. In another non-limiting embodiment, the superstrate can be adheringly bonded to the substrate by becoming thermally fused with the subsurface of the substrate. General conditions under which superstrates are adheringly bonded to a substrate are known to those skilled in the art. Non-limiting conditions for adheringly laminating a superstrate to a substrate include heating to a temperature of from 250–350° F. (121–177° C.) and applying pressure of from 150 to 400 pounds per square inch (psi) (1034 to 2758 kPa). Sub-atmospheric pressures, e.g., a vacuum, can also be applied to draw down and conform the superstrate to the shape of the substrate as known to those skilled in the art. Non-limiting examples include applying at a sub-atmospheric pressure within the range of from 0.001 mm Hg to 20 mm Hg (0.13 Pa to 2.7 kPa).

After a laminate comprising a superstrate applied to as least one surface of a substrate is formed, it can further comprise a protective coating or film superposed onto the superstrate. Such a protective coating or film, in one non-limiting embodiment, serves as an at least partially abrasion resistant coating or film. Non-limiting types of protective coatings include the aforedescribed hardcoats that are curable by ultraviolet radiation and/or that contain organosilanes. The thickness of the protective coating can vary widely and include the aforementioned range for the photochromic polymeric coatings. Non-limiting types of protective films include those made of organic polymeric materials such as thermosetting and thermoplastic materials. In another non-limiting embodiment, the protective film is a thermoplastic film made of polycarbonate. The thickness of the protective film or sheet can vary widely. Typically, such films have a thickness of from 1 to 20 mils (0.025 to 0.5 mm).

The host material for the BWS photochromic materials with or without other photochromic materials will usually be transparent, but may be translucent or even opaque. The host material need only be pervious to that portion of the electromagnetic spectrum, which activates the photochromic material, e.g., that wavelength of ultraviolet (UV) light that produces the open or colored form of the photochromic and that portion of the visible spectrum that includes the absorption maximum wavelength of the photochromic in its UV activated form, e.g., the open form. In one contemplated non-limiting embodiment, the host color should not be such that it masks the color of the activated form of the photochromic materials, e.g., so the change in color is readily apparent to the observer. Compatible tints may be applied to the host material as described in U.S. Pat. No. 5,645,767 in column 13, line 59 to column 14, line 3.

In one contemplated non-limiting embodiment, the polymeric organic host material can be a solid transparent or optically clear material, e.g., materials having a luminous transmittance of at least 70 percent and are suitable for optical applications, such as optical elements chosen from plano and ophthalmic lenses, ocular devices such as ophthalmic devices that physically reside in or on the eye, e.g., contact lenses and intraocular lenses, windows, automotive transparencies, e.g., windshields, aircraft transparencies, plastic sheeting, polymeric films, etc.

Non-limiting examples of polymeric organic materials which can be used as a host material for the BWS photochromic materials of the present invention with or without other photochromic materials or as a substrate for the photochromic polymeric coating include: poly(meth)acrylates, polyurethanes, polythiourethanes, thermoplastic polycarbonates, polyesters, poly(ethylene terephthalate), polystyrene, poly(alpha methylstyrene), copoly(styrene-methyl methacrylate), copoly(styrene-acrylonitrile), polyvinylbutyral, poly(vinyl acetate), cellulose acetate, cellulose propionate, cellulose butyrate, cellulose acetate butyrate, polystyrene or polymers, such as homopolymers and copolymers prepared by polymerizing monomers chosen from bis(allyl carbonate) monomers, styrene monomers, diisopropenyl benzene monomers, vinylbenzene monomers, e.g., those described in U.S. Pat. No. 5,475,074, diallylidene pentaerythritol monomers, polyol (allyl carbonate) monomers, e.g., diethylene glycol bis(allyl carbonate), vinyl acetate monomers, acrylonitrile monomers, mono- or polyfunctional, e.g., di- or multi-functional, (meth)acrylate monomers such as ($C_1$–$C_{12}$)alkyl (meth)acrylates, e.g., methyl (meth)acrylate, ethyl (meth)acrylate, butyl (meth)acrylate etc., poly(oxyalkylene)(meth)acrylate, poly(alkoxylated phenol (meth)acrylates), diethylene glycol (meth)acrylates, ethoxylated bisphenol A (meth)acrylates, ethylene glycol (meth)acrylates, poly(ethylene glycol) (meth)acrylates, ethoxylated phenol (meth)acrylates, alkoxylated polyhydric alcohol (meth)acrylates, e.g., ethoxylated trimethylol propane triacrylate monomers, urethane (meth)acrylate monomers, such as those described in U.S. Pat. No. 5,373,033, or a mixture thereof. Further examples of polymeric organic host materials are disclosed in the U.S. Pat. No. 5,753,146, column 8, line 62 to column 10, line 34.

In another non-limiting embodiment, transparent copolymers and blends of transparent polymers are also suitable as polymeric materials. The host material can be an optically clear polymerized organic material prepared from a thermoplastic polycarbonate resin, such as the carbonate-linked resin derived from bisphenol A and phosgene, which is sold under the trademark, LEXAN; a polyester, such as the material sold under the trademark, MYLAR; a poly(methyl methacrylate), such as the material sold under the trademark, PLEXIGLAS; polymerizates of a polyol(allyl carbonate) monomer, especially diethylene glycol bis(allyl carbonate), which monomer is sold under the trademark CR-39, and polymerizates of copolymers of a polyol (allyl carbonate), e.g., diethylene glycol bis(allyl carbonate), with other copolymerizable monomeric materials, and copolymers with a polyurethane having terminal diacrylate functionality, as described in U.S. Pat. Nos. 4,360,653 and 4,994,208; and copolymers with aliphatic urethanes, the terminal portion of which contain allyl or acrylyl functional groups, as described in U.S. Pat. No. 5,200,483.

A further non-limiting embodiment is use of the BWS materials of the present invention and other photochromic materials with optical organic resin monomers used to produce optically clear coatings, films and polymerizates, e.g., materials suitable for optical applications, such as for example plano and ophthalmic lenses, windows, and automotive transparencies. Examples of non-limiting embodiments include polymerizates of optical resins sold by PPG Industries, Inc. as TRIVEX monomers and under the CR-designation, e.g., CR-307, CR-407 and CR-607 and the resins used to prepare hard or soft contact lenses. Methods for producing both types of contact lenses are disclosed in U.S. Pat. No. 5,166,345, column 11, line 52, to column 12, line 52.

Further non-limiting embodiments of optical resins include the resins used to form soft contact lenses with high moisture content described in U.S. Pat. No. 5,965,630 and extended wear contact lenses described in U.S. Pat. No. 5,965,631.

The present invention is more particularly described in the following examples, which are intended as illustrative only, since numerous modifications and variations therein will be apparent to those skilled in the art.

The following photochromic materials (PM) were used in the examples described hereinafter. PM-C, PM-D, PM-L, PM-M and PM-N represent BWS materials PM-A, PM-B, PM-E, PM-F, PM-G, PM-H, PM-I, PM-J, PM-K, PM-O, PM-P, and PM-AA and PM-BB represent other photochromic materials.

| | |
|---|---|
| PM-A | 7,7-diphenyl-2-pentyl-4-oxo-4H-7H-[1,3]dioxino[5',4':3,4]naphtho[1,2-b]pyran |
| PM-B | 7-phenyl-7-(4-morpholinophenyl)-2-pentyl-4-oxo-4H-7H-[1,3]dioxino[5',4':3,4]naphtho[1,2-b]pyran |
| PM-C | 3,3-di(4-methoxyphenyl)-11-morpholino-13,13-dimethyl-13H-3H-indeno[2',3',3,4]naphtho[1,2-b]pyran |
| PM-D | 3-(4-morpholinophenyl)-3-phenyl-11-morpholino-13,13-dimethyl-13H-3H-indeno[2',3',3,4]naphtho[1,2-b]pyran |
| PM-E | 7-(2-fluorophenyl)-7-(3-methyl-4-methoxyphenyl)-2-pentyl-4-oxo-4H-7H-[1,3]dioxino[5',4':3,4]naphtho[1,2-b]pyran |
| PM-F | 3-(4-methoxyphenyl)-3-phenyl-10,11-dimethoxy-13,13-dimethyl-13H-3H-indeno[2',3',3,4]naphtho[1,2-b]pyran |
| PM-G | 2-(4-methoxyphenyl)-2-(2,4-dimethoxyphenyl)-7-diphenylmethyl-10-methyl-5-oxo-2H-5H-pyrano[3',4':3,4]naphtho[1,2-b]pyran |
| PM-H | 7-(4-methoxyphenyl)-7-(2,4-dimethoxyphenyl)-2-pentyl-4-oxo-4H-7H-[1,3]dioxino[5',4':3,4]naphtho[1,2-b]pyran |
| PM-I | 7-(4-morpholino-2-fluorophenyl)-7-(4-methoxyphenyl)-2-pentyl-4-oxo-4H-7H-[1,3]dioxino[5',4':3,4]naphtho[1,2-b]pyran |
| PM-J | 7-(2-fluoro-4-methoxyphenyl)-7-(4-morpholinophenyl)-2-pentyl-4-oxo-4H-7H-[1,3]dioxino[5',4':3,4]naphtho[1,2-b]pyran |
| PM-K | 7-(4-morpholino-2-fluorophenyl)-7-(3,4-dimethoxyphenyl)-2-pentyl-4-oxo-4H-7H-[1,3]dioxino[5',4':3,4]naphtho[1,2-b]pyran |
| PM-L | 3-(3,4-dimethoxyphenyl)-3-(4-methoxyphenyl)-11-morpholino-13,13-dimethyl-13H-3H-indeno[2',3',3,4]naphtho[1,2-b]pyran |
| PM-M | 3,3-di(2-methoxyethoxyphenyl)-11-morpholino-13,13-dimethyl-13H-3H-indeno[2',3',3,4]naphtho[1,2-b]pyran |
| PM-N | 3-(4-methoxyphenyl)-3-(4-morpholinophenyl)-11-morpholino-13,13-dimethyl-13H-3H-indeno[2',3',3,4]naphtho[1,2-b]pyran |
| PM-O | 3,3-di(4-methoxyphenyl)-6,11-dimethoxy-13-butyl-13-ethoxy-13H-3H-indeno[2',3',3,4]naphtho[1,2-b]pyran |
| PM-P | 3,3-di(4-methoxyphenyl)-10,11-dimethoxy-13,13-dimethyl-13H-3H-indeno[2',3',3,4]naphtho[1,2-b]pyran |

-continued

| | |
|---|---|
| PM-AA | A naphtho[1,2-b]pyran that exhibits a purple color when irradiated with ultraviolet light. |
| PM-BB | A naphtho[1,2-b]pyran that exhibits a yellow-green color when irradiated with ultraviolet light. |

EXAMPLE 1

The following materials were added in the order and the manner described to a container suitable for use with a BRINKMAN PT-3000 homogenized:

| Charge 1 | |
|---|---|
| Material | Weight (grams) |
| 2-Ethoxyethyl ether | 50.0 |
| Tetrahydrofurfuryl alcohol | 30.0 |
| m-Methyl pyrrolidone | 20.0 |
| Hydroxylpropyl cellulose | 12.0 |
| Silica | 0.9 |

| Charge 2 | |
|---|---|
| Material | Weight Percent |
| PM-D/PM-E/PM-B in 45/45/10 weight ratio | 1.65 |
| TINUVIN ® 144 UV Stabilizer[1] | 0.83 |

[1]Hindered amine ultraviolet light stabilizer available from CIBA Specialty Chemicals Charge 1 was added to the container and mixed by the homogenizer at a speed of 5000 rpm for 2 minutes or until the materials were dissolved. Charge 2 was added to the container and the resulting mixture was heated while mixing until the materials dissolved.

EXAMPLE 2

The procedure of Example 1 was followed except that in Charge 2 the following combination of photochromic materials was used: PM-A/PM-C/PM-D/PM-E/PM-G/PM-P in a weight ratio of 15/15/15/5/40/10.

EXAMPLE 3

The procedure of Example 1 was followed except that in Charge 2 the following combination of photochromic materials was used: PM-A/PM-B/PM-C/PM-D/PM-H in a weight ratio of 10/20/20/30/20.

EXAMPLE 4

The procedure of Example 1 was followed except that in Charge 2 the following combination of photochromic materials was used: PM-A/PM-C/PM-I in a weight ratio of 25/45/30.

EXAMPLE 5

The procedure of Example 1 was followed except that in Charge 2 the following combination of photochromic materials was used: PM-A/PM-C/PM-D/PM-E/PM-F in a weight ratio of 10/15/25/15/20.

EXAMPLE 6

The procedure of Example 1 was followed except that in Charge 2 the following combination of photochromic materials was used: PM-A/PM-C/PM-D/PM-I/PM-J in a weight ratio of 30/24/20/13/13.

EXAMPLE 7

The procedure of Example 1 was followed except that in Charge 2 the following photochromic material was used: PM-L.

EXAMPLE 8

The procedure of Example 1 was followed except that in Charge 2 the following photochromic material was used: PM-K.

EXAMPLE 9

The procedure of Example 1 was followed except that in Charge 2 the following combination of photochromic materials: PM-A/PM-C/PM-K/PM-AA/PM-BB in a weight ratio of 24/45/25/2/4 and 0.033 percent by weight, based on the total weight of Charges 1 and 2, of D&C Violet #2 (CAS #81-48-1) were used.

EXAMPLE 10

The procedure of Example 1 was followed except that in Charge 2 the following photochromic material was used: PM-M.

EXAMPLE 11

The procedure of Example 1 was followed except that in Charge 2 the following photochromic material was used: PM-N.

EXAMPLE 12

The procedure of Example 1 was followed except that in Charge 2 the following combination of photochromic materials was used: PM-A/PM-C/PM-I/PM-O/PM-AA/PM-BB in a weight ratio of 24/42/25/3/2/4.

COMPARATIVE EXAMPLE 1

The weight of the paper representing the area beneath the absorption spectrum for Dye A in FIG. 1 of U.S. Pat. No. 6,102,543 was determined as follows. FIG. 1 was enlarged 200 percent on a photocopier. The 410 nm point on the horizontal axis was established by determining that 100 nm equaled 39 mm and by marking the axis about 3.9 mm to the right of the 400 nm point. The area on the enlarged figure beneath the spectrum from 380 nm to 700 nm was cut out and weighed on a Mettler XA1200 balance. This was the total area weight. The area on the enlarged figure beneath the spectrum from 410 nm to 700 nm was cutout and weighed. This corresponded to the visible area weight. The weight of the area beneath the spectrum from 380 to 410 nm was determined by subtracting the visible area weight from the total area weight. The area weight percent of the spectrum in the visible region was calculated by dividing the visible area weight by the total area weight and multiplying by 100. The area weight percent of the spectrum in the ultraviolet region was calculated by dividing the ultraviolet area weight by the total area weight and multiplying by 100. The results are listed in Table 3.

COMPARATIVE EXAMPLE 2

The procedure of Comparative Example 1 was followed except that the weight of the paper representing the area beneath the absorption spectrum for Dye B in FIG. 1 of U.S. Pat. No. 6,102,543 was determined.

COMPARATIVE EXAMPLE 3

The procedure of Comparative Example 1 was followed except that the weight of the paper representing the area beneath the absorption spectrum for Dye C in FIG. 1 of U.S. Pat. No. 6,102,543 was determined.

COMPARATIVE EXAMPLES 4–8

The commercially available plastic lenses described and listed below were used as Comparative Examples (CE). Each lens was a plano type lens that reportedly activated to a grey or brown color as indicated. Each lens was tested in duplicate and the average of the result was reported hereinafter in Table 1.

| CE # | Lens Description | Thickness |
|---|---|---|
| 4A | Corning SunSensors ® (grey) | 1.8 mm |
| 4B | Corning SunSensors ® (brown) | 1.8 mm |
| 5A | Hoya Hilux ® (grey) | 2.0 mm |
| 5B | Hoya Hilux ® (brown) | 2.0 mm |
| 6A | Transitions ® Next Generations (grey) | 2.0 mm |
| 6B | Transitions ® Next Generations (brown) | 2.0 mm |
| 7A | Rodenstock ® ColorMatic Extra (grey) | 1.9 mm |
| 7B | Rodenstock ® ColorMatic Extra (brown) | 1.9 mm |
| 8A | Transitions ® III 1.50 (grey) | 2.0 mm |
| 8B | Transitions ® III 1.50 (brown) | 2.0 mm |

EXAMPLE 13

The Behind the Windshield Test and the Outdoor Test are described herein. The preparation of samples is described in Part A, testing of photochromic performance is described in Part B, testing of percent transmission is described in Part C and the spectra of representative BWS photochromic materials compared to Comparative Examples 1–3 is described in Part D.

Part A

Testing of Examples 1–12 was done with test samples prepared using CR-607® monomer available from PPG Industries, Inc., with the addition of 0.02 weight percent Cyasorb® UV 5411, an ultraviolet light absorber from CIBA Specialty Chemicals Corp. and 2.5 parts per hundred of resin (pph) of diisopropyl peroxydicarbonate, a thermal initiator. The initiator and UV absorber were dissolved in the monomer by mixing and then the monomer was poured into molds measuring 12 inches by 12 inches by 0.08 inches (30.5 centimeters by 30.5 centimeters by 0.2 centimeters). The molds were cured according to the following cycle. Hold for 6 hours at 36° C.; ramp up to 56° C. over 8 hours; after 2.0 hours at 56° C., ramp up to 72° C.; after 8 hours, at 72° C. remove sample and cool to 60° C. and demold.

Afterwards, the cured sheets were cut into two inch by two inch squares (5.08 centimeters by 5.08 centimeters). The test squares were washed with dishwashing detergent and water, rinsed with deionized water and wiped with an acetone soaked tissue prior to the application of the example solutions. The imbibition coating was applied to the test samples by dispensing a quantity of imbibition coating on the test sample and spinning at about 1500 rpm for about four seconds to produce a wet film-weight of 0.35 to 0.40 milligrams per lens. The resulting films were dried under an infrared light for about 20 minutes and placed in an oven at 135–140° C. for the times indicated in the following table. Afterward, the imbibed test samples were washed with soap and rinsed with water.

| Example # | Time |
|---|---|
| 1, 2 and 5 | 4 hours |
| 3, 4, and 6–12 | 8 hours |

Part B

The photochromic imbibed test squares prepared in Part A were tested for photochromic response in the Outdoor Test and the Behind the Windshield Test as described herein on a Bench for Measuring Photochromics (BMP) optical bench made by Essilor, France.

The Behind the Windshield Test was used to determine the change in optical density ($\Delta OD$) obtained by the sample when tested under conditions simulating photochromic lens response on a wearer inside an automobile. It was determined that the amount of light energy available to activate a photochromic lens on a wearer in an automobile was 0.75 Watts/m$^2$ integrated between 380 and 420 nm and 1.7 Klux (kilolumens/m$^2$) whereas, the amount of energy available in the Outdoor Test was 6.7 Watts/m$^2$ (UVA) integrated between 315 and 380 nm and 50 Klux. The Outdoor Test was used to determine the change in optical density obtained by the sample when tested under conditions simulating photochromic lens response on a wearer outdoors.

Prior to testing on the optical bench, the photochromic test squares were conditioned by activating and fading as described hereinafter. The test squares were first exposed to 365 nanometer ultraviolet light for about 10 minutes at a distance of about 14 centimeters to activate the photochromic compounds. The UVA (315 to 380 nm) irradiance at the sample was measured with a Licor Model Li-1800 spectroradiometer and found to be 22.2 watts per square meter. The activated samples were then placed under a 500 watt, high intensity halogen lamp for about 10 minutes at a distance of about 36 centimeters to bleach or inactivate the photochromic compounds. The illuminance at the sample was measured with the Licor spectroradiometer and found to be 21.4 Klux. The test squares were then kept covered for at least 1 hour prior to testing on an optical bench.

The BMP optical bench was fitted with two 150 watt Xenon arc lamps. The light path from Lamp 1 was directed through a 3 mm Schott KG-2 band-pass filter and appropriate neutral density filters that contributed to the required UV and partial visible light irradiance level. The light path from the Lamp 2 was directed through a 3 mm Schott KG-2 band-pass filter, a 400 nm cutoff filter and neutral density filters in order to provide supplemental visible light illuminance. For the outdoor test conditions, both lamps were used, but for the in automobile simulation, only Lamp 1 with a direct irradiance path to the sample was used. In this irradiance path, the 3 mm Schott KG-2 band-pass filter and a simulated windshield typical of an auto windshield were used to control the irradiance spectral profile. Neutral density filters and voltage control of the Xenon arc lamp were used to adjust the intensity of the light.

The irradiance used for the Behind the Windshield Test was determined to be an average radiant flux integrated between 380 and 420 nm of 0.75 Watts/m$^2$ with 1.7 Klux of visible light. The samples were controlled at a temperature of 28° C. The outdoor simulated conditions were an irradiance level of 6.7 Watts/m$^2$ UVA, 50 Klux and controlled at a temperature of 23° C. The simulated windshield was prepared by laminating a 0.73 mm thick piece of polyvinylbutyrate film from Solutia Inc. between two 2.3 mm thick layers of Solex 97 glass from PPG Industries, Inc. The simulated windshield had a total thickness of 5.33 mm. A spectra of the light passing through the simulated windshield as measured on the BMP is shown in FIG. 1.

Proprietary software was used on the BMP to control timing, irradiance, air cell and sample temperature, shuttering, filter selection and response measurement. A Zeiss spectrophotometer, Model MCS 501, with fiber optic cables for light delivery through the sample was used for response and color measurement. For single photochromic systems, response measurements were collected at the visible lambda max. Photopic response measurements were collected when testing multiple photochromic lens systems.

Response measurements, in terms of change in optical density ($\Delta OD$) from the unactivated state to the activated or darkened state were determined by establishing the initial unactivated transmittance, opening the shutter from the Xenon lamp(s) and measuring the transmittance during activation of the sample at selected intervals of time. Change in optical density was determined according to the formula: $\Delta OD = \log(\%\, Tb/\%\, Ta)$, where % Tb is the percent transmittance in the bleached state, % Ta is the percent transmittance in the activated state and the logarithm is to the base 10. Optical density measurement can be per specific wavelength or photopic.

The Percent of the $\Delta OD$ retained by the test samples was determined by measuring the change in optical density ($\Delta OD$) from the bleached to the darkened state under conditions corresponding to outdoor simulation (OS) and behind the windshield (BWS) eyeglass wearer simulation. The examples of the present invention and comparative examples were activated until saturated which was 15 minutes for the examples of the present invention and 30 minutes for the comparative examples. The measure used was the percent of $\Delta OD$ retained between the two conditions according to the following formula:

$$\%\, \Delta OD \text{ Retained} = 100 \times (\Delta OD_{BWS}/\Delta OD_{OS}).$$

Results for Examples 1–12 are in Table 1 and the results for Comparative Examples 4A/4B to 8A/8B are in Table 1A.

TABLE 1

| Example # | ΔOD @ 15 min. (OS) 23° C. | ΔOD @ 15 min. (BWS) 28° C. | % ΔOD Retained |
|---|---|---|---|
| 1 | 1.118 | 0.313 | 28 |
| 2 | 0.855 | 0.223 | 26 |
| 3 | 1.096 | 0.289 | 26 |
| 4 | 0.952 | 0.217 | 23 |
| 5 | 1.351 | 0.355 | 26 |
| 6 | 1.026 | 0.237 | 23 |
| 7 | 1.497 | 0.394 | 26 |
| 8 | 1.410 | 0.192 | 14 |
| 9 | 0.870 | 0.193 | 22 |
| 10 | 1.675 | 0.420 | 25 |
| 11 | 1.542 | 0.293 | 19 |
| 12 | 1.000 | 0.261 | 26 |

TABLE 1A

| Example # | ΔOD @ 30 min. (OS) 23° C. | ΔOD @ 30 min. (BWS) 28° C. | % ΔOD Retained |
|---|---|---|---|
| CE-4A | 0.545 | 0.008 | 1.5 |
| CE-4B | 0.566 | 0.019 | 3.4 |
| CE-5A | 0.537 | 0.056 | 10 |
| CE-5B | 0.478 | 0.054 | 11 |
| CE-6A | 0.786 | 0.080 | 10 |
| CE-6B | 0.727 | 0.075 | 10 |
| CE-7A | 0.583 | 0.043 | 7.4 |
| CE-7B | 0.484 | 0.036 | 7.4 |
| CE-8A | 0.576 | 0.040 | 6.9 |
| CE-8B | 0.484 | 0.040 | 8.3 |

The results of Table 1 show that Examples 1–12, when der behind the windshield eyeglass wearer simulating conditions, retained from 14 to 28 percent of the ΔOD measured under outdoor simulating conditions, whereas in Table 1A, Comparative Examples 4A/B to 8A/B retained less than 12 percent of the ΔOD measured under outdoor simulating conditions.

Part C

The photochromic test squares from Part A were conditioned by activating and fading as described in Part B amd were tested for the percent transmission through the sample unactivated bleached state under the outdoor simulating (OS) condition of 23° C. and when activated under the behind the windshield (BWS) eyeglass wearers simulating conditions at 28° C. Testing was done using the BMP as described in Part B. The results are listed in Table 2.

TABLE 2

| Example # | Bleached State % Transmission (OS) 23° C. | Activated State % Transmission (BWS) 28° C. |
|---|---|---|
| 1 | 82 | 39 |
| 2 | 86 | 52 |
| 3 | 84 | 44 |
| 4 | 82 | 44 |
| 5 | 85 | 39 |
| 6 | 82 | 48 |
| 7 | 84 | 45 |
| 8 | 77 | 59 |
| 9 | 76 | 49 |
| 10 | 86 | 44 |
| 11 | 85 | 55 |
| 12 | 85 | 47 |
| CE4A | 85 | 83 |
| CE4B | 85 | 82 |
| CE5A | 87 | 76 |
| CE5B | 86 | 76 |
| CE6A | 89 | 74 |
| CE6B | 89 | 75 |
| CE7A | 86 | 77 |
| CE7B | 85 | 78 |
| CE8A | 87 | 79 |
| CE8B | 88 | 80 |

The results of Table 2 show that Examples 1–12 demonstrate an activated state luminous transmission at saturation of less than 60 percent. Comparative Examples 4A/4B to 8A/8B demonstrated an activated state luminous transmission at saturation of greater than 60 percent.

Part D

The spectrum for each of Photochromic Materials: PM-A; PM-C; PM-D; PM-E; PM-F; PM-I and PM-J was prepared by dissolving enough of each photochromic material into a cuvette containing diethylene glycol dimethyl ether to result in a maximum absorbance of less than 1.0 as measured on a Cary Ultraviolet/Visible spectrophotometer, Model #3. The figure of absorbance versus wavelength for each photochromic material was printed at 100 percent. The 410 nm point on the horizontal axis was established by determining that 20 nm equaled 6.0 mm and by marking the graph 3.0 mm to the right of 400 nm. The paper representing the area beneath the spectrum from 380 to 700 nm was cutout and weighed on a Mettler XA1200 balance. This was the total area weight. The paper representing the area beneath the spectrum between 380 and 410 nm was cutout and weighed. This corresponded to the UV area weight. The weight of the area beneath the spectrum from 410 to 700 nm was determined by subtracting the ultraviolet area weight from the total area weight. The area weight percent of the spectrum in the UV region and visible region was calculated as done hereinbefore in Comparative Example 1. The results are listed in Table 3.

TABLE 3

| Spectra | TOTAL Area from 380–700 nm Weight (mg) | UV Area from 380–410 nm Weight (mg) | VISIBLE Area from 410–700 nm Weight (mg) | Weight % of UV Area of TOTAL Area | Weight % of VISIBLE Area of TOTAL Area |
|---|---|---|---|---|---|
| PM-A | 30.2 | 27.7 | 2.5 | 92 | 8 |
| PM-C | 35.4 | 26.7 | 8.7 | 75 | 25 |
| PM-D | 35.4 | 25.2 | 10.2 | 71 | 29 |
| PM-E | 29.5 | 23.1 | 6.4 | 78 | 22 |
| PM-F | 28.5 | 23.0 | 5.5 | 81 | 19 |
| PM-I | 27.4 | 23.0 | 4.4 | 84 | 16 |
| PM-J | 29.3 | 24.5 | 4.8 | 84 | 16 |
| PM-K | 28.6 | 22.8 | 5.8 | 80 | 20 |
| CE-1 | 16.1 | 4.6 | 11.5 | 29 | 71 |
| CE-2 | 27.1 | 7.1 | 20.0 | 26 | 74 |
| CE-3 | 71.0 | 6.6 | 64.4 | 9 | 91 |

The results of Table 3 show that each of the spectra of Photochromic Materials A, C, D, E, F, I, J and K had substantially more area in the 380 to 410 nm ultraviolet wavelength range, than in the 410 to 700 nm visible wavelength range. The results for the Comparative Examples 1 through 3 showed substantially more area in the 410 to 700 nm visible wavelength range than in the 380 to 410 nm ultraviolet wavelength range.

The present invention has been described with reference to specific details of particular embodiments thereof. It is not intended that such details be regarded as limitations upon the scope of the invention except insofar as to the extent that they are included in the accompanying claims.

We claim:

1. A photochromic article comprising:
   a) a substrate; and
   b) a photochromic amount of at least one organic photochromic material (b) adapted to change from an unactivated form to an activated form by exposure to radiation substantially in the wavelength range from 380 to 410 nanometers when measured over a range of from 380 to 700 nanometers, said photochromic article being adapted to retain at least 12 percent of the delta OD measured in the Outdoor Test when tested in the Behind the Windshield Test, said photochromic material (b) being represented by the following graphic formula XIII:

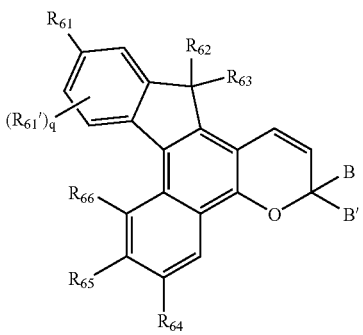

XIII wherein, (aa) $R_{61}$ is represented by:
  (i) —$SR_{67}$, $R_{67}$ being chosen from $C_1$–$C_6$ alkyl, aryl, mono- or di-substituted aryl, said aryl group being phenyl or naphthyl and each of said aryl substituents being chosen independently from $C_1$–$C_6$ alkyl, $C_1$–$C_6$ alkoxy or halogen; or
  (ii) an amino group chosen from:
    (1) —$N(R_{16})R_{17}$, $R_{16}$ and $R_{17}$ each being independently chosen from hydrogen, $C_1$–$C_8$ alkyl, aryl, furanyl, benzofuran-2-yl, benzofuran-3-yl, thienyl, benzothien-2-yl, benzothien-3-yl, dibenzofuranyl, dibenzothienyl, benzopyridyl, fluorenyl, $C_1$–$C_8$ alkylaryl, $C_3$–$C_{20}$ cycloalkyl, $C_4$–$C_{20}$ bicycloalkyl, $C_5$–$C_{20}$ tricycloalkyl or $C_1$–$C_{20}$ alkoxyalkyl and said aryl group being phenyl or naphthyl;
    (2) a nitrogen containing ring represented by the following graphic formula:

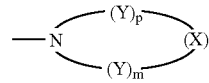

wherein each Y being independently chosen for each occurrence from —$CH_2$—, —$CH(R_{26})$—, —$C(R_{26})(R_{26})$—, —$CH(aryl)$—, —$C(aryl)_2$— or —$C(R_{26})(aryl)$—; X being —Y—, —O—, —S—, —S(O)—, —$S(O_2)$—, —NH—, —$N(R_{26})$— or —$N(aryl)$—; $R_{26}$ being $C_1$–$C_6$ alkyl; said aryl group being phenyl or naphthyl, m being chosen from the integer 1, 2 or 3 and p being chosen from the integer 0, 1, 2 or 3; provided that when p is 0, X is Y;
    (3) a group represented by one of the following graphic formulae:

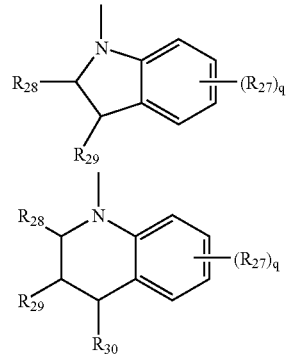

wherein each $R_{28}$, $R_{29}$ and $R_{30}$ being chosen independently for each occurrence in each formula from hydrogen, $C_1$–$C_5$ alkyl, phenyl or naphthyl; or the groups $R_{28}$ and $R_{29}$ together form a ring of 5 to 8 carbon atoms; $R_{27}$ being chosen independently for each occurrence from $C_1$–$C_6$ alkyl, $C_1$–$C_6$ alkoxy, fluoro or chloro and q being chosen from the integer 0, 1 or 2;
    (4) unsubstituted, mono- or di-substituted $C_4$–$C_{18}$ spirobicyclic amine; and
    (5) unsubstituted, mono- or di-substituted $C_4$–$C_{18}$ spirotricyclic amine; said substituents for (4) and (5) being independently chosen for each occurrence from aryl, $C_1$–$C_6$ alkyl, $C_1$–$C_6$ alkoxy or phenyl ($C_1$–$C_6$)alkyl;
(bb) $R_{61}'$ is independently chosen for each occurrence from $C_1$–$C_6$ alkyl or $C_1$–$C_6$ alkoxy and q being chosen from the integer 0, 1 or 2;
(cc) $R_{62}$ and $R_{63}$ are each independently chosen from:
  (i) hydrogen, hydroxy, amino, mono- or di-substituted amino, $C_1$–$C_{12}$ alkyl, $C_3$–$C_{12}$ alkylidene, $C_2$–$C_{12}$ alkylidyne, vinyl, $C_3$–$C_7$ cycloalkyl, $C_1$–$C_6$ alkoxyalkyl, allyl, benzyl, mono-substituted benzyl, chloro, fluoro or —C(O)W″, wherein W″ being hydroxy, $C_1$–$C_6$ alkyl, $C_1$–$C_6$ alkoxy, phenyl, mono-substituted phenyl, amino, mono($C_1$–$C_6$)alkylamino, di($C_1$–$C_6$)alkylamino, morpholino, piperidino or pyrrolidyl; said amino substituents in (cc)(i) being $C_1$–$C_6$ alkyl, phenyl, benzyl or naphthyl; each of said benzyl substituents being $C_1$–$C_6$ alkyl or $C_1$–$C_6$ alkoxy;

(ii) an unsubstituted, mono- di- or tri-substituted group chosen from phenyl, naphthyl, phenanthryl, pyrenyl, quinolyl, isoquinolyl, benzofuranyl, thienyl, benzothienyl, dibenzofuranyl, dibenzothienyl, carbazolyl or indolyl; each of said group substituents in (cc)(ii) being chosen independently for each occurrence from chloro, fluoro, $C_1$–$C_6$ alkyl or $C_1$–$C_6$ alkoxy;

(iii) a monosubstituted phenyl, said phenyl having a substituent located at the para position being —($CH_2$)$_r$— or —O—($CH_2$)$_r$—, wherein r being chosen from the integer 1, 2, 3, 4, 5 or 6, said substituent being connected to an aryl group which is a member of another photochromic material;

(iv) —OR$_{67'}$, R$_{67'}$ being chosen from $C_1$–$C_6$ alkyl, $C_1$–$C_6$ acyl, phenyl($C_1$–$C_3$)alkyl, mono($C_1$–$C_6$)alkyl substituted pheny($C_1$–$C_3$)alkyl, mono($C_1$–$C_6$)alkoxy substituted phenyl($C_1$–$C_3$)alkyl, $C_1$–$C_6$ alkoxy ($C_2$–$C_6$)alkyl, $C_3$–$C_7$ cycloalkyl, mono($C_1$–$C_4$)alkyl substituted $C_3$–$C_7$ cycloalkyl, $C_1$–$C_6$ chloroalkyl, $C_1$–$C_6$ fluoroalkyl, allyl, triarylsilyl, triarysilyloxy, tri($C_1$–$C_{C6}$)alkylsilyl, tri($C_1$–$C_{C6}$)alkylsilyloxy, tri($C_1$–$C_6$)alkoxysilyl, tri($C_1$–$C_6$)alkoxysilyloxy, di($C_1$–$C_6$)alkyl($C_1$–$C_6$ alkoxy)silyl, di($C_1$–$C_6$)alkyl ($C_1$–$C_6$ alkoxy)silyloxy, di($C_1$–$C_6$)alkoxy($C_1$–$C_6$ alkyl)silyl, di($C_1$–$C_6$)alkoxy($C_1$–$C_6$ alkyl)silyloxy, benzoyl, mono-substituted benzoyl, naphthoyl or mono-substituted naphthoyl; each of said benzoyl and naphthoyl substituents being independently chosen from $C_1$–$C_6$ alkyl or $C_1$–$C_6$ alkoxy; or R$_{67'}$ being —CH(R$_{68}$)Q″, wherein R$_{68}$ being chosen from hydrogen or $C_1$–$C_3$ alkyl and Q″ being chosen from —CN, —CF$_3$, or COOR$_{68}$; R$_{67'}$ being —C(O)V″, wherein V″ being chosen from hydrogen, $C_1$–$C_6$ alkoxy, phenoxy, mono- or di-($C_1$–$C_6$)alkyl substituted phenoxy, mono- or di-($C_1$–$C_6$)alkoxy substituted phenoxy, an unsubstituted, mono- or di-substituted aryl group phenyl or naphthyl, amino, mono ($C_1$–$C_6$)alkylamino, di($C_1$–$C_6$)alkylamino, phenylamino, mono- or di-($C_1$–$C_6$)alkyl substituted phenylamino, or mono- or di-($C_1$–$C_6$)alkoxy substituted phenylamino; each of said aryl group substituents being independently chosen from $C_1$–$C_6$ alkyl or $C_1$–$C_6$ alkoxy;

(v) —CH(Q‴)$_2$, Q‴ being chosen from —CN or —COOR$_{69}$ and R$_{69}$ being chosen from hydrogen, $C_1$–$C_6$ alkyl, phenyl($C_1$–$C_3$)alkyl, mono($C_1$–$C_6$) alkyl substituted phenyl($C_1$–$C_3$)alkyl, mono($C_1$–$C_6$) alkoxy substituted phenyl($C_1$–$C_3$)alkyl or an unsubstituted, mono- or di-substituted aryl group, phenyl or naphthyl; each of said aryl group substituents being independently chosen from $C_1$–$C_6$ alkyl or $C_1$–$C_6$ alkoxy;

(vi) —CH(R$_{70}$)G″, R$_{70}$ being chosen from hydrogen, $C_1$–$C_6$ alkyl or an unsubstituted, mono- or di-substituted aryl group, phenyl or naphthyl, and G″ being chosen from —COOR$_{69}$, —COR$_{71}$ or —CH$_2$OR$_{72}$, wherein R$_{71}$ being chosen from hydrogen, $C_1$–$C_6$ alkyl, an unsubstituted, mono- or di-substituted aryl group, phenyl or naphthyl, amino, mono($C_1$–$C_6$) alkylamino, di($C_1$–$C_6$)alkylamino, phenylamino, mono- or di-($C_1$–$C_6$)alkyl substituted phenylamino, mono- or di-($C_1$–$C_6$)alkoxy substituted phenylamino, diphenylamino, mono- or di-($C_1$–$C_6$)alkyl substituted diphenylamino, mono- or di-($C_1$–$C_6$) alkoxy substituted diphenylamino, morpholino or piperidino; R$_{72}$ being chosen from hydrogen, —C(O)R$_{69}$, $C_1$–$C_6$ alkyl, $C_1$–$C_3$ alkoxy($C_1$–$C_6$) alkyl, phenyl($C_1$–$C_3$)alkyl, mono($C_1$–$C_6$)alkoxy substituted phenyl($C_1$–$C_3$)alkyl or an unsubstituted, mono- or di-substituted aryl group, phenyl or naphthyl, each of said aryl group substituents being independently chosen from $C_1$–$C_6$ alkyl or $C_1$–$C_6$ alkoxy;

(vii) the group T wherein the group T is represented by the formula:

-G[(OC$_2$H$_4$)$_x$(OC$_3$H$_6$)$_y$(OC$_4$H$_8$)$_z$]G'

—[(OC$_2$H$_4$)$_x$(OC$_3$H$_6$)$_y$(OC$_4$H$_8$)$_z$]G' wherein -G being chosen from —C(O)— or —CH$_2$—, G' being chosen from $C_1$–$C_3$ alkoxy or a polymerizable group, x, y and z each being independently chosen from a number between 0 and 50, and the sum of x, y and z being between 2 and 50; or (viii) R$_{62}$ and R$_{63}$ together form an oxo group or a substituted or unsubstituted spiro-carbocyclic ring containing 3 to 6 carbon atoms or a substituted or unsubstituted spiro-heterocyclic group containing 1 or 2 oxygen atoms and 3 to 6 carbon atoms including the spirocarbon atom, said spiro-carbocyclic ring and spiro-heterocyclic group being annellated with 0, 1 or 2 benzene rings, said substituents being hydrogen or $C_1$–$C_6$ alkyl;

(dd) R$_{64}$ is hydrogen or $C_1$–$C_6$ alkyl;

(ee) R$_{65}$ is hydrogen or $C_1$–$C_6$ alkyl;

(ff) R$_{66}$ is chosen from hydrogen, $C_1$–$C_6$ alkyl or the group R$_a$ chosen from:

(i) —OR$_{73}$, R$_{73}$ being chosen from phenyl($C_1$–$C_3$) alkyl, $C_1$–$C_6$ alkyl, mono($C_1$–$C_6$)alkyl substituted phenyl($C_1$–$C_3$)alkyl, mono($C_1$–$C_6$)alkoxy substituted phenyl($C_1$–$C_3$)alkyl, $C_1$–$C_6$ alkoxy($C_2$–$C_4$) alkyl, $C_3$–$C_7$ cycloalkyl, mono($C_1$–$C_4$)alkyl substituted $C_3$–$C_7$ cycloalkyl, $C_1$–$C_6$ chloroalkyl, $C_1$–$C_6$ fluoroalkyl, allyl or —CH(R$_{68}$)Q″ described in (cc) (i); or (ii) an amino group being the same described hereinbefore in (aa)(ii);

and (gg) B and B' are each independently chosen from (i) mono-T-substituted phenyl, wherein the group T is the same as described hereinbefore in (cc)(vii);

(ii) an unsubstituted, mono-, di-, or tri-substituted aryl group, phenyl or naphthyl;

(iii) 9-julolidinyl or the unsubstituted, mono- or di-substituted heteroaromatic group chosen from pyridyl furanyl, benzofuran-2yl, benzofuran-3yl, thienyl, benzothien-2yl, benzothien-3yl, dibenzofuranyl, dibenzothienyl, carbazoyl, benzopyridyl, indolinyl or fluorenyl, each of said aryl and heteroaromatic substituents in (hh)(ii) and (iii) being independently chosen from hydroxy, —C(O)U, wherein U being hydroxy, $C_1$–$C_6$ alkyl, $C_1$–$C_6$ alkoxy, phenyl, mono-substituted phenyl, amino, mono ($C_1$–$C_6$)alkylamino, di-($C_1$–$C_6$)alkyklamino, morpholino, piperidino or pyrrolidyl; aryl, mono ($C_1$–$C_6$)alkoxyaryl, di($C_1$$C_6$)alkoxyaryl, mono ($C_1$–$C_6$)alkylaryl, di($C_1$–$C_6$)alkylaryl, chloroaryl, fluoroaryl, $C_3$–$C_7$ cycloalkylaryl, $C_3$–$C_7$ cycloalkyl, $C_3$–$C_7$ cycloalkyloxy, $C_3$–$C_7$ cycloalkyloxy($C_1$–$C_6$) alkyl, $C_3$–$C_7$ cycloalkyloxy($C_1$–$C_6$)alkoxy, aryl ($C_1$–$C_6$)alkyl, aryl($C_1$–$C_6$)alkoxy, aryloxy, aryloxy ($C_1$–$C_6$)alkyl, aryloxy($C_1$–$C_6$)alkoxy, mono- or di- ($C_1$–$C_6$)alkylaryl($C_1$–$C_6$)alkyl, mono- or di-($C_1$–$C_6$) alkoxyaryl($C_1$–$C_6$)alkyl, mono- or di-($C_1$–$C_6$) alkylaryl($C_1$–$C_6$)alkoxy, mono- or di-($C_1$–$C_6$) alkoxy, amino, mono($C_1$–$C_6$)alklamino di($C_1$–$C_6$) alkylamino, diarylamino, piperazino, N-($C_1$–$C_6$) alkypiperazino, N-arylpiperazino, aziridino, indolino, piperidino, morpholino, thiomorpholino, tetrahydroquinolino, tetrahydroisoquinolino, pyrrolidyl, $C_1$–$C_6$ alkyl, $C_1$–$C_6$ chloroalkyl, $C_1$–$C_6$ fluoroalkyl, $C_1$–$C_6$ alkoxy, mono($C_1$–$C_6$)alkoxy($C_1$–$C_4$) alkyl, acryloxy, methacryloxy, bromo, chloro or fluoro, said aryl being chosen from phenyl or naphthyl;

(iv) an unsubstituted or mono-substituted group chosen from pyrazolyl, imidazolyl, pyrazolinyl, imidazolinyl, pyrrolinyl, phenothiazinyl, phenoxazinyl, phenazinyl or acridinyl, each of said substituents being independently chosen from $C_1$–$C_6$ alkyl, $C_1$–$C_6$ alkoxy, phenyl, fluoro, chloro or bromo;

(v) a monosubstituted phenyl, said phenyl having a substituent located at the para position being —$(CH_2)_r$— or —O—$(CH_2)_r$—, wherein r being chosen from the integer 1, 2, 3, 4, 5 or 6, said substituent being connected to an aryl group which is a member of another photochromic material, and;

(vi) a group represented by one of the following graphic formulae:

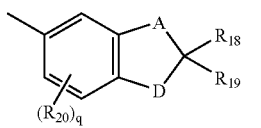 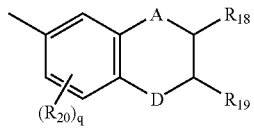

wherein A being independently chosen in each formula from methylene or oxygen and D being independently chosen in each formula from oxygen or substituted nitrogen, provided that when D is substituted nitrogen, A is methylene; said nitrogen substituents being chosen from hydrogen, $C_1$–$C_6$ alkyl, or $C_2$–$C_6$ acyl; each $R_{20}$ being independently chosen for each occurrence in each formula from $C_1$–$C_6$ alkyl, $C_1$–$C_6$ alkoxy, hydroxy, chloro or fluoro; $R_{18}$ and $R_{19}$ each being independently chosen in each formula from hydrogen or $C_1$–$C_6$ alkyl; and q being chosen from the integer 0, 1 or 2;

(vii) $C_1$–$C_6$ alkyl, $C_1$–$C_6$ chloroalkyl, $C_1$–$C_6$ fluoroalkyl, $C_1$–$C_6$ alkoxy($C_1$–$C_6$)alkyl, $C_3$–$C_6$ cycloalkyl, mono($C_1$–$C_6$)alkoxy($C_3$–$C_6$)cycloalkyl, mono ($C_1$–$C_6$)alkyl($C_3$–$C_6$)-cycloalkyl, chloro($C_3$–$C_6$)cycloalkyl, fluoro($C_3$–$C_6$)cyclo-alkyl or $C_4$–$C_{12}$ bicycloalkyl;

(viii) a group represented by the following graphic formula:

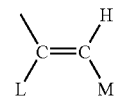

wherein L being chosen from hydrogen or $C_1$–$C_4$ alkyl and M being chosen from an unsubstituted, mono-, or di-substituted group chosen from naphthyl, phenyl, furanyl, or thienyl; each of said group substituents being independently chosen from $C_1$–$C_4$ alkyl, $C_1$–$C_4$ alkoxy, fluoro, or chloro; or (ix) B and B' taken together form fluoren-9-ylidene, mono-, or di-substituted fluoren-9-ylidene or a group being independently chosen from saturated $C_3$–$C_{12}$ spiro-monocyclic hydrocarbon rings, saturated $C_7$–$C_{12}$ spiro-bicyclic hydrocarbon rings or saturated $C_7$–$C_{12}$ spiro-tricyclic hydrocarbon rings; each of said fluoren-9-ylidene substituents being independently chosen from $C_1$–$C_4$ alkyl, $C_1$–$C_4$ alkoxy, fluoro or chloro.

2. The photochromic article of claim 1 wherein photochromic material (b) is represented by graphic formula XIII wherein:

(aa) $R_{61}$ is represented by:
(i) —$SR_{67}$, $R_{67}$ being $C_1$–$C_6$ alkyl or aryl; or
(ii) an amino group chosen from;
(1) —$N(R_{16})R_{17}$, $R_{16}$ and $R_{17}$ each being independently chosen from $C_1$–$C_8$ alkyl, aryl, or $C_3$–$C_{20}$ cycloalkyl; and said aryl group being phenyl or naphthyl;
(2) a nitrogen containing ring represented by the following graphic formula:

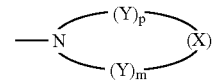

wherein each Y being independently chosen for each occurrence from —$CH_2$—; X being —Y—, —O—, —S—, or —$N(R_{26})$—; $R_{26}$ being $C_1$–$C_6$ alkyl; said aryl group being phenyl or naphthyl, m being chosen from the integer 1, 2 or 3 and p being chosen from the integer 0, 1, 2 or 3; provided that when p is 0, X is Y; or
(3) a group represented by one of the following graphic formulae:

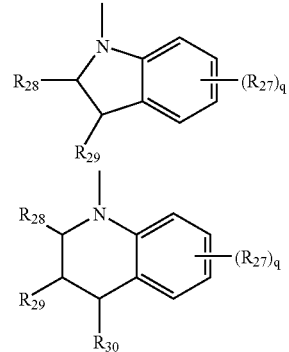

wherein each $R_{28}$, $R_{29}$ and $R_{30}$ being chosen independently for each occurrence in each formula from hydrogen; $R_{27}$ being chosen independently for each occurrence from $C_1$–$C_6$ alkyl, and q being chosen from the integer 0, 1 or 2;

(bb) $R_{61}'$ is independently chosen for each occurrence from $C_1$–$C_6$ alkyl or $C_1$–$C_6$ alkoxy and q being the integer 1;

(cc) $R_{62}$ and $R_{63}$ are each independently chosen from:
 (i) hydrogen, hydroxy, $C_1$–$C_{12}$ alkyl, $C_3$–$C_{12}$ alkylidene, $C_3$–$C_7$ cycloalkyl, or —C(O)W″, wherein W″ is $C_1$–$C_6$ alkoxy, mono($C_1$–$C_6$)alkylamino or di($C_1$–$C_6$)alkylamino;
 (ii) an unsubstituted, mono- di- or tri-substituted group chosen from phenyl; each of said group substituents in (c)(ii) being chosen independently for each occurrence from chloro, fluoro, $C_1$–$C_6$ alkyl or $C_1$–$C_6$ alkoxy;
 (iii) a monosubstituted phenyl, said phenyl having a substituent located at the para position being —O—$(CH_2)_r$—, wherein r being chosen from the integer 3 or 6, said substituent being connected to an aryl group which is a member of another photochromic material;
 (iv) —$OR_{67'}$, $R_{67'}$ being chosen from $C_1$–$C_6$ alkyl, phenyl($C_1$–$C_3$)alkyl, $C_1$–$C_6$)alkoxy($C_2$–$C_4$)alkyl tri($C_1$–$C_6$)alkylsilyl, tri($C_1$–$C_6$)alkoxysilyl, tri($C_1$–$C_6$) alkylsilyloxy, di($C_1$–$C_6$)alkyl($C_1$–$C_6$ alkoxy)silyl, di($C_1$–$C_6$)alkoxy($C_1$–$C_6$)alkoyl)silyl or di($C_1$–$C_6$)alkoxy($C_1$–$C_6$ alkyl)silyloxy;
 (v) —CH(Q″')$_2$, Q″' being chosen from —$COOR_{69}$ and $R_{69}$ being $C_1$–$C_6$ alkyl;
 (vi) —CH($R_{70}$)G″, $R_{70}$ being chosen from hydrogen, $C_1$–$C_6$ alkyl or an unsubstituted, mono- or di-substituted aryl group, phenyl or naphthyl, and G″ being chosen from —$COOR_{69}$, —$COR_{71}$ or —$CH_2OR_{72}$, wherein $R_{71}$ being chosen from hydrogen, $C_1$–$C_6$ alkyl, an unsubstituted, mono- or di-substituted aryl group, phenyl or naphthyl, amino, mono($C_1$–$C_6$)alkylamino, di($C_1$–$C_6$)alkylamino, phenylamino, mono- or di-($C_1$–$C_6$)alkyl substituted phenylamino, mono- or di-($C_1$–$C_6$)alkoxy substituted phenylamino, diphenylamino, mono- or di($C_1$–$C_6$)alkyl substituted diphenylamino, mono- or di-($C_1$–$C_6$) alkoxy substituted diphenylamino, morpholino or piperidino; $R_{72}$ being chosen from hydrogen, —C(O)$R_{69}$, $C_1$–$C_6$ alkyl, $C_1$–$C_3$ alkoxy($C_1$–$C_6$) alkyl, phenyl($C_1$–$C_3$)alkyl, mono($C_1$–$C_6$)alkoxy substituted phenyl($C_1$–$C_3$)alkyl or an unsubstituted, mono- or di-substituted aryl group, phenyl or naphthyl, each of said aryl group substituents being independently chosen from $C_1$–$C_6$ alkyl or $C_1$–$C_6$ alkoxy; or
 (vii) $R_{62}$ and $R_{63}$ together form an oxo group or a substituted or unsubstituted spiro-carbocyclic ring containing 3 to 6 carbon atoms or a substituted or unsubstituted spiro-heterocyclic group containing 1 or 2 oxygen atoms and 3 to 6 carbon atoms including the spirocarbon atom, said spiro-carbocyclic ring and spiro-heterocyclic group being annellated with 0, 1 or 2 benzene rings, said substituents being hydrogen or $C_1$–$C_6$ alkyl;

(dd) $R_{64}$ is hydrogen or $C_1$–$C_6$ alkyl;
(ee) $R_{65}$ is hydrogen or $C_1$–$C_6$ alkyl;
(ff) $R_{66}$ is chosen from hydrogen, $C_1$–$C_6$ alkyl or the group $R_a$, said $R_a$ chosen from:
 (i) —$OR_{73}$, $R_{73}$ being chosen from phenyl($C_1$–$C_3$) alkyl, $C_1$–$C_6$ alkyl, mono($C_1$–$C_6$)alkyl substituted phenyl($C_1$–$C_3$)alkyl, mono($C_1$–$C_6$)alkoxy substituted phenyl($C_1$–$C_3$)alkyl, $C_1$–$C_6$ alkoxy($C_2$–$C_4$) alkyl, $C_3$–$C_7$ cycloalkyl, mono($C_1$–$C_4$)alkyl substituted $C_3$–$C_7$ cycloalkyl, $C_1$–$C_6$ chloroalkyl, $C_1$–$C_6$ fluoroalkyl, allyl or —CH($R_{68}$)Q″; or (ii) an amino group described hereinbefore in (aa)(ii);

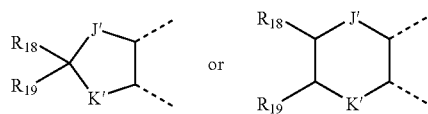

(gg) B and B' are each independently chosen from:
 (i) an unsubstituted, mono-, di-, or tri-substituted phenyl group;
 (ii) a mono-substituted heteroaromatic group chosen from benzofuran-2-yl, benzothien-3-yl, dibenzofuranyl, or carbazoyl; each of said phenyl and heteroaromatic substituents in (i) and (ii) being independently chosen from —C(O)U, wherein U being $C_1$–$C_6$ alkyl, $C_1$–$C_6$ alkoxy, mono-($C_1$–$C_6$)alkylamino, di-($C_1$–$C_6$)alkylamino, morpholino, or piperidino: or amino, mono($C_1$–$C_6$)alkylamino, di($C_1$–$C_6$)alkylamino, piperidino, mornholino or fluoro;
 (iii) an unsubstituted or mono-substituted phenothiazinyl, said substituents being $C_1$–$C_6$ alkyl or $C_1$–$C_6$ alkoxy;
 (iv) a monosubstituted phenyl, said phenyl having a substituent located at the para position being —O—$(CH_2)_r$—, wherein r being chosen from the integer 3 or 6, said substituent being connected to an aryl group which is a member of another photochromic material;
 (v) a group represented by one of the following graphic formulae:

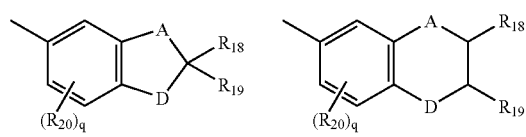

wherein A being independently chosen in each formula from methylene or oxygen and D being independently chosen in each formula from oxygen or substituted nitrogen, provided that when D is substituted nitrogen, A is methylene; said nitrogen substituents being $C_1$–$C_6$ alkyl; each $R_{20}$ being independently chosen for each occurrence in each formula from $C_1$–$C_6$ alkyl or $C_1$–$C_6$ alkoxy; $R_{18}$ and $R_{19}$ each being independently chosen in each formula from hydrogen or $C_1$–$C_6$ alkyl; and q being chosen from the integer 0, 1 or 2;
 (vi) $C_1$–$C_6$ alkyl, $C_3$–$C_6$ cycloalkyl, or $C_4$–$C_{12}$ bicycloalkyl;

(vii) a group represented by the following graphic formula:

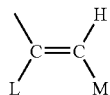

wherein L being hydrogen and M being an unsubstituted, mono-, or di-substituted phenyl;
each of said group substituents being independently chosen from $C_1$–$C_4$ alkoxy or fluoro; or
(viii) B and B' taken together form fluoren-9-ylidene, mono-, or di-substituted fluoren-9-ylidene or a saturated $C_7$–$C_{12}$ spiro-bicyclic hydrocarbon rings;
each of said fluoren-9-ylidene substituents being fluoro.

3. The photochromic article of claim 2 wherein photochromic material (b) is chosen from:
(a) 3,3-di(4-methoxyphenyl)-11-morpholino-13,13-dimethyl-13H-3H-indeno[2',3':3,4]naphtho[1,2-b]pyran;
(b) 3-phenyl-3-(4-morpholinophenyl)-11-morpholino-13,13-dimethyl-13H-3H-indeno[2',3':3,4]naphtho-[1,2-b]pyran;
(c) 3,3-di(4-(2-methoxyethoxyphenyl))-11-morpholino-13,13-dimethyl-13H-3H-indeno[2',3':3,4]naphtho[1,2-b]pyran;
(d) 3,3-di(4-methoxyphenyl)-11-morpholino-13-hydroxy-13-ethyl-13H-3H-indeno[2',3':3,4]naphtho[1,2-b]pyran;
(e) 3,3-di(4-methoxyphenyl)-10-methoxy-11-morpholino-13,13-dimethyl-13H-3H-indeno[2',3':3,4]naphtho[1,2-b]pyran;
(f) 3-(4-methoxyphenyl)-3-(4-morpholinophenyl)-10-methoxy-11-morpholino-13,13-dimethyl-13H-3H-indeno[2',3':3,4]naphtho[1,2-b]pyran;
(g) 3-(3,4-dimethoxyphenyl)-3-(4-methoxyphenyl)-11-morpholino-13,13-dimethyl-13H-3H-indeno[2',3':3,4]naphtho[1,2-b]pyran;
(h) 3-(4-methoxyphenyl)-3-(4-morpholinophenyl)-11-morpholino-13,13-dimethyl-13H-3H-indeno[2',3':3,4]naphtho[1,2-b]pyran; or
(i) 3,3-di(2-methoxyethoxyphenyl)-11-morpholino-13,13-dimethyl-13H-3H-indeno[2',3':3,4]naphtho[1,2-b]pyran.

4. The photochromic article of claim 1 further comprising at least one other photochromic material (c) that is different from photochromic material (b) wherein said photochromic material (c) is chosen from:
(1) a photochromic material chosen from a fluoranthenoxazine represented by the following graphic formula I:

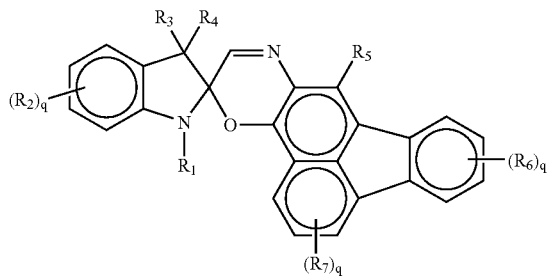

wherein,
(a) $R_1$ is chosen from hydrogen, $C_1$–$C_8$ alkyl, $C_3$–$C_7$ cycloalkyl, phen($C_1$–$C_4$)alkyl, naphth($C_1$–$C_4$)alkyl, allyl, acryloxy($C_2$–$C_6$)alkyl, methacryloyloxy($C_2$–$C_6$)alkyl, $C_2$–$C_4$acyloxy($C_2$–$C_6$)alkyl, carboxy($C_2$–$C_6$)alkyl, cyano($C_2$–$C_6$)alkyl, hydroxy($C_2$–$C_6$)alkyl, triarylsilyl, triarylsilyloxy, tri($C_1$–$C_6$)alkylsilyl, tri($C_1$–$C_6$)alkylsilyloxy, tri($C_1$–$C_6$)alkoxysilyl, tri($C_1$–$C_6$)alkoxysilyloxy, di($C_1$–$C_6$)alkyl($C_1$–$C_6$ alkoxy)silyl, di($C_1$–$C_6$)alkyl($C_1$–$C_6$ alkoxy)silyloxy, di($C_1$–$C_6$)alkoxy($C_1$–$C_6$ alkyl)silyl, di($C_1$–$C_6$)alkoxy($C_1$–$C_6$ alkyl)silyloxy, $C_1$–$C_6$ alkoxy($C_2$–$C_4$)alkyl or $(C_2H_4O)_r$—$CH_3$, wherein r is an integer from 1 to 6;
(b) $R_2$ is chosen from $C_1$–$C_5$ alkyl, $C_1$–$C_5$ alkoxy, nitro, cyano, $C_1$–$C_8$ alkoxycarbonyl, $C_1$–$C_4$ acyloxy, halo, $C_1$–$C_4$ monohaloalkyl or $C_1$–$C_4$ polyhaloalkyl; said halo substituents being chloro, fluoro, iodo or bromo and q is 0, 1 or 2;
(c) $R_3$ and $R_4$ are each independently chosen from $C_1$–$C_5$ alkyl, benzyl, phenyl, mono- or di-substituted phenyl, said phenyl substituents being $C_1$–$C_5$ alkyl or $C_1$–$C_5$ alkoxy; or $R_3$ and $R_4$ taken together form a group chosen from a cyclic ring of from 5 to 8 carbon atoms which includes the spiro carbon atom;
(d) $R_5$ is chosen from hydrogen, —$CH_2Q$ and —$C(O)W$, wherein Q is halogen, hydroxy, benzoyloxy, $C_1$–$C_6$ alkoxy, $C_2$–$C_6$ acyloxy, amino, $C_1$–$C_6$ monoalkylamino, $C_1$–$C_6$ dialkylamino, morpholino, piperidino, 1-indolinyl, pyrrolidyl, triarylsilyl, triarylsilyloxy, tri($C_1$–$C_6$)alkylsilyl, tri($C_1$–$C_6$)alkylsilyloxy, tri($C_1$–$C_6$)alkoxysilyl, tri($C_1$–$C_6$)alkoxysilyloxy, di($C_1$–$C_6$)alkyl($C_1$–$C_6$ alkoxy)silyl, di($C_1$–$C_6$)alkyl($C_1$–$C_6$ alkoxy)silyloxy, di($C_1$–$C_6$)alkoxy($C_1$–$C_6$ alkyl)silyl, di($C_1$–$C_6$)alkoxy($C_1$–$C_6$alkyl)silyloxy, or the group, —$OCH(R_8)Z$; W is the group, —OOH$(R_8)Z$, or an unsubstituted, mono-substituted, or di-substituted heterocyclic ring containing 5 to 6 ring atoms, which ring includes as the hetero atom a nitrogen atom alone or one additional hetero atom of nitrogen or oxygen; wherein Z is —CN, —$CF_3$, halogen, —$C(O)R_8$, or —$COOR_8$, $R_8$ is hydrogen or $C_1$–$C_6$ alkyl; said heterocyclic ring substituents being chosen from $C_1$–$C_6$ alkyl or $C_1$–$C_6$ alkoxy; or W is —$OR_9$ or —$N(R_{10})R_{11}$, wherein $R_9$ is chosen from hydrogen, allyl, $C_1$–$C_6$ alkyl, phenyl, mono($C_1$–$C_6$)alkyl substituted phenyl, mono($C_1$–$C_6$)alkoxy-substituted phenyl, phenyl($C_1$–$C_3$)alkyl, mono($C_1$–$C_6$)alkyl substituted phenyl($C_1$–$C_3$)alkyl, mono($C_1$–$C_6$)alkoxy substituted phenyl($C_1$–$C_3$)alkyl, $C_1$–$C_6$ alkoxy($C_2$–$C_4$)alkyl, or $C_1$–$C_6$ haloalkyl; and $R_{10}$ and $R_{11}$ are each independently chosen from hydrogen, $C_1$–$C_6$ alkyl, $C_5$–$C_7$cycloalkyl, phenyl, mono- or di-substituted phenyl, or $R_{10}$ and $R_{11}$ together with the nitrogen atom form a mono- or di-substituted or unsubstituted heterocyclic ring containing from 5 to 6 ring atoms, which ring includes as the hetero atom said nitrogen atom alone or one additional hetero atom of nitrogen or oxygen, said phenyl and heterocyclic ring substituents being $C_1$–$C_6$ alkyl or $C_1$–$C_6$ alkoxy, and each of said halogen or halo groups in this part (d) being fluoro or chloro;
(e) each $R_6$ and $R_7$ is independently chosen for each occurrence from aryl, mono($C_1$–$C_6$)alkoxyaryl, di($C_1$–$C_6$)alkoxyaryl, mono($C_1$–$C_6$)alkylaryl, di($C_1$–$C_6$)alkylaryl, bromoaryl, chloroaryl, fluoroaryl, $C_3$–$C_7$ cycloalkylaryl, $C_3$–$C_7$ cycloalkyl, $C_3$–$C_7$ cycloalkyloxy, $C_3$–$C_7$ cycloalkyloxy($C_1$–$C_6$)alkyl, $C_3$–$C_7$ cycloalkyloxy($C_1$–$C_6$)alkoxy, aryl($C_1$–$C_6$) alkyl, aryl($C_1$–$C_6$)alkoxy, aryloxy, aryloxy($C_1$–$C_6$) alkyl, aryloxy($C_1$–$C_6$)alkoxy, mono- or di-($C_1$–$C_6$) alkylaryl($C_1$–$C_6$)alkyl, mono- or di-($C_1$–$C_6$) alkoxyaryl($C_1$–$C_6$)alkyl, mono- or di-($C_1$–$C_6$) alkylaryl($C_1$–$C_6$)alkoxy, amino, mono($C_1$–$C_6$) alkylamino, di($C_1$–$C_6$)alkylamino, diarylamino, N—($C_1$–$C_6$)alkylpiperazino, N-arylpiperazino, aziridino, indolino, piperidino, arylpiperidino, morpholino, thiomorpholino, tetrahydroquinolino, tetrahydroisoquinolino, pyrryl, $C_1$–$C_6$ alkyl, $C_1$–$C_6$ bromoalkyl, $C_1$–$C_6$ chloroalkyl, $C_1$–$C_6$ fluoroalkyl, $C_1$–$C_6$ alkoxy, mono($C_1$–$C_6$)alkoxy($C_1$–$C_4$)alkyl, acryloxy, methacryloxy, bromo, chloro or fluoro; and q is independently chosen for each occurrence form the integer 0, 1, or 2;

(2) a photochromic material chosen from a naphthopyran represented by the following graphic formula II:

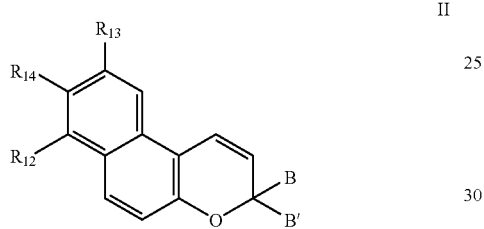

II wherein:

(a) $R_{12}$ is hydrogen or a $C_1$–$C_6$ alkyl;

(b) $R_{13}$ is hydrogen or the group, —C(O)J, J being —OR$_{15}$ or —N(R$_{10}$)R$_{11}$, wherein R$_{15}$ is hydrogen, allyl, $C_1$–$C_6$ alkyl, phenyl, $C_1$–$C_6$ monoalkyl substituted phenyl, $C_1$–$C_6$ monoalkoxy substituted phenyl, phenyl($C_1$–$C_3$)alkyl, $C_1$–$C_6$ monoalkyl substituted phenyl($C_1$–$C_3$)alkyl, $C_1$–$C_6$ monoalkoxy substituted phenyl($C_1$–$C_3$)alkyl, $C_1$–$C_6$ alkoxy($C_2$–$C_4$)alkyl, or $C_1$–$C_6$ monohaloalkyl, and wherein R$_{10}$ and R$_{11}$ are the same as described hereinbefore in (1)(d), and said halo substituent being chloro or fluoro;

(c) $R_{14}$ is —OR$_9$, —N(R$_{10}$)R$_{11}$, wherein R$_9$, R$_{10}$ and R$_{11}$ are the same as described hereinbefore in (1)(d), or the group, —C(O)V; wherein V is $C_1$–$C_6$ alkyl, phenyl, $C_1$–$C_6$ mono- or $C_1$–$C_6$ di-alkyl substituted phenyl, $C_1$–$C_6$ mono- or $C_1$–$C_6$ di-alkoxy substituted phenyl, $C_1$–$C_6$ alkoxy, phenoxy, $C_1$–$C_6$ mono- or $C_1$–$C_6$ di-alkyl substituted phenoxy, $C_1$–$C_6$ mono- or $C_1$–$C_6$ di-alkoxy substituted phenoxy, $C_1$–$C_6$ alkylamino, phenylamino, $C_1$–$C_6$ mono- or $C_1$–$C_6$ di-alkyl substituted phenylamino, or $C_1$–$C_6$ mono- or $C_1$–$C_6$ di-alkoxy substituted phenylamino, and said halo substituent being chloro, fluoro or bromo, provided that either $R_{12}$ or $R_{13}$ is hydrogen; and (d) B and B' are each independently chosen from:
(i) mono-T-substituted phenyl, wherein the group T is represented by the formula:

-G[(OC$_2$H$_4$)$_x$(OC$_3$H$_6$)$_y$(OC$_4$H$_8$)$_z$]G'

—[(OC$_2$H$_4$)$_x$(OC$_3$H$_6$)$_y$(OC$_4$H$_8$)$_z$]G' wherein -G being chosen from —C(O)— or —CH$_2$—, G' being chosen from $C_1$–$C_3$ alkoxy or a polymerizable group, x, y and z each being independently chosen from a number between 0 and 50, and the sum of x, y and z being between 2 and 50;

(ii) an unsubstituted, mono-, di-, or tri-substituted aryl group, phenyl or naphthyl;

(iii) 9-julolidinyl or the unsubstituted, mono- or di-substituted heteroaromatic group chosen from pyridyl furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl or fluorenyl, each of said aryl and heteroaromatic substituents in (ii) and (iii) being independently chosen from hydroxy, —C(O)U, wherein U being hydroxy, $C_1$–$C_6$ alkyl, $C_1$–$C_6$ alkoxy, phenyl, mono-substituted phenyl, amino, mono ($C_1$–$C_6$)alkylamino, di-($C_1$–$C_6$) alkylamino, morpholino, piperidino or pyrrolidyl; aryl, mono($C_1$–$C_6$)alkoxyaryl, di($C_1$–$C_6$) alkoxyaryl, mono($C_1$–$C_6$)alkylaryl, di($C_1$–$C_6$) alkylaryl, chloroaryl, fluoroaryl, $C_3$–$C_7$ cycloalkylaryl, $C_3$–$C_7$ cycloalkyl, $C_3$–$C_7$ cycloalkyloxy, $C_3$–$C_7$ cycloalkyloxy($C_1$–$C_6$)alkyl, $C_3$–$C_7$ cycloalkyloxy($C_1$–$C_6$)alkoxy, aryl($C_1$–$C_6$)alkyl, aryl($C_1$–$C_6$)alkoxy, aryloxy, aryloxy($C_1$–$C_6$)alkyl, aryloxy($C_1$–$C_6$)alkoxy, mono- or di-($C_1$–$C_6$)alkylaryl($C_1$–$C_6$)alkyl, mono- or di-($C_1$–$C_6$) alkoxyaryl($C_1$–$C_6$)alkyl, mono- or di-($C_1$–$C_6$) alkylaryl($C_1$–$C_6$)alkoxy, mono- or di-($C_1$–$C_6$) alkoxyaryl($C_1$–$C_6$)alkoxy, amino, mono($C_1$–$C_6$) alkylamino, di($C_1$–$C_6$)alkylamino, diarylamino, piperazino, N-($C_1$–$C_6$)alkylpiperazino, N-arylpiperazino, aziridino, indolino, piperidino, morpholino, thiomorpholino, tetrahydroquinolino, tetrahydroisoquinolino, pyrrolidyl, $C_1$–$C_6$ alkyl, $C_1$–$C_6$ chloroalkyl, $C_1$–$C_6$ fluoroalkyl, $C_1$–$C_6$ alkoxy, mono($C_1$–$C_6$)alkoxy($C_1$–$C_4$)alkyl, acryloxy, methacryloxy, bromo, chloro or fluoro, said aryl being chosen from phenyl or naphthyl;

(iv) an unsubstituted or mono-substituted group chosen from pyrazolyl, imidazolyl, pyrazolinyl, imidazolinyl, pyrrolinyl, phenothiazinyl, phenoxazinyl, phenazinyl or acridinyl, each of said substituents being independently chosen from $C_1$–$C_6$ alkyl, $C_1$–$C_6$ alkoxy, phenyl, fluoro, chloro or bromo;

(v) a monosubstituted phenyl, said phenyl having a substituent located at the para position being —(CH$_2$)$_r$— or —O—(CH$_2$)$_r$—, wherein r being chosen from the integer 1, 2, 3, 4, 5 or 6, said substituent being connected to an aryl group which is a member of another photochromic material, and;

(vi) a group represented by one of the following graphic formulae:

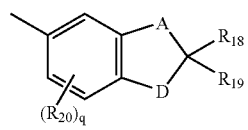 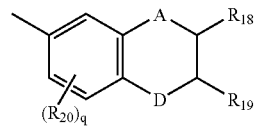

wherein A being independently chosen in each formula from methylene or oxygen and D being independently chosen in each formula from oxygen or substituted nitrogen, provided that when D is substituted nitrogen, A is methylene; said nitrogen substituents being chosen from hydrogen, $C_1$–$C_6$ alkyl, or $C_2$–$C_6$ acyl; each $R_{20}$ being independently chosen for each occurrence in each formula from $C_1$–$C_6$ alkyl, $C_1$–$C_6$ alkoxy, hydroxy, chloro or fluoro; $R_{18}$ and $R_{19}$ each being independently chosen in each formula from hydrogen or $C_1$–$C_6$ alkyl;

and q being chosen from the integer 0, 1 or 2;

(vii) $C_1$–$C_6$ alkyl, $C_1$–$C_6$ chloroalkyl, $C_1$–$C_6$ fluoroalkyl, $C_1$–$C_6$ alkoxy($C_1$–$C_4$)alkyl, $C_3$–$C_6$ cycloalkyl, mono($C_1$–$C_6$)alkoxy($C_3$–$C_6$)cycloalkyl, mono($C_1$–$C_6$)alkyl($C_3C_6$)-cycloalkyl, chloro($C_3$–$C_6$)cycloalkyl, fluoro($C_3$–$C_6$)cycloalkyl or $C_4$–$C_{12}$ bicycloalkyl;

(viii) a group represented by the following graphic formula:

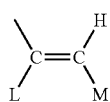

wherein L being chosen from hydrogen or $C_1$–$C_4$ alkyl and M being chosen from an unsubstituted, mono-, or di-substituted group chosen from naphthyl, phenyl, furanyl, or thienyl; each of said group substituents being independently chosen from $C_1$–$C_4$ alkyl, $C_1$–$C_4$ alkoxy, fluoro, or chloro; or (ix) B and B' taken together form fluoren-9-ylidene, mono-, or di-substituted fluoren-9-ylidene or a group being independently chosen from saturated $C_3$–$C_{12}$ spiro-monocyclic hydrocarbon rings, saturated $C_7$–$C_{12}$ spiro-bicyclic hydrocarbon rings or saturated $C_7$–$C_{12}$ spiro-tricyclic hydrocarbon rings; each of said fluoren-9-ylidene substituents being independently chosen from $C_1$–$C_4$ alkyl, $C_1$–$C_4$ alkoxy, fluoro or chloro;

(3) a photochromic material chosen from a naphthopyran represented by the following graphic formula III:

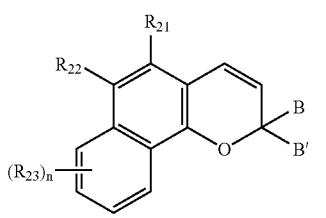

wherein, (a) $R_{21}$ is the group, —C(O)W or $CH_2Q$, described hereinbefore in (1)(d);

(b) $R_{22}$ and each $R_{23}$ are independently chosen for each occurrence from hydroxy, $NH_2$ or N(R)H; wherein R is $C_1$–$C_6$ alkyl or aryl and n is chosen from the integers 0, 1, 2, or 3;

(c) B and B' are each independently chosen from the groups described hereinbefore in (2)(d);

(4) a photochromic material chosen from a naphthopyran represented by the following graphic formula IV:

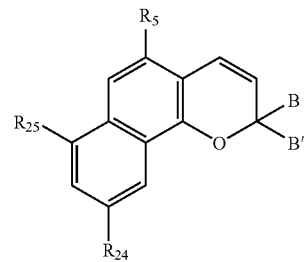

wherein, (a) $R_5$ is the same group described hereinbefore in (1)(d);

(b) $R_{24}$ and $R_{25}$ are each chosen from hydrogen or an amino group defined hereinafter, provided that $R_{24}$ and $R_{25}$ are not both hydrogen; said amino group being:

(i) —N($R_{16}$)$R_{17}$, $R_{16}$ and $R_{17}$ each being independently chosen from hydrogen, $C_1$–$C_8$ alkyl, aryl, furanyl, benzofuran-2-yl, benzofuran-3-yl, thienyl, benzothien-2-yl, benzothien-3-yl, dibenzofuranyl, dibenzothienyl, benzopyridyl, fluorenyl, $C_1$–$C_8$ alkylaryl, $C_3$–$C_{20}$ cycloalkyl, $C_4$–$C_{20}$ bicycloalkyl, $C_5$–$C_{20}$ tricycloalkyl or $C_1$–$C_{20}$ alkoxyalkyl and said aryl group being phenyl or naphthyl;

(ii) a nitrogen containing ring represented by the following graphic formula:

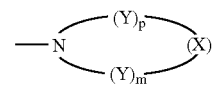

wherein each Y being independently chosen for each occurrence from —$CH_2$—, —CH($R_{26}$)—, —C($R_{26}$)($R_{26}$)—, —CH(aryl)-, —C(aryl)$_2$— or —C($R_{26}$)(aryl)-; X being —Y—, —O—, —S—, —S(O)—, —S($O_2$)—, —NH—, —N($R_{26}$)— or —N(aryl)-; $R_{26}$ being $C_1$–$C_6$ alkyl; said aryl group being phenyl or naphthyl, m being chosen from the integer 1, 2 or 3 and p being chosen from the integer 0, 1, 2 or 3; provided that when p is 0, X is Y;

(iii) a group represented by one of the following graphic formulae:

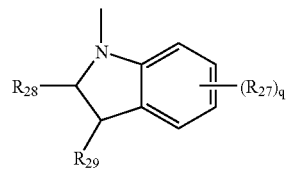

-continued

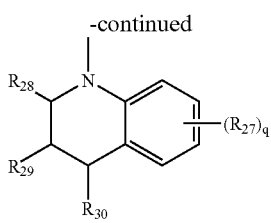

wherein each $R_{28}$, $R_{29}$ and $R_{30}$ being chosen independently for each occurrence in each formula from hydrogen, $C_1$–$C_5$ alkyl, phenyl or naphthyl; or the groups $R_{28}$ and $R_{29}$ together form a ring of 5 to 8 carbon atoms; $R_{27}$ being chosen independently for each occurrence from $C_1$–$C_6$ alkyl, $C_1$–$C_6$ alkoxy, fluoro or chloro and q being chosen from the integer 0, 1 or 2;

(iv) unsubstituted, mono- or di-substituted $C_4$–$C_{18}$ spirobicyclic amine; or (v) unsubstituted, mono- or di-substituted $C_4$–$C_{18}$ spirotricyclic amine; said substituents for (iv) and (v) being independently chosen for each occurrence from aryl, $C_1$–$C_6$ alkyl, $C_{1-6}$ alkoxy or phenyl($C_1$–$C_6$)alkyl;

(c) B and B' are each independently chosen from the groups described hereinbefore in (2)(d);

(5) a photochromic material chosen from a phenanthropyran represented by one of the following graphic formula VA or VB:

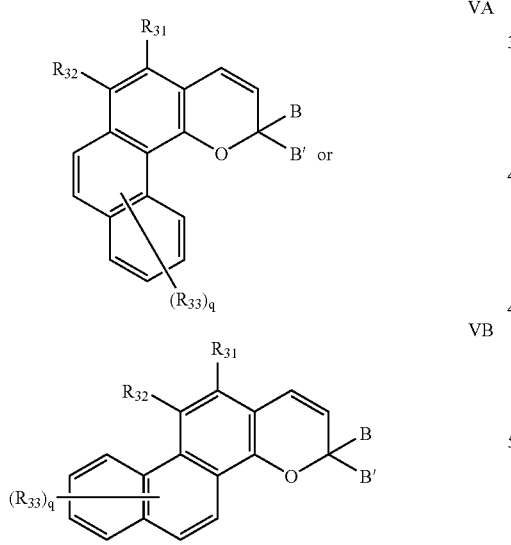

wherein, (a) $R_{31}$ is the group $R_5$, described hereinbefore in (1)(d);

(b) $R_{32}$ is hydrogen, $C_1$–$C_6$ alkyl, $C_1$–$C_6$ alkoxy, $C_3$–$C_7$ cycloalkyl, pyridyl, phenyl, mono-substituted or di-substituted phenyl, said phenyl substituents being $C_1$–$C_6$ alkyl, $C_1$–$C_6$ alkoxy, hydroxy, amino, chloro, or fluoro;

(c) each $R_{33}$ is independently chosen for each occurrence from chloro, fluoro, amino, $C_1$–$C_6$ monoalkylamino, —N($R_{10}$)$R_{11}$, which was described hereinbefore in (1)(d), phenyl, $C_1$–$C_6$ alkyl, or —O$R_{34}$, wherein $R_{34}$ is hydrogen, $C_1$–$C_6$ alkyl, allyl, or acetyl, and q is the integer 0, 1, or 2; and (d) B and B' are each independently chosen from the groups described hereinbefore in (2)(d);

(6) a photochromic material chosen from a fluoranthenopyran represented by the following graphic formula VI:

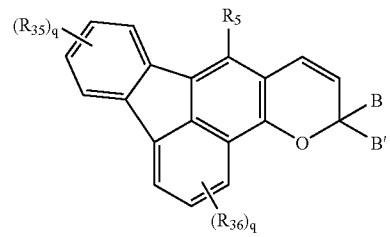

wherein, (a) $R_{35}$ and $R_{36}$ are each independently chosen for each occurrence from hydroxy, aryl, mono($C_1$–$C_6$) alkoxyaryl, di($C_1$–$C_6$)alkoxyaryl, mono($C_1$–$C_6$) alkylaryl, di($C_1$–$C_6$)alkylaryl, bromoaryl, chloroaryl, fluoroaryl, $C_3$–$C_7$ cycloalkylaryl, $C_3$–$C_7$ cycloalkyl, $C_3$–$C_7$ cycloalkyloxy, $C_3$–$C_7$ cycloalkyloxy($C_1$–$C_6$)alkyl, $C_3$–$C_7$ cycloalkyloxy($C_1$–$C_6$) alkoxy, aryl($C_1$–$C_6$)alkyl, aryl($C_1$–$C_6$)alkoxy, aryloxy, aryloxy($C_1$–$C_6$)alkyl, aryloxy($C_1$–$C_6$)alkoxy, mono- or di($C_1$–$C_6$)alkylaryl($C_1$–$C_6$)alkyl, mono- and di($C_1$–$C_6$)alkoxyaryl($C_1$–$C_6$)alkyl, mono- or di($C_1$–$C_6$)alkylaryl($C_1$–$C_6$)alkoxy, mono- or di($C_1$–$C_6$)alkoxyaryl($C_1$–$C_6$)alkoxy, $C_1$–$C_6$ alkyl, $C_1$–$C_6$ bromoalkyl, $C_1$–$C_6$ chloroalkyl, $C_1$–$C_6$ fluoroalkyl, $C_1$–$C_6$ alkoxy, mono($C_1$–$C_6$)alkoxy($C_1$–$C_4$) alkyl, acryloxy, methacryloxy, bromo, chloro, fluoro, amino, mono($C_1$–$C_6$)alkylamino, di($C_1$–$C_6$)alkylamino, phenylamino, mono- or di-($C_1$–$C_6$)alkyl substituted phenylamino or mono- or di-($C_1$–$C_6$) alkoxy substituted phenylamino, and q is the integer 0, 1 or 2;

(b) $R_5$ is chosen from the group described hereinbefore in (1)(d); and (c) B and B' are each independently chosen from the groups described hereinbefore in (2)(d);

(7) a photochromic material chosen from a naphthopyran represented by the following graphic formula VII:

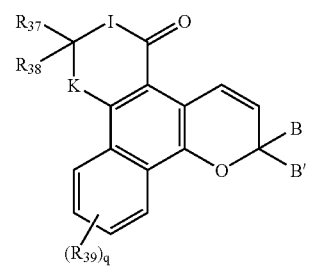

wherein, (a) $R_{37}$ and $R_{38}$ together form an oxo group or $R_{37}$ and $R_{38}$ each are independently chosen for each occurrence from hydrogen, $C_1$–$C_6$ alkyl, $C_3$–$C_7$ cycloalkyl, allyl, phenyl, mono- or di-substituted phenyl, benzyl, mono-substituted benzyl, naphthyl, mono- or di-substituted naphthyl, $C_4$–$C_{12}$ bicycloalkyl, linear or branched $C_3$–$C_{12}$ alkenyl, $C_1$–$C_6$ alkoxy carbonyl($C_1$–$C_6$)alkyl, methacryloxy($C_1$–$C_6$) alkyl, acryloxy($C_1$–$C_6$)alkyl, $C_1$–$C_4$ acyloxy($C_1$–$C_6$) alkyl, $C_1$–$C_6$ alkoxy($C_1$–$C_6$)alkyl or the unsubstituted, mono- or di-substituted heteroaromatic groups pyridyl, furanyl, benzofuran-2-yl, benzyfuran-3-yl, thienyl, benzothien-2-yl, benzothien-3-yl, dibenzofuranyl, dibenzothienyl, carbazolyl, benzopyridyl and indolyl, each of said phenyl, benzyl, naphthyl and heteroaromatic group substituents being $C_1$–$C_6$ alkyl, $C_1$–$C_6$ alkoxy, morpholino, di($C_1$–$C_6$)alkylamino, chloro or fluoro;

(b) $R_{39}$ is chosen from $C_1$–$C_6$ alkyl, $C_1$–$C_6$ alkoxy, chloro, fluoro, phenyl, mono- and di-substituted phenyl, benzyl or mono-substituted benzyl, $C_3$–$C_7$ cycloalkyl, aryloxy, di($C_1$–$C_6$)alkylamino, morpholino, thiomorpholino, piperidino, pyridyl, tetrahydroquinolino, isoquinolino, aziridino, diarylamino, N—($C_1$–$C_6$)alkyl piperizino or N-aryl piperizino, wherein the aryl groups are phenyl or naphthyl, each of said phenyl and benzyl substituents being $C_1$–$C_6$ alkyl, $C_1$–$C_6$ alkoxy, fluoro or chloro, and q is the integer 0, 1 or 2;

(c) I is oxygen or —N($R_{40}$)—, wherein $R_{40}$ is hydrogen, $C_1$–$C_6$ alkyl, $C_3$–$C_7$ cycloalkyl, allyl, vinyl, $C_1$–$C_5$ acyl, phenyl, mono- or di-substituted phenyl, benzyl, mono-substituted benzyl, $C_1$–$C_4$ alkoxycarbonyl($C_1$–$C_6$)alkyl, methacryloxy($C_1$–$C_6$)alkyl, acryloyloxy($C_1$–$C_6$)alkyl, phenyl($C_1$–$C_6$)alkyl, naphthyl, $C_4$–$C_{12}$ bicycloalkyl, $C_2$–$C_4$ acyloxy or the unsubstituted or substituted heteroaromatic groups pyridyl, furanyl, benzofuran-2-yl, benzofuran-3-yl, thienyl, benzothien-2-yl, benzothien-3-yl, dibenzofuranyl, dibenzothienyl, carbazolyl, benzopyridyl or indolyl, each of said phenyl, benzyl and heteroaromatic group substituents being $C_1$–$C_6$ alkyl or $C_1$–$C_6$ alkoxy;

(d) K is oxygen, —N($R_{40}$)— or —C($R_{41}$)($R_{42}$)—, wherein $R_{41}$ and $R_{42}$ are each hydrogen, $C_1$–$C_6$ alkyl or $C_3$–$C_7$ cycloalkyl; and (e) B and B' are each independently chosen from the groups described hereinbefore in (2)(d);

(8) a photochromic material chosen from a naphthopyran represented by the following graphic formula VIII:

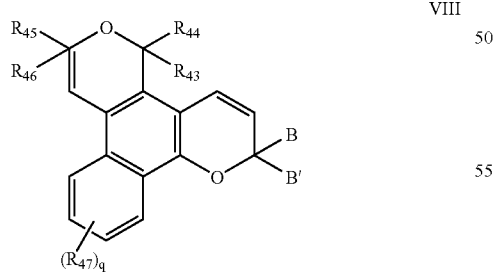

VIII wherein, (a) $R_{43}$ and $R_{44}$ together form an oxo group or $R_{43}$ and $R_{44}$ are both hydrogen, $C_1$–$C_6$ alkyl, $C_3$–$C_7$ cycloalkyl, allyl, phenyl, mono-substituted phenyl, benzyl or mono-substituted benzyl each of said phenyl and benzyl group substituents being $C_1$–$C_6$ alkyl or $C_1$–$C_6$ alkoxy;

(b) $R_{45}$ is hydrogen, $C_1$–$C_6$ alkyl, $C_3$–$C_7$ cycloalkyl, or the group, CH(B)B', wherein B and B' are each independently chosen from the groups described hereinbefore in (2)(d);

(c) $R_{46}$ is hydrogen, $C_1$–$C_6$ alkyl, or $C_3$–$C_7$ cycloalkyl;

(d) each $R_{47}$ is $C_1$–$C_6$ alkyl, $C_1$–$C_6$ alkoxy, chloro or fluoro, and q is the integer 0, 1, or 2; and (e) B and B' are each independently chosen from the groups described hereinbefore in (2)(d);

(9) a photochromic material chosen from a naphthopyran represented by the following graphic formulae IXA, IXB, IXC, IXD, IXE, IXF, IXG or IXH:

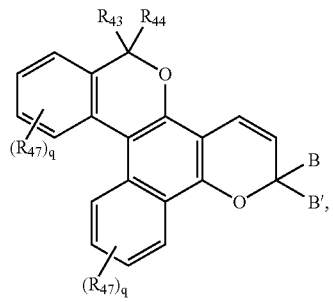

IXA

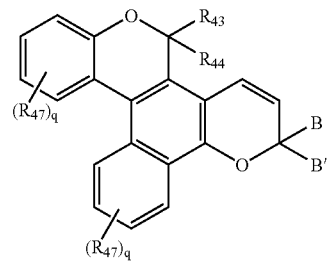

IXB

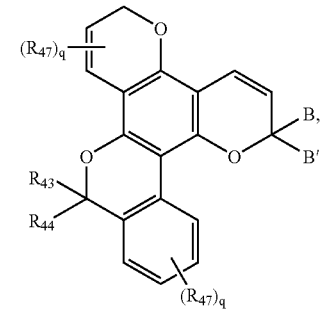

IXC

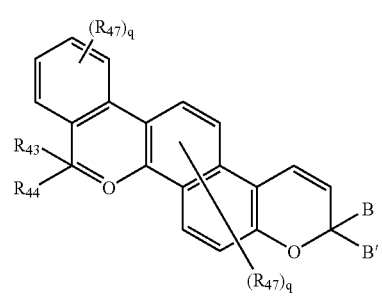

IXD

-continued

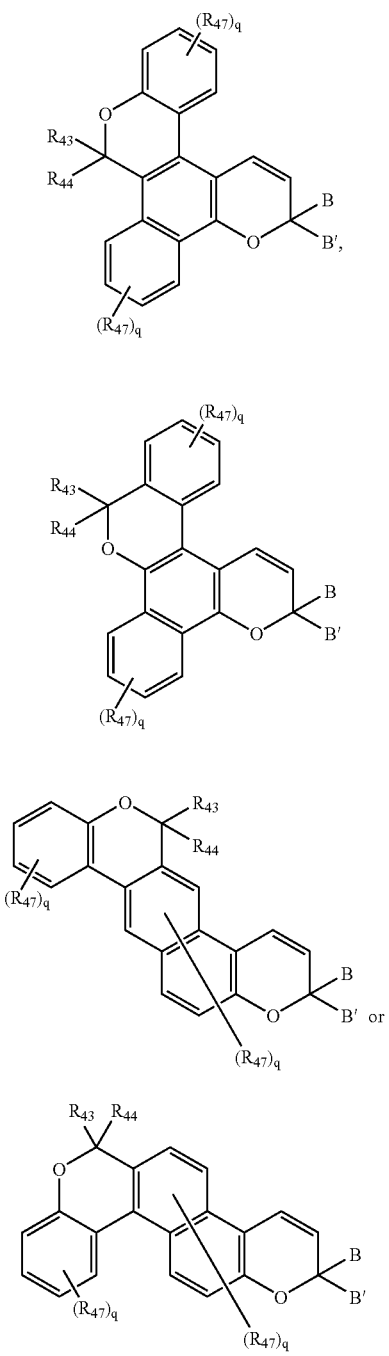

IXE

IXF

IXG

IXH wherein,
(a) $R_{43}$ and $R_{44}$ are the same groups described hereinbefore in (8)(a);
(b) each $R_{47}$ and q are the same as described hereinbefore in (8)(d); and
(c) B and B' are each independently chosen from the groups described hereinbefore in (2)(d);

(10) a photochromic material chosen from a naphthopyran represented by the following graphic formulae XA or XB:

XA

XB wherein,
(a) A' is chosen from:
  (i) an unsubstituted, mono-substituted or di-substituted heterocyclic ring chosen from benzothieno, benzofurano or indolo, the 2,3 or 3,2 positions of said heterocyclic ring being fused to the i, j or k side of said naphthopyran represented by graphic formula XA or said heterocyclic ring is fused to the f side of said naphthopyran represented by graphic formula XB; or
  (ii) an unsubstituted, mono-substituted or di-substituted indeno group fused to the i, j or k side of said naphthopyran represented by graphic formula XA or to the f side of said naphthopyran represented by graphic formula XB; each of said heterocyclic ring and indeno group substituents being $C_1$–$C_6$ alkyl, $C_5$–$C_7$ cycloalkyl, $C_1$–$C_6$ alkoxy, —N($R_{10}$)$R_{11}$, which was described hereinbefore in (1)(d), chloro, fluoro, benzo, mono- or di-substituted benzo group fused to the benzo portion of the benzothieno, benzofurano, indeno or indolo moiety, said benzo substitutent being $C_1$–$C_6$ alkyl, $C_5$–$C_7$ cycloalkyl, $C_1$–$C_6$ alkyl mono-substituted ($C_5$–$C_7$)cycloalkyl, $C_1$–$C_6$ alkoxy, —N($R_{10}$)$R_{11}$, which was described hereinbefore in (1) (d), chloro or fluoro;

(b) $R_{48}$ is chosen from:
  (i) —C(O)W', W' being —OR$_9$ or —N($R_{10}$)$R_{11}$, wherein said groups were described hereinbefore in (1)(d); or
  (ii) —C($R_{51}$)$_2$X', wherein X' is —CN, chloro, fluoro, hydroxy, benzoyloxy, $C_1$–$C_6$ alkoxy, $C_2$–$C_6$ acyloxy, amino, $C_1$–$C_6$ mono-alkylamino, $C_1$–$C_6$ dialkylamino, morpholino, piperidino, 1-indolinyl, pyrrolidyl, or trimethylsilyloxy, $R_{51}$ is hydrogen, $C_1$–$C_6$ alkyl, phenyl or naphthyl, and each of said phenyl and heterocyclic ring substituents in this part (b)(i) and (ii) being $C_1$–$C_6$ alkyl or $C_1$–$C_6$ alkoxy;

(c) $R_{49}$ is hydrogen, $C_1$–$C_6$ alkyl, the mono-, di- or tri-substituted aryl groups phenyl or naphthyl, said aryl substituents being $C_1$–$C_6$ alkyl, $C_1$–$C_6$ alkoxy, chloro or fluoro; or (d) each $R_{50}$ is chloro, fluoro, $C_1$–$C_6$ alkyl, $C_1$–$C_6$ alkoxy, phenyl, naphthyl, phenoxy, naphthoxy or the group, —$N(R_{10})R_{11}$, described hereinbefore in (1)(d), and q is selected from the integers 0, 1 or 2 in said naphthopyran represented by graphic XA, or each $R_{50}$ is chloro, fluoro, phenoxy, naphthoxy or the group, —$N(R_{10})R_{11}$, and p is selected from the integers 0, 1, 2 or 3 in said naphthopyran represented by graphic formula XB; and (e) B and B' are each independently chosen from the groups described hereinbefore in (2)(d);

(11) a photochromic material chosen from a indenonaphthopyran represented by the following graphic formulae XIA or XIB:

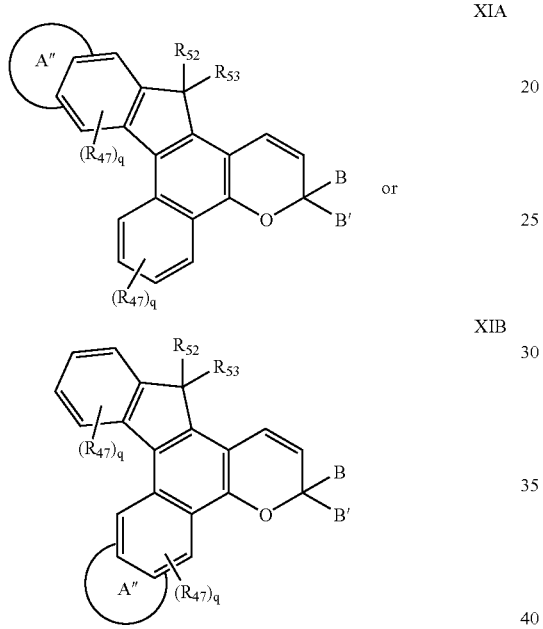

wherein,
(a) A" is an unsubstituted, mono-substituted or di-substituted heterocyclic ring chosen from furo, thieno, benzothieno, benzofurano or indolo, the 2,3 or 3,2 positions of said heterocyclic ring being fused to the g, h or i side of XIB or to the n, o or p side of XIA, said heterocyclic ring substituents being $C_1$–$C_6$ alkyl, $C_5$–$C_7$ cycloalkyl, $C_1$–$C_6$ alkoxy, chloro or fluoro;

(b) $R_{52}$ and $R_{53}$ together form an oxo group, a spiro heterocyclic group having 2 oxygen atoms and from 3 to 6 carbon atoms including the spirocarbon atom, or $R_{52}$ and $R_{53}$ are each hydrogen, hydroxy, $C_1$–$C_6$ alkyl, $C_3$–$C_7$ cycloalkyl, allyl, phenyl, mono-substituted phenyl, benzyl, mono-substituted benzyl, chloro, fluoro or the group, —C(O)W", wherein each W" is hydroxy, $C_1$–$C_6$ alkyl, $C_1$–$C_6$ alkoxy, phenyl, mono-substituted phenyl, amino, mono($C_1$–$C_6$)alkylamino, di($C_1$–$C_6$)alkylamino, morpholino, piperidino or pyrrolidyl; or $R_{52}$ and $R_{53}$ are each the group, —$N(R_{10})R_{11}$, described hereinbefore in (1)(d), or —$OR_{54}$, wherein each $R_{54}$ is $C_1$–$C_6$ alkyl, phenyl($C_1$–$C_3$)alkyl, mono($C_1$–$C_6$)alkyl substituted phenyl($C_1$–$C_3$)alkyl, mono($C_1$–$C_6$)alkoxy substituted phenyl($C_1$–$C_3$)alkyl, mono($C_1$–$C_6$)alkyl substituted phenyl($C_1$–$C_3$)alkyl, $C_1$–$C_6$ alkoxy($C_2$–$C_4$) alkyl, $C_3$–$C_7$ cycloalkyl, mono($C_1$–$C_4$)alkyl substituted $C_3$–$C_7$ cycloalkyl, $C_1$–$C_6$ chloroalkyl, $C_1$–$C_6$ fluoroalkyl, allyl, the group, —$CH(R_{55})X"$, wherein each $R_{55}$ is hydrogen or $C_1$–$C_3$ alkyl, each X" is —CN, —$CF_3$, or —$COOR_{55}$, or each $R_{54}$ is the group, —C(O)Y", wherein each Y' is hydrogen, $C_1$–$C_6$ alkyl, $C_1$–$C_6$ alkoxy, the unsubstituted, mono- or di-substituted aryl groups, phenyl or naphthyl, phenoxy, mono- or di-($C_1$–$C_6$)alkyl substituted phenoxy, mono- or di-($C_1$–$C_6$)alkoxy substituted phenoxy, amino, mono($C_1$–$C_6$)alkylamino, di($C_1$–$C_6$) alkylamino, phenylamino, mono- or di-($C_1$–$C_6$)alkyl substituted phenylamino or mono- or di-($C_1$–$C_6$) alkoxy substituted phenylamino, each of said phenyl, benzyl or aryl group substituents being $C_1$–$C_6$ alkyl or $C_1$–$C_6$ alkoxy;

(c) each $R_{47}$ and q are the same as described hereinbefore in (8)(d); and (d) B and B' are each independently chosen from the groups described hereinbefore in (2)(d);

(12) a photochromic material chosen from an indenonaphthopyran represented by graphic formulae XIIA or XIIB wherein:

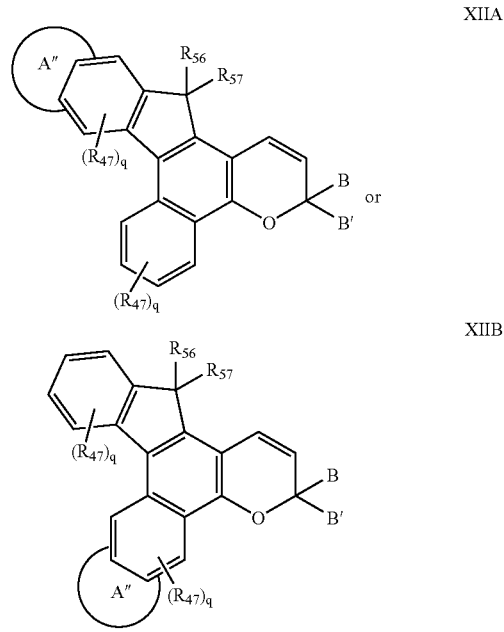

(a) A" is the same group as described hereinbefore in (11)(a) wherein A" is fused to the g, h or i side of XIIB or to the n, o or p side of XIIA;

(b) $R_{56}$ is hydrogen, hydroxy, bromo, fluoro or chloro and $R_{57}$ is the group, —$CH(V')_2$, wherein V' is —CN or —$COOR_{58}$, and each $R_{58}$ is hydrogen, $C_1$–$C_6$ alkyl, phenyl($C_1$–$C_3$)alkyl, mono($C_1$–$C_6$)alkyl substituted phenyl($C_1$–$C_3$)alkyl, mono($C_1$–$C_6$)alkoxy substituted phenyl($C_1$–$C_3$)alkyl or the unsubstituted, mono- or di-substituted aryl groups phenyl or naphthyl, or $R_{57}$ is the group, —$CH(R_{59})Y"$, wherein $R_{59}$ is hydrogen, $C_1$–$C_6$ alkyl or the unsubstituted, mono- or di-substituted aryl groups phenyl or naphthyl, and Y" is —$COOR_{58}$, —$COR_{59}$, or —$CH_2OR_{60}$, wherein $R_{59}$ is hydrogen, $C_1$–$C_6$ alkyl, the unsubstituted, mono- or di-substituted aryl groups phenyl or naphthyl, amino, mono($C_1$–$C_6$)alkylamino, di($C_1$–$C_6$)alkylamino, phenylamino, mono-or di-($C_1$–$C_6$)alkyl substituted phenylamino, mono- or di-($C_1$–$C_6$)alkoxy substituted phenylamino, diphenylamino, mono- or di-($C_1$–$C_6$)alkyl substituted diphenylamino, mono- or di-($C_1$–$C_6$)alkoxy substituted diphenylamino, morpholino, or piperidino; $R_{60}$ is hydrogen, —$COR_{58}$, $C_1$–$C_6$ alkyl, $C_1$–$C_3$ alkoxy($C_1$–$C_6$)alkyl, phenyl($C_1$–$C_3$)alkyl, mono($C_1$–$C_6$) alkyl substituted phenyl($C_1$–$C_3$)alkyl, mono($C_1$–$C_6$) alkoxy substituted phenyl($C_1$–$C_3$)alkyl, or the unsubstituted, mono- or di-substituted aryl groups phenyl or naphthyl, each of said aryl group substituents being $C_1$–$C_6$ alkyl or $C_1$–$C_6$ alkoxy; or (c) $R_{56}$ and $R_{57}$ together form the group, =C(V')$_2$ or =C($R_{59}$)W''', wherein W''' is —$COOR_{58}$ or —$COR_{59}$;

(d) each $R_{47}$ and q are the same as described hereinbefore in (8) (d); and (e) B and B' are each independently chosen from the groups described hereinbefore in (2)(d);

(13) a photochromic material chosen from an indenonaphthopyran represented by the following graphic formula XIV:

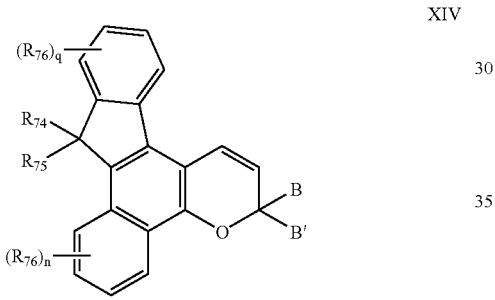

XIV wherein, (a) $R_{74}$ and $R_{75}$ are each independently chosen from:
(i) hydrogen, hydroxy, amino, mono- or di-substituted amino, $C_1$–$C_{12}$ alkyl, $C_3$–$C_{12}$ alkylidene, $C_2$–$C_{12}$ alkylidyne, vinyl, $C_3$–$C_7$ cycloalkyl, $C_1$–$C_6$ alkoxyalkyl, allyl, benzyl, mono-substituted benzyl, chloro, fluoro or —C(O)W'', wherein W'' is hydroxy, $C_1$–$C_6$ alkyl, $C_1$–$C_6$ alkoxy, phenyl, mono-substituted phenyl, amino, mono($C_1$–$C_6$ alkyl amino, di($C_1$–$C_6$)alkyl amino, morpholino, piperidino or pyrrolidyl; said amino substituents in (a)(i) being $C_1$–$C_{C6}$ alkyl, phenyl, benzyl or naphthyl; each of said benzyl substituents being $C_1$–$C_6$ alkyl or $C_{1–C6}$ alkoxy;
(ii) an unsubstituted, mono- di- or tri-substituted group chosen from phenyl, naphthyl, phenanthryl, pyrenyl, quinolyl, isoquinolyl, benzofuranyl, thienyl, benzothienyl, dibenzofuranyl, dibenzothienyl, carbazolyl or indolyl; each of said group substituents in (a)(ii) being chosen independently for each occurrence from chloro, fluoro, $C_1$–$C_6$ alkyl or $C_1$–$C_6$ alkoxy;
(iii) a monosubstituted phenyl, said phenyl having a substituent located at the para position being as described hereinbefore in (2)(d)(v);
(iv) —$OR_{67'}$, $R_{67'}$ being chosen from $C_1$–$C_6$ alkyl, $C_1$–$C_6$ acyl, phenyl($C_1$–$C_3$)alkyl, mono($C_1$–$C_6$) alkyl substituted phenyl($C_1$–$C_3$)alkyl, mono ($C_1$–$C_6$)alkoxy substituted phenyl($C_1$–$C_3$)alkyl, $C_1$–$C_6$ alkoxy($C_2$–$C_4$)alkyl, $C_3$–$C_7$ cycloalkyl, mono($C_1$–$C_4$)alkyl substituted $C_3$–$C_7$ cycloalkyl, $C_1$–$C_6$ chloroalkyl, $C_1$–$C_6$ fluoroalkyl, allyl, triarylsilyl, triarylsilyloxy, tri($C_1$–$C_6$)alkylsilyl, tri ($C_1$–$C_6$)alkylsilyloxy, tri($C_1$–$C_6$)alkoxysilyl, tri ($C_1$–$C_6$)alkoxysilyloxy, di($C_1$–$C_6$)alkyl($C_1$–$C_6$ aloxy)silyl, di($C_1$–$C_6$)alkyl($C_1$–$C_6$ aloxy)silyloxy, di($C_1$–$C_6$)alkoxy($C_1$–$C_6$ alkyl)silyl, di($C_1$–$C_6$) alkoxy($C_1$–$C_6$ alkyl)silyloxy, benzoyl, mono-substituted benzoyl, naphthoyl or mono-substituted naphthoyl; each of said benzoyl and naphthoyl substituents being independently chosen from $C_1$–$C_6$ alkyl or $C_1$–$C_6$ alkoxy; or $R_{67'}$ being —CH ($R_{68}$)Q'', wherein $R_{68}$ being chosen from hydrogen or $C_1$–$C_3$ alkyl and Q'' being chosen from —CN, —$CF_3$, or —$COOR_{68}$; or $R_{67'}$ being —C(O)V'', wherein V'' being chosen from hydrogen, $C_1$–$C_6$ alkoxy, phenoxy, mono- or di-($C_1$–$C_6$) alkyl substituted phenoxy, mono- or di-($C_1$–$C_6$) alkoxy substituted phenoxy, an unsubstituted, mono- or di-substituted aryl group, phenyl or naphthyl, amino, mono($C_1$–$C_6$)alkylamino, di($C_1$–$C_6$)alkylamino, phenylamino, mono- or di-($C_1$–$C_6$)alkyl substituted phenylamino, or mono- or di-($C_1$–$C_6$)alkoxy substituted phenylamino; each of said aryl group substituents being independently chosen from $C_1$–$C_6$ alkyl or $C_1$–$C_6$ alkoxy;

(v) —CH(Q''')$_2$, Q''' being chosen from —CN or —$COOR_{69}$ and $R_{69}$ being chosen from hydrogen, $C_1$–$C_6$ alkyl, phenyl($C_1$–$C_3$)alkyl, mono($C_1$–$C_6$) alkyl substituted phenyl($C_1$–$C_3$)alkyl, mono ($C_1$–$C_6$)alkoxy substituted phenyl($C_1$–$C_3$)alkyl or an unsubstituted, mono- or di-substituted aryl group, phenyl or naphthyl; each of said aryl group substituents being independently chosen from $C_1$–$C_6$ alkyl or $C_1$–$C_6$ alkoxy;

(vi) —CH($R_{70}$)G'', $R_{70}$ being chosen from hydrogen, $C_1$–$C_6$ alkyl or an unsubstituted, mono- or di-substituted aryl group, phenyl or naphthyl, and G'' being chosen from —$COOR_{69}$, —$COR_{71}$ or —$CH_2OR_{72}$, wherein $R_{71}$ being chosen from hydrogen, $C_1$–$C_6$ alkyl, an unsubstituted, mono- or di-substituted aryl group, phenyl or naphthyl, amino, mono($C_1$–$C_6$)alkylamino, di($C_1$–$C_6$)alkylamino, phenylamino, mono- or di-($C_1$–$C_6$)alkyl substituted phenylamino, mono- or di-($C_1$–$C_6$) alkoxy substituted phenylamino, diphenylamino, mono- or di-($C_1$–$C_6$)alkyl substituted diphenylamino, mono- or di-($C_1$–$C_6$)alkoxy substituted diphenylamino, morpholino or piperidino; $R_{72}$ being chosen from hydrogen, —C(O)$R_{69}$, $C_1$–$C_6$ alkyl, $C_1$–$C_3$ alkoxy($C_1$–$C_6$)alkyl, phenyl($C_1$–$C_3$) alkyl, mono($C_1$–$C_6$)alkoxy substituted phenyl ($C_1$–$C_3$)alkyl or an unsubstituted, mono- or di-substituted aryl group, phenyl or naphthyl, each of said aryl group substituents being independently chosen from $C_1$–$C_6$ alkyl or $C_1$–$C_6$ alkoxy;

(vii) the group T being the same as described hereinbefore in (2)(d)(i); or (viii) $R_{74}$ and $R_{75}$ together form an oxo group or a substituted or unsubstituted spiro-carbocyclic ring containing 3 to 6 carbon atoms or a substituted or unsubstituted spiro-heterocyclic group containing 1 or 2 oxygen atoms and 3 to 6 carbon atoms including the spirocarbon atom, said spiro-carbocyclic ring and spiro-heterocyclic group being annellated with 0, 1 or 2 benzene rings, said substituents being hydrogen or $C_1$–$C_6$ alkyl;

(b) $R_{76}$ is independently chosen for each occurrence from di($C_1$–$C_6$)alkylamino, dicyclohexylamino, diphenylamino, piperidyl, morpholinyl, pyridyl, a group T, described hereinbefore in (2)(d)(i); or group —C(O)W", wherein each W" is hydroxy, $C_1$–$C_6$ alkyl, $C_1$–$C_6$ alkoxy, phenyl, mono-substituted phenyl, amino, mono($C_1$–$C_6$)alkylamino, morpholino, piperidino or pyrrolidyl; substituents being $C_1$–$C_6$ alkoxy; and q is the integer 0, 1, or 2; or when q is 2, and the $R_{76}$ substituents are adjacent, each pair of substituents independently forms a substituted or unsubstituted fused carbocyclic or heterocyclic ring chosen from benzo, pyridino, pyrazino, pyrimidino, furano, dihydrofurano, 1,3-dioxolo, 1,4-dioxolo, 1,3-dioxino, 1,4-dioxino, thiopheno, benzofuro, benzothieno, indolo, or indeno, the substituents of said fused carbocyclic or heterocyclic ring being chosen from halogen, $C_1$–$C_6$ alkyl, $C_1$–$C_6$ alkoxy, amino, mono- or di-substituted amino, said amino substituents being chosen from $C_1$–$C_6$ alkyl, phenyl, benzyl or naphthyl; said first $R_{76}$ ring being fused to the o, p or q side and said second $R_{76}$ ring being fused to the g, h, or i side of the indenonaphthopyran; and (c) B and B' are each independently chosen from the groups described hereinbefore in (2)(d); or

(14) mixtures thereof.

5. The photochromic article of claim 4 wherein photochromic material (c) is chosen from:

(1) a photochromic material represented by graphic formula I wherein:

(a) $R_1$ is chosen from $C_1$–$C_8$ alkyl, phen($C_1$–$C_4$)alkyl, acryloxy($C_2$–$C_6$)alkyl, methacrylyloxy($C_2$–$C_6$)alkyl, carboxy($C_2$–$C_6$)alkyl, tri($C_1$–$C_6$)alkylsilyl, tri($C_1$–$C_6$)alkylsilyloxy, tri($C_1$–$C_6$)alkoxysilyl, tri($C_1$–$C_6$)alkoxysilyloxy, di($C_1$–$C_6$)alkyl($C_1$–$C_6$ alkoxy)silyl, di($C_1$–$C_6$)alkyl($C_1$–$C_6$ alkoxy)silyloxy, di($C_1$–$C_6$)alkoxy($C_1$–$C_6$ alkyl)silyl or di($C_1$–$C_6$)alkoxy($C_1$–$C_6$ alkyl)silyloxy;

(b) $R_2$ is chosen from $C_1$–$C_5$ alkyl, $C_1$–$C_5$ alkoxy, $C_1$–$C_8$ alkoxycarbonyl, $C_1$–$C_4$ acyloxy, halo, $C_1$–$C_4$ monohaloalkyl or $C_1$–$C_4$ polyhaloalkyl; said halo substituents being chloro or fluoro, and q is 0, 1 or 2;

(c) $R_3$ and $R_4$ are each independently chosen from $C_1$–$C_5$ alkyl, phenyl; or $R_3$ and $R_4$ taken together form a group chosen from a cyclic ring of from 5 to 8 carbon atoms which includes the spiro carbon atom;

(d) $R_5$ is chosen from —$CH_2Q$ and —C(O)W, wherein Q is halogen, hydroxy, $C_1$–$C_6$ alkoxy, tri($C_1$–$C_6$)alkylsilyl, tri($C_1$–$C_6$)alkylsilyloxy, tri($C_1$–$C_6$)alkoxysilyl, tri($C_1$–$C_6$)alkoxysilyloxy, di($C_1$–$C_6$)alkyl($C_1$–$C_6$ alkoxy)silyl, di($C_1$–$C_6$)alkyl($C_1$–$C_6$ alkoxy)silyloxy, di($C_1$–$C_6$)alkoxy($C_1$–$C_6$ alkyl)silyl, di($C_1$–$C_6$)alkoxy($C_1$–$C_6$ alkyl)silyloxy, or the group, —OCH($R_8$)Z; W is the group, —OCH($R_8$)Z, morpholino or piperidino; Z is —COO$R_8$, $R_8$ is $C_1$–$C_6$ alkyl; or W is —OR$_9$ or —N($R_{10}$)$R_{11}$, wherein $R_9$ is chosen from $C_1$–$C_6$ alkyl or phenyl; and $R_{10}$ and $R_{11}$ are each independently chosen from hydrogen, $C_1$–$C_6$ alkyl, or $R_{10}$ and $R_{11}$ together with the nitrogen atom form a heterocyclic ring chosen from morpholino or piperidino; and each of said halogen or halo groups in this part (d) being fluoro or chloro;

(e) each $R_6$ and $R_7$ is independently chosen for each occurrence from aryl, mono($C_1$–$C_6$)alkoxyaryl, di($C_1$–$C_6$)alkylamino, piperidino, morpholino, $C_1$–$C_6$ alkoxy, or fluoro; and q is independently chosen for each occurrence form the integer 0, 1, or 2, (2) a photochromic material represented by graphic formula II wherein:

(a) $R_{12}$ is hydrogen;

(b) $R_{13}$ is hydrogen or the group, —C(O)J, J being —OR$_{15}$ or —N($R_{10}$)$R_{11}$, wherein $R_{15}$ is $C_1$–$C_6$ alkyl, phenyl($C_1$–$C_3$)alkyl, or $C_1$–$C_6$ alkoxy($C_2$–$C_4$)alkyl, $R_{10}$ and $R_{11}$ are the same as described hereinbefore in (1)(d);

(c) $R_{14}$ is hydrogen, $C_1$–$C_6$ alkyl, phenyl($C_1$–$C_3$)alkyl, $C_1$–$C_6$ alkoxy($C_2$–$C_4$)alkyl, $C_5$–$C_7$ cycloalkyl, or the group, —C(O)V; wherein V is $C_1$–$C_6$ alkyl, $C_1$–$C_6$ alkoxy or $C_1$–$C_6$ alkylamino; and (d) B and B' are each independently chosen from:

(i) an unsubstituted, mono-, di-, or tri-substituted phenyl group;

(ii) a mono-substituted heteroaromatic group chosen from benzofuran-2-yl, benzothien-3-yl, dibenzofuranyl, or carbazoyl; each of said phenyl and heteroaromatic substituents in (i) and (ii) being independently chosen from —C(O)U, wherein U being $C_1$–$C_6$ alkyl, $C_1$–$C_6$ alkoxy, mono($C_1$–$C_6$)alkylamino, di-($C_1$–$C_6$)alkylamino, morpholino, or piperidino; or amino, mono($C_1$–$C_6$)alkylamino, di($C_1$–$C_6$)alkylamino, piperidino, morpholino or fluoro;

(iii) an unsubstituted or mono-substituted phenothiazinyl, said substituents being $C_1$–$C_6$ alkyl or $C_1$–$C_6$ alkoxy;

(iv) a monosubstituted phenyl, said phenyl having a substituent located at the para position being —O—($CH_2$)$_r$—, wherein r being chosen from the integer 3 or 6, said substituent being connected to an aryl group which is a member of another photochromic material;

(v) a group represented by one of the following graphic formulae:

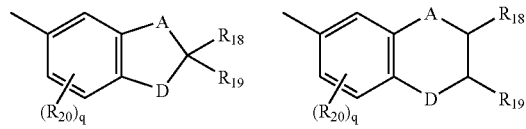

wherein A being independently chosen in each formula from methylene or oxygen and D being independently chosen in each formula from oxygen or substituted nitrogen, provided that when D is substituted nitrogen, A is methylene; said nitrogen substituents being $C_1$–$C_6$ alkyl; each $R_{20}$ being independently chosen for each occurrence in each formula from $C_1$–$C_6$ alkyl or $C_1$–$C_6$ alkoxy; $R_{18}$ and $R_{19}$ each being independently chosen in each formula from hydrogen or $C_1$–$C_6$ alkyl; and q being chosen the integer 0, 1 or 2;

(vi) $C_1$–$C_6$ alkyl, $C_3$–$C_6$ cycloalkyl, or $C_4$–$C_{12}$ bicycloalkyl;

(vii) a group represented by the following graphic formula:

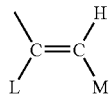

wherein L being hydrogen and M being an unsubstituted, mono-, or di-substituted phenyl; each of said group substituents being independently chosen from $C_1$–$C_4$ alkoxy or fluoro; or (viii) B and B' taken together form fluoren-9-ylidene, mono-, or di-substituted fluoren-9-ylidene or a saturated $C_7$–$C_{12}$ spiro-bicyclic hydrocarbon rings; each of of said fluoren-9-ylidene substituents being fluoro;

(3) a photochromic material represented by graphic formula III wherein:

(a) $R_{21}$ is the group, —C(O)W or $CH_2Q$, described hereinbefore in (1)(d);

(b) $R_{22}$ and each $R_{23}$ are independently chosen for each occurrence from hydroxy, $NH_2$ or N(R)H; wherein R is $C_1$–$C_3$ alkyl or phenyl and n is chosen from the integers 0, 1 or 2;

(c) B and B' are each independently chosen from the groups described hereinbefore in (2)(d);

(4) a photochromic material represented by graphic formula IV wherein:

(a) $R_5$ is chosen from the groups described hereinbefore in (1)(d);

(b) $R_{24}$ and $R_{25}$ are each chosen from hydrogen or an amino group defined hereinafter, provided that $R_{24}$ and $R_{25}$ are not both hydrogen; said amino group being:

(i) —N($R_{16}$)$R_{17}$, $R_{16}$ and $R_{17}$ each being independently chosen from $C_1$–$C_8$ alkyl, aryl, or $C_3$–$C_{20}$ cycloalkyl; and said aryl group being phenyl or naphthyl;

(ii) a nitrogen containing ring represented by the following graphic formula:

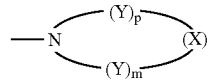

wherein each Y being independently chosen for each occurrence from —$CH_2$—, ; X being —Y—, —O—, —S—, or —N($R_{26}$)—; $R_{26}$ being $C_1$–$C_6$ alkyl; said aryl group being phenyl or naphthyl, m being chosen from the integer 1, 2 or 3 and p being chosen from the integer 0, 1, 2 or 3; provided that when p is 0, X is Y; or (iii) a group represented by one of the following graphic formulae:

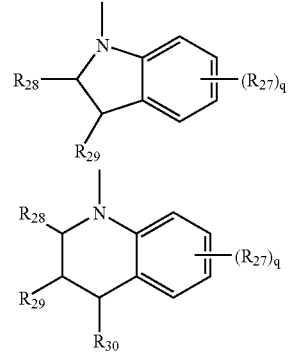

wherein each $R_{28}$, $R_{29}$ and $R_{30}$ being chosen independently for each occurrence in each formula from hydrogen; $R_{27}$ being chosen independently for each occurrence from $C_1$–$C_6$ alkyl, and q being chosen from the integer 0, 1 or 2;

(c) B and B' are each independently chosen from the groups described hereinbefore in (2)(d);

(5) a photochromic material represented by graphic formula V wherein:

(a) $R_{31}$ is $R_5$ described hereinbefore in (1)(d);

(b) $R_{32}$ is hydrogen or $C_1$–$C_6$ alkyl;

(c) each $R_{33}$ is independently chosen for each occurrence from —N($R_{10}$)$R_{11}$, which was described hereinbefore in (1)(d), $C_1$–$C_6$ alkyl, or —O$R_{34}$, wherein $R_{34}$ is $C_1$–$C_6$ alkyl, and q is the integer 0, 1, or 2; and (d) B and B' are each independently chosen from the groups described hereinbefore in (2)(d);

(6) a photochromic material represented by graphic formula VI wherein:

(a) $R_{35}$ and $R_{36}$ are each independently chosen for each occurrence from $C_1$–$C_6$ alkyl, $C_1$–$C_6$ alkoxy, fluoro, amino, mono($C_1$–$C_6$)alkylamino, di($C_1$–$C_6$)alkylamino, phenylamino, mono-or di-($C_1$–$C_6$)alkyl substituted phenylamino or mono- or di-($C_1$–$C_6$)alkoxy substituted phenylamino, and q is the integer 0, 1 or 2;

(b) $R_5$ is chosen from the group described hereinbefore in (1)(d); and (c) B and B' are each independently chosen from the groups described hereinbefore in (2)(d);

(7) a photochromic material represented by graphic formula VII wherein:

(a) $R_{37}$ and $R_{38}$ together form an oxo group or $R_{37}$ and $R_{38}$ each are independently chosen for each occurrence from hydrogen, $C_1$–$C_6$ alkyl, $C_3$–$C_7$ cycloalkyl, phenyl or methacryloxy($C_1$–$C_6$)alkyl;

(b) $R_{39}$ is chosen from $C_1$–$C_6$ alkyl, $C_1$–$C_6$ alkoxy, fluoro, or morpholino, and q is the integer 0, 1 or 2;

(c) I is oxygen or —N($R_{40}$)—, wherein $R_{40}$ is $C_1$–$C_6$ alkyl, $C_3$–$C_7$ cycloalkyl or phenyl;

(d) K is oxygen, —N($R_{40}$)— or —C($R_{41}$)($R_{42}$)—, wherein $R_{41}$ and $R_{42}$ are each hydrogen or $C_1$–$C_6$ alkyl; and (e) B and B' are each independently chosen from the groups described hereinbefore in (2)(d);

(8) a photochromic material represented by graphic formula VIII wherein:
  (a) $R_{43}$ and $R_{44}$ together form an oxo group or $R_{43}$ and $R_{44}$ are both hydrogen, $C_1$–$C_6$ alkyl, $C_3$–$C_7$ cycloalkyl or phenyl;
  (b) $R_{45}$ is hydrogen or $C_1$–$C_6$ alkyl;
  (c) $R_{46}$ is hydrogen or $C_1$–$C_6$ alkyl, $C_3$–$C_7$ cycloalkyl;
  (d) each $R_{47}$ is $C_1$–$C_6$ alkyl, $C_1$–$C_6$ alkoxy or fluoro, and q is the integer 0, 1 or 2; and
  (e) B and B' are each independently chosen from the groups described hereinbefore in (2)(d);
(9) a photochromic material represented by graphic formulae IXA, IXB, IXC, IXD, IXE, IXF, IXG or IXH wherein:
  (a) $R_{43}$ and $R_{44}$ are the same groups described hereinbefore in (8)(a);
  (b) each $R_{47}$ and q are the same as described hereinbefore in (8)(d); and
  (c) B and B' are each independently chosen from the groups described hereinbefore in (2)(d);
(10) a photochromic material represented by graphic formulae XA or XB wherein:
  (a) A' is chosen from:
    (i) an unsubstituted, mono- or di-substituted heterocyclic ring; or
    (ii) an unsubstituted, mono- or di-substituted indeno group, each of said heterocyclic ring and indeno group substituents being $C_1$–$C_4$ alkyl, $C_1$–$C_3$ alkoxy, —N($R_{10}$)$R_{11}$, which was described hereinbefore in (1)(d), benzo, mono- or di-substituted benzo fused to the indeno moiety, said benzo substituents being $C_1$–$C_3$ alkyl, $C_1$–$C_3$ alkoxy or —N($R_{10}$)$R_{11}$;
  (b) $R_{48}$ is chosen from:
    (i) —C(O)W', W' being —OR$_9$ or —N($R_{10}$)$R_{11}$, which groups were described hereinbefore in (1)(d); or
    (ii) —C($R_{51}$)$_2$X', wherein X' is —CN, halogen, hydroxy, benzoyloxy, $C_1$–$C_4$ alkoxy, $C_2$–$C_4$ acyloxy, amino, $C_1$–$C_4$ mono-alkylamino, $C_1$–$C_4$ dialkylamino, morpholino, piperidino, 1-indolinyl or pyrrolidyl, and $R_{51}$ is hydrogen, $C_1$–$C_4$ alkyl, phenyl or naphthyl;
  (c) $R_{49}$ is hydrogen, $C_1$–$C_4$ alkyl, the mono- or di-substituted aryl groups phenyl or naphthyl, said aryl substituents being $C_1$–$C_4$ alkyl or $C_1$–$C_4$ alkoxy, chloro or fluoro;
  (d) each $R_{50}$ is fluoro, $C_1$–$C_4$ alkyl, $C_1$–$C_4$ alkoxy, phenyl, naphthyl, phenoxy, naphthoxy, or the group, —N($R_{10}$)$R_{11}$, described hereinbefore in (1)(d), and q is selected from the integers 0, 1 or 2 for the naphthopyran represented by graphic formula XA or p is selected from the integers 0, 1, 2 or 3 for the naphthopyran represented by graphic formula XB; and
  (e) B and B' are each independently chosen from the groups described hereinbefore in (2)(d);
(11) a photochromic material represented by graphic formulae XIA or XIB wherein:
  (a) A" is an unsubstituted, mono-substituted or di-substituted heterocyclic ring chosen from furo, thieno, benzothieno, benzofurano or indolo, the 2,3 or 3,2 positions of said heterocyclic ring being fused to the p side of said indenonaphthopyran, said heterocyclic ring substituents being $C_1$–$C_6$ alkyl;
  (b) $R_{52}$ and $R_{53}$ together form an oxo group, a spiro heterocyclic group having 2 oxygen atoms and from 3 to 6 carbon atoms including the spirocarbon atom, or $R_{52}$ and $R_{53}$ are each hydrogen, hydroxy, $C_1$–$C_6$ alkyl, $C_3$–$C_7$ cycloalkyl, phenyl or the group, —C(O)W‴, wherein each W‴ is $C_1$–$C_6$ alkoxy, mono($C_1$–$C_6$)alkylamino or di($C_1$–$C_6$)alkylamino, or $R_{52}$ and $R_{53}$ are each the group, —N($R_{10}$)$R_{11}$, described hereinbefore in (1)(d), or —OR$_{54}$, wherein each $R_{54}$ is $C_1$–$C_6$ alkyl, phenyl($C_1$–$C_3$)alkyl, the group, —CH($R_{55}$)X″, wherein each $R_{55}$ is hydrogen or $C_1$–$C_3$ alkyl, each X″ is —COOR$_{55}$, or each $R_{54}$ is the group, —C(O)Y', wherein each Y' is $C_1$–$C_6$ alkyl;
  (c) each $R_{47}$ and q are the same as described hereinbefore in (8)(d); and
  (d) B and B' are each independently chosen from the groups described hereinbefore in (2)(d);
(12) a photochromic material represented by graphic formulae XIIA or XIIB wherein:
  (a) A" is the same as the groups described hereinbefore in (11)(a);
  (b) $R_{56}$ is hydrogen or hydroxy and $R_{57}$ is the group, —CH(V')$_2$, wherein V' is —COOR$_{58}$, and each $R_{58}$ is $C_1$–$C_6$ alkyl or phenyl($C_1$–$C_3$)alkyl; or $R_{57}$ is the group, —CH($R_{59}$)Y‴, wherein $R_{59}$ is hydrogen and Y‴ is —COOR$_{58}$, or —CH$_2$OR$_{60}$ wherein $R_{59}$ is $C_1$–$C_6$ alkyl or di($C_1$–$C_6$)alkylamino; and $R_{60}$ is $C_1$–$C_6$ alkyl; or
  (c) $R_{56}$ and $R_{57}$ together form the group, =C($R_{59}$)W⁗, wherein W⁗ is —COOR$_{58}$;
  (d) each $R_{47}$ and q are the same as described hereinbefore in (8)(d); and
  (e) B and B' are each independently chosen from the groups described hereinbefore in (2)(d);
(13) a photochromic material represented by graphic formula XIV wherein:
  (a) $R_{74}$ and $R_{75}$ are each independently chosen from:
    (i) hydrogen, hydroxy, amino, mono- or di-substituted amino, $C_1$–$C_{12}$ alkyl, $C_3$–$C_{12}$ alkylidene, $C_2$–$C_{12}$ alkylidyne, vinyl, $C_3$–$C_7$ cycloalkyl, $C_1$–$C_6$ alkoxyalkyl, allyl, benzyl, mono-substituted benzyl, chloro, fluoro or —C(O)W″, wherein W″ being the same group described hereinbefore in (11)(b); said amino substituents in (a)(i) being $C_1$–$C_6$ alkyl, phenyl, benzyl or naphthyl; each of said benzyl substituents being $C_1$–$C_6$ alkyl or $C_1$–$C_6$ alkoxy;
    (ii) an unsubstituted, mono- di- or tri-substituted group chosen from phenyl, naphthyl, phenanthryl, pyrenyl, quinolyl, isoquinolyl, benzofuranyl, thienyl, benzothienyl, dibenzofuranyl, dibenzothienyl, carbazolyl or indolyl; each of said group substituents in (a)(ii) being chosen independently for each occurrence from chloro, fluoro, $C_1$–$C_6$ alkyl or $C_1$–$C_6$ alkoxy;
    (iii) a monosubstituted phenyl, said phenyl having a substituent located at the para position being as described hereinbefore in (2)(d)(v);
    (iv) —OR$_{67'}$, $R_{67'}$ being chosen from $C_1$–$C_6$ alkyl, $C_1$–$C_6$ acyl, phenyl($C_1$–$C_3$)alkyl, mono($C_1$–$C_6$) alkyl substituted phenyl($C_1$–$C_3$)alkyl, mono ($C_1$–$C_6$)alkoxy substituted phenyl($C_1$–$C_3$)alkyl, $C_1$–$C_6$ alkoxyl($C_2$–$C_4$)alkyl, $C_3$–$C_7$ cycloalkyl, mono($C_1$–$C_4$)alkyl substituted $C_3$–$C_7$ cycloalkyl, $C_1$–$C_6$ chloroalkyl, $C_1$–$C_6$ fluoroalkyl, allyl, triarylsilyl, triarysiloxy, tri($C_1$–$C_6$)alkylsilyl, tri($C_1$–$C_6$)alkylsilyloxy, tri($C_1$–$C_6$)alkoxysilyl, tri($C_1$–$C_6$)alkoxysilyloxy, di($C_1$–$C_6$)alkyl($C_1$–$C_6$ alkoxy)silyl, di($C_1$–$C_6$)alkyl($C_1$–$C_6$ alkoxy)silyloxy, di($C_1$–$C_6$)alkoxy($C_1$–$C_6$alkyl)silyl, di($C_1$–$C_6$)alkoxy($C_1$–$C_6$ alkyl)silyloxy, benzoyl, mono-substituted benzoyl, naphthoyl or mono-substituted naphthoyl; each of said benzoyl and naphthoyl substituents being independently chosen from $C_1$–$C_6$ alkyl or $C_1$–$C_6$ alkoxy; or $R_{67'}$ being —CH($R_{68}$)Q", wherein $R_{68}$ being chosen from hydrogen or $C_1$–$C_3$ alkyl and Q" being chosen from —CN, —$CF_3$, or COO$R_{68}$; or $R_{67'}$ being —C(O)V", wherein V" being chosen from hydrogen, $C_1$–$C_6$ alkoxy, phenoxy, mono- or di-($C_1$–$C_6$)alkyl substituted phenoxy, mono- or di-($C_1$–$C_6$)alkoxy substituted phenoxy, an unsubstituted, mono- or di-substituted aryl group, phenyl or naphthyl, amino, mono($C_1$–$C_6$)alkylamino, di($C_1$–$C_6$)alkylamino, phenylamino, mono- or di-($C_1$–$C_6$)alkyl substituted phenylamino, or mono- or di-($C_1$–$C_6$)alkoxy substituted phenylamino; each of said aryl group substituents being independently chosen from $C_1$–$C_6$ alkyl or $C_1$–$C_6$ alkoxy;

(v) —CH(Q''')$_2$, Q''' being chosen from —CN or —COO$R_{69}$ and $R_{69}$ being chosen from hydrogen, $C_1$–$C_6$ alkyl, phenyl($C_1$–$C_3$)alkyl, mono($C_1$–$C_6$) alkyl substituted phenyl($C_1$–$C_3$)alkyl, mono ($C_1$–$C_6$)alkoxy substituted phenyl($C_1$–$C_3$)alkyl or an unsubstituted, mono- or di-substituted aryl group, phenyl or naphthyl; each of said aryl group substituents being independently chosen from $C_1$–$C_6$ alkyl or $C_1$–$C_6$ alkoxy;

(vi) —CH($R_{70}$)G", $R_{70}$ being chosen from hydrogen, $C_1$–$C_6$ alkyl or an unsubstituted, mono- or di-substituted aryl group, phenyl or naphthyl, and G" being chosen from —COO$R_{69}$, —CO$R_{71}$ or —$CH_2$O$R_{72}$, wherein $R_{71}$ being chosen from hydrogen, $C_1$–$C_6$ alkyl, an unsubstituted, mono- or di-substituted aryl group, phenyl or naphthyl, amino, mono($C_1$–$C_6$)alkylamino, di($C_1$–$C_6$)alkylamino, phenylamino, mono- or di-($C_1$–$C_6$)alkyl substituted phenylamino, mono- or di-($C_1$–$C_6$) alkoxy substituted phenylamino, diphenylamino, mono- or di-($C_1$–$C_6$)alkyl substituted diphenylamino, mono- or di-($C_1$–$C_6$)alkoxy substituted diphenylamino, morpholino or piperidino; $R_{72}$ being chosen from hydrogen, —C(O)$R_{69}$, $C_1$–$C_6$ alkyl, $C_1$–$C_3$ alkoxy($C_1$–$C_6$)alkyl, phenyl($C_1$–$C_3$) alkyl, mono($C_1$–$C_6$)alkoxy substituted phenyl ($C_1$–$C_3$)alkyl or an unsubstituted, mono- or di-substituted aryl group, phenyl or naphthyl, each of said aryl group substituents being independently chosen from $C_1$–$C_6$ alkyl or $C_1$–$C_6$ alkoxy;

(vii) the group T being the same as described hereinbefore in (2)(d)(i); or (viii) $R_{74}$ and $R_{75}$ together form an oxo group or a substituted or unsubstituted spiro-carbocyclic ring containing 3 to 6 carbon atoms or a substituted or unsubstituted spiro-heterocyclic group containing 1 or 2 oxygen atoms and 3 to 6 carbon atoms including the spirocarbon atom, said spiro-carbocyclic ring and spiro-heterocyclic group being annellated with 0, 1 or 2 benzene rings, said substituents being hydrogen or $C_1$–$C_6$ alkyl;

(b) each $R_{76}$ is independently chosen from di($C_1$–$C_6$) alkylamino, dicyclohexylamino, diphenylamino, piperidyl, morpholinyl, pyridyl, halogen, or group —C(O) W", wherein W" being the same group described hereinbefore in (11)(b) and q is the integer 0, 1, or 2; or when q is 2, and the $R_{76}$ substituents are adjacent, each pair of substituents independently forms a substituted or unsubstituted fused carbocyclic or heterocyclic ring chosen from benzo, dihydrofurano, 1,4-dioxolo, 1,3-dioxino, or benzofuro, the substituents of said fused carbocyclic or heterocyclic ring being chosen from the group consisting of $C_1$–$C_6$ alkyl or $C_1$–$C_6$ alkoxy;

(c) B and B' are each independently chosen from the groups described hereinbefore in (2)(d); or

(14) mixtures thereof.

6. The photochromic article of claim 5 wherein photochromic material (c) is chosen from:

(1) a photochromic material represented by graphic formula I chosen from:
  (a) 1,3,3-trimethyl-spiro[indoline-2,5'-3H-fluorantheno[3,2-b][1,4]oxazine];
  (b) 1,3,3,4,5 (or 1,3,3,5,6)-pentamethyl-spiro[indoline-2,5'-3H-fluorantheno[3,2-b][1,4]oxazine];
  (c) 1-propyl-3,3,4,5 (or 3,3,5,6)-tetramethyl-spiro[indoline-2,5'-3H-fluorantheno[3,2-b][1,4]oxazine]; or
  (d) 1-methoxyethyl-3,3-dimethyl-spiro[indoline-2,5'-3H-fluorantheno[3,2-b][1,4]oxazine];

(2) a photochromic material represented by graphic formula II chosen from:
  (a) 3,3-diphenyl-8-hydroxy-9-carbopropoxy-3H-naphtho [2,1-b]pyran;
  (b) 3-(2-fluorophenyl)-3-(4-methoxyphenyl)-8-hydroxy-9-carbopropoxy-3H-naphtho[2,1-b]pyran;
  (c) 3-(2-fluorophenyl)-3-(4-methoxyphenyl)-8-hydroxy-9-carbomethoxy-3H-naphtho[2,1-b]pyran;
  (d) 3-(2,4-dimethoxyphenyl)-3-(4-methoxyphenyl)-8-hydroxy-9-carbomethoxy-3H-naphtho{2,1-b]pyran;
  (e) 3,3-diphenyl-8-methoxy-9-carbophenoxy-3H-naphtho [2,1-b]pyran;
  (f) 3-(2-fluorophenyl)-3-(4-methoxyphenyl)-8-methoxy-9-carbophenoxy-3H-naphtho[2,1-b]pyran;
  (g) 3-(2-fluorophenyl)-3-(4-methoxyphenyl)-8-methoxy-9-carbomethoxy-3H-naphtho[2,1-b]pyran;
  (h) 3-(2,4-dimethoxyphenyl)-3-(4-methoxyphenyl)-8-acetoxy-9-carbomethoxy-3H-naphtho[2,1-b]pyran;
  (i) 3,3-diphenyl-7-methyl-8-methoxy-3H-naphtho[2,1-b] pyran;
  (j) 3-(2-methoxy,4-acryloxyphenyl)-3-(4-methacryloxyphenyl)-8-benzyloxy-9-(carbo-1-indolinyl-3H-naphtho[2, 1-b]pyran;
  (k) 3-(2,4,6-trifluorophenyl)-3-(2,4,6-trimethoxy-1-naphthyl)-8-acetyl-9-carboniloyl-3H-naphtho[2,1-b]pyran;
  (l) 3-(2-fluorophenyl)-3-(3-methoxy-2-thienyl)-7-h-pentyl-8-benzoyloxy-3H-naphtho[2,1-b]pyran;
  (m) 3,3-spiroadamantylene-8-acetoxy-9-carbomethoxy-3H-naphtho[2,1-b]pyran;
  (n) 3-(4-methoxyphenyl)-3-(2-methyl-2,3-dihydrobenzofur-5-yl)-8-methoxy-9-carbomethoxy-3H-naphtho[2,1-b] pyran;
  (o) 3-(4-methoxyphenyl)-3-(2-phenyl-1-methylvinyl)-8-acetoxy-9-carbomethoxy-3H-naphtho[2,1-b]pyran;
  (p) 3-(4-methoxyphenyl)-3-(9-ethylcarbozol-2-yl)-8-methoxy-9-carbomethoxy-3H-naphtho[2,1-b]pyran;
  (q) 3,3-spirofluoren-9-ylidene-8-methoxy-9-carbomethoxy-3H-naphtho[2,1-b]pyran; or
  (r) 3,3-diphenyl-8-morpholino-9-carbomethoxy-3H-naphtho[2,1-b]pyran;

(3) a photochromic material represented by graphic formula III chosen from:
  (a) 2,2-di(4-methoxyphenyl)-5-methoxycarbonyl-6-hydroxy-2H-naphtho[1,2-b]pyran;

(b) 2,2-di(4-methoxyphenyl)-5-methoxycarbonyl-6-amino-2H-naphtho[1,2-b]pyran;
(c) 2,2-di(4-methoxyphenyl)-5-methoxycarbonyl-6-propylamino-2H-naphtho[1,2-b]pyran;
(d) 2-(4-methoxyphenyl)-2-t-butyl-5-methoxycarbonyl-6-hydroxy-2H-naphtho[1,2-b]pyran;
(e) 2-(4-methoxyphenyl)-2-phenyl-5-methoxycarbonyl-6-amino-2H-naphtho[1,2-b]pyran;
(f) 2,2-(4-methylphenyl)-5-methoxycarbonyl-6-methylamino-2H-naphtho[1,2-b]pyran;
(g) 2,2-diphenyl-5-methoxycarbonyl-6-hydroxy-2H-naphtho[1,2-b]pyran;
(h) 2,2-di(4-methoxyphenyl)-5-methoxycarbonyl-6-phenylamino-2H-naphtho[1,2-b]pyran;
(i) 2,2-di(4-methoxyphenyl)-5-methoxycarbonyl-6-hydroxy,9-methoxy-2H-naphtho[1,2-b]pyran;
(j) 2,2-diphenyl-5-methoxycarbonyl-6-phenylamino-2H-naphtho[1,2-b]pyran;
(k) 2,2di-(3-trifluoromethylphenyl)-5-methoxycarbonyl,6-hydroxy-2H-naphtho[1,2-b]pyran;
(l) 2-(4-methoxyphenyl)-2-(2-methyl,2,3-dihydrobenzofur-5-yl),5-methoxycarbonyl-6-amino-2H-naphtho[1,2-b]pyran; or
(m) 2,2'-spiroadamantylene-5-methoxycarbonyl-6-methoxy-2H-naphtho[1,2-b]pyran;
(4) a photochromic material represented by graphic formula IV chosen from:
(a) 2-phenyl-2-(4-morpholinophenyl)-5-carbomethoxy-9-dimethylamino-2H-naphtho[1,2-b]pyran;
(b) 2,2-di(4-methoxyphenyl)-5-methoxymethyl-9-morpholino-2H-naphtho[1,2-b]pyran; or
(c) 2-(4-methoxyphenyl)-2-(4-piperidinophenyl)-5-carbomethoxy-9-dimethylamino-2H-naphtho[1,2-b]pyran.
(5) a photochromic material represented by graphic formula V chosen from:
(a) 3,3-diphenyl-12-methoxycarbonyl-11-methyl-3H-phenanthro[1,2-b]pyran;
(b) 2,2-diphenyl-5-methoxycarbonyl-6-methyl-2H-phenanthro[4,3-b]pyran;
(c) 2-(4-methoxyphenyl)-2-phenyl-5-methoxycarbonyl-6-methyl-2H-phenanthro[4,3-b]pyran;
(d) 3-(2-fluorophenyl)-3-(4-methoxyphenyl)-6-methoxy-12-methoxycarbonyl-3H-phenanthro[1,2-b]pyran;
(e) spiro[3H-6-methoxy-12-methoxycarbonyl-phenanthro[1,2-b]pyran-3-9'-fluorene];
(f) 2,2-di(4-methoxyphenyl)-10-methoxy-5-methoxycarbonyl-6-methyl-2H-phenanthro[4,3-b]pyran;
(g) 3-(2,3-dihydrobenzofur-5-yl)-3-(4-methoxyphenyl)-6-methoxy-12-methoxycarbonyl-11-methyl-3H-phenanthro[1,2-b]pyran;
(h) 3,3-diphenyl-6-methoxy-12-methoxycarbonyl-11-phenyl-3H-phenanthro[1,2-b]pyran;
(i) 3-(4-methoxyphenyl)-3-(2-methyl-2,3-dihydrobenzofur-5-yl)-6-methoxy-12-methoxycarbonyl-11-phenyl-3H-phenanthro[1,2-b]pyran;
(j) 3-(4-methoxyphenyl)-3-(2-methyl-2,3-dihydrobenzofur-5-yl)-6-methoxy-12-hydroxymethyl-11-phenyl-3H-phenanthro[1,2-b]pyran; or
(k) 2,2-diphenyl-5-N,N-dimethylaminocarbonyl-2H-phenanthro[4,3-b]pyran;
(6) a photochromic material represented by graphic formula VI chosen from:
(a) 5,5-bis(4-methoxyphenyl)-8-ethoxycarbonyl-5H-fluorantheno[3,2-b]pyran;
(b) 5-(4-methoxyphenyl)-5-(4-morpholinophenyl)-8-ethoxycarbonyl-5H-fluorantheno[3,2-b]pyran;
(c) 5,5-diphenyl-8-ethoxycarbonyl-5H-fluorantheno[3,2-b]pyran;
(d) 5,5-bis(4-methoxyphenyl)-8-methylol-5H-fluorantheno[3,2-b]pyran; or
(e) 5,5-bis(4-methoxyphenyl)-2-methoxy-8-methoxycarbonyl-5H-fluorantheno[3,2-b]pyran;
(7) a photochromic material represented by graphic formula VII chosen from:
(a) 7,7-diphenyl-4-oxo-4H-7H-[1,3]dioxino[5',4':3,4]naphtho[1,2-b]pyran;
(b) 7,7-di(4-methoxyphenyl)-4-oxo-4H-7H-[1,3]dioxino[5',4':3,4]naphtho[1,2-b]pyran;
(c) 7-(4-methoxyphenyl)-7-phenyl-2-pentyl-4-oxo-4H-7H-[1,3]dioxino[5',4':3,4]naphtho[1,2-b]pyran;
(d) 7,7-diphenyl-2-ethyl-4-oxo-4H-7H-[1,3]dioxino[5',4':3,4]naphtho[1,2-b]pyran;
(e) 7,7-diphenyl-2-pentyl-4-oxo-4H-7H-[1,3]dioxino[5',4':3,4]naphtho[1,2-b]pyran;
(f) 7,7-diphenyl-2-(2-methylpropyl)-4-oxo-4H-7H-[1,3]dioxino[5',4':3,4]naphtho[12-b]pyran;
(g) 2,7,7-triphenyl-4-oxo-4H-7H-[1,3]dioxino[5',4':3,4]naphtho[1,2-b]pyran;
(h) 7,7-diphenyl-2-(l-phenylethyl)-4-oxo-4H-7H-[1,3]dioxino[5',4':3,4]naphtho[1,2-b]pyran;
(i) 3-methyl-7,7-diphenyl-2,4-dioxo-2,3,4,7-tetrahydro[1,3]oxazino[5',6':3,4]naphtho[1,2-b]pyran;
(j) 3-(2-ethoxycarbonylethyl)-7,7-diphenyl-2,4-dioxo-2,3,4,7-tetrahydro[1,3]oxazino[5',6':3,4]naphtho[1,2-b]pyran;
(k) 3-hexyl-7,7-diphenyl-2,4-dioxo-2,3,4,7-tetrahydro[1,3]oxazino[5',6':3,4]naphtho[1,2-b]pyran;
(l) 3-(2-methacryloyloxyethyl)-7,7-diphenyl-2,4-dioxo-2,3,4,7-tetrahydro[1,3]oxazino[5',6':3,4] naphtho[1,2-b]pyran;
(m) 2,2,7,7-tetraphenyl-4-oxo-2,3,4,7-tetrahydro-1H-pyrimidino[5',4':3,4]naphtho[1,2-b]pyran;
(n) 2,2,7,7-tetraphenyl-4-oxo-2,3,4,7-tetrahydro-1H-[1,3]oxazino[5',4':3,4]naphtho[1,2-b]pyran;
(o) 7,7-diphenyl-1,2,4,7-tetrahydro-2,2-dimethylpyrano[3',4':3,4]naphtho[1,2-b]pyran;
(p) 7-phenyl-7-(4-morpholinophenyl)-2-pentyl-4-oxo-4H-7H-[1,3]dioxino[5',4':3,4]naphtho[1,2-b]pyran;
(q) 7-(2-fluorophenyl)-7-(3-methyl-4-methoxyphenyl)-2-pentyl-4-oxo-4H-7H-[1,3]dioxino[5',4':3,4]naphtho[1,2-b]pyran;
(r) 7-(4-methoxyphenyl)-7-(2,4-dimethoxyphenyl)-2-pentyl-4-oxo-4H-7H-[1,3]dioxino[5',4':3,4]naphtho[1,2-b]pyran;
(s) 7-(4-morpholino-2-fluorophenyl)-7-(4-methoxyphenyl)-2-pentyl-4-oxo-4H-7H-[1,3]dioxino[5',4':3,4]naphtho[1,2-b]pyran;
(t) 7-(2-fluoro-4-methoxyphenyl)-7-(4-morpholinophenyl)-2-pentyl-4-oxo-4H-7H-[1,3]dioxino[5',4':3,4]naphtho[1,2-b]pyran; or
(u) 7-(4-morpholino-2-fluorophenyl)-7-(3,4-dimethoxyphenyl)-2-pentyl-4-oxo-4H-7H-[1,3]dioxino[5',4':3,4]naphtho[1,2-b]pyran;
(8) the photochromic material:
(a) 2-(4-methoxyphenyl)-2-(2,4-dimethoxy-phenyl)-7-diphenylmethyl-10-methyl-5-oxo-2H-5H-pyrano[3',4':3,4]naphtho[1,2-b]pyran;
(9) a photochromic material represented by graphic formula IXA, IXB, IXC or IXD chosen from:
(a) 2,2-bis(4-methoxyphenyl)-10-oxo-2,10-dihydro[2]benzopyrano[4',3':3,4]naphtho(2,1-b)pyran;
(b) 6,6-bis(4-methoxyphenyl)-10-oxo-6,10-dihydro[2]benzopyrano[3',4':3,4]naphtho(1,2-b)pyran;

(c) 6,6-bis(4-methoxyphenyl)-6,10-dihydro[2]benzopyrano[3',4':3,4]naphtho(1,2-b)pyran;

(d) 2-(4-methoxyphenyl)-2-(4-morpholinophenyl)-10-oxo-2,10-dihydro[2]benzopyrano[4',3':3,4]naphtho (2,1-b)pyran;

(e) 6-(4-methoxyphenyl)-6-(4-morpholinophenyl)-10-oxo-6,10-dihydro[2]benzopyrano[3',4':3,4]naphtho(1,2-b)pyran;

(f) 10,10-dimethyl-6-(4-methoxyphenyl)-6-(4-morpholinophenyl)-6,10-dihydro[2]benzopyrano[3',4':3,4]naphtho(1,2-b)pyran;

(g) 2-(4-morpholinophenyl)-2-phenyl-10-oxo-2,10-dihydro[2]benzopyrano[4',3':3,4]naphtho(2,1-b)pyran;

(h) 6-(4-morpholinophenyl)-6-phenyl-10-oxo-6,10-dihydro[2]benzopyrano[3',4':3,4]naphtho(1,2-b)pyran;

(i) 2,2-bis(4-methoxyphenyl)-12,13-dimethoxy-10-oxo-2,10-dihydro[2]benzopyrano[4',3':3,4]naphtho(2,1-b)pyran;

(j) 6,6-bis(4-methoxyphenyl)-1 2,1 3-dimethoxy-10-oxo-6, 10-dihydro[2]benzopyrano[3',4':3,4]naphtho (1,2-b)pyran;

(k) 6-(4-methoxyphenyl)-6-phenyl-12,13-dimethoxy-10-oxo-6,10-dihydro[2]benzopyrano[3',4':3,4]naphtho(1,2-b)pyran;

(l) 2-(4-methoxyphenyl)-2-phenyl-12,13-dimethoxy-10-oxo-2,10-dihydro[2]benzopyrano[4',3':3,4]naphtho(2,1-b)pyran;

(m) 6-(4-methoxyphenyl)-6-phenyl-12,13-dimethoxy-10,10-dimethyl-6,10-dihydro[2]benzopyrano[3',4':3,4]naphtho(1,2-b)pyran;

(n) 2,2-bis(4-methoxphenyl)-12-methoxy-10-oxo-2,10-dihydro[2]benzopyrano[4',3':3,4]naphtho(2,1-b)pyran;

(o) 6,6-bis(4-methoxyphenyl)-12-methoxy-10-oxo-6,10-dihydro[2]benzopyrano[3',4':3,4]naphtho(1,2-b)pyran;

(p) 6,6-diphenyl-9-oxo-6,9-dihydro[1]benzopyrano[3',4':3,4]naphtho(1,2-b)pyran; or (q) 3,3-diphenyl-8-oxo-3,8-dihydro[2]benzopyrano[3',4':5,6]naphtho(2,1-b)pyran;

(10) a photochromic material represented by graphic formula XA or XB chosen from:

(a) 2,2-bis(4-methoxyphenyl)-5-methoxycarbonyl-6-methyl-2H-benzofuro[2',3':7,8]naphtho[1,2-b]pyran;

(b) 2-(4-methoxyphenyl)-2-(4-propoxyphenyl)-5-methoxycarbonyl-6-methyl-2H-benzofuro[2',3':7,8]naphtho[1,2-b]pyran;

(c) 2,2'-spiroadamantylene-5-methoxycarbonyl-6-methyl-2H-benzofuro[2',3':7,8]naphtho[1,2-b]pyran;

(d) 3,3-bis(4-methoxyphenyl)-10-methoxy-3H-naphtho[2'',1'':4',5']furo[2',3':3,4]naphtho[1,2-b]pyran;

(e) 3,3-bis(4-methoxyphenyl)-3H-naphtho[1'',2'':4',5']furo[3',2':3,4]naphtho[1,2-b]pyran;

(f) 3,3'-spiroadamantylene-3H-naphtho[1'',2'':4',5']furo[3',2':3,4]naphtho[1,2-b]pyran;

(g) 2,2-bis(4-methoxyphenyl)-5-methoxycarbonyl-6-methyl-2H-indeno[3',2':7:8]naphtho[1,2-b]pyran;

(h) 3,3-di(4-methoxyphenyl)-6,11-dimethoxy-13-butyl-13-ethoxy-13H-3H-indeno[2',3',3,4]naphtho[1,2-b]pyran; or (i) 3,3-di(4-methoxyphenyl)-10,11-dimethoxy-13,13-dimethyl-13H-3H-indeno[2',3',3,4]naphtho[1,2-b]pyran;

(11) a photochromic material represented by graphic formula XIA or XIB chosen from:

(a) 3,3-di(4-methoxyphenyl)-16-hydroxy-16-ethyl-16H-benzofuro[2',3':7,8]indeno[2',3':3,4]naphtho[1,2-b]pyran;

(b) 3,3-di(4-methoxyphenyl)-16-hydroxy-[16H]-benzofuro[2'',3'':6',7']indeno[3',2':4,3]naphtho[1,2-b]pyran; or (c) 3,3-di(4-methoxyphenyl)-16-hydroxy-16-ethyl-16H-benzofuro[2'',3'':6',7']indeno[3',2':4,3]naphtho[1,2-b]pyran;

(12) a photochromic material represented by graphic formula XIIA or XIIB chosen from:

(a) 3,3-di(4-methoxyphenyl)-16-(ethoxycarbonyl)methyl-16-hydroxy-3,16-di[H]-benzofuro[2',3':7,8]indeno[2',3':3,4]naphtho[1,2-b]pyran;

(b) 3-(4-methoxyphenyl)-3-(4-morpholinophenyl)-16-(ethoxycarbonyl)methyl-16-hydroxy-3,16-di[H]-benzofuro[2',3':7,8]indeno[2',3':3,4]naphtho[1,2-b]pyran;

(c) 3-phenyl-3-(4-methoxyphenyl)-16-(ethoxycarbonyl)methyl-16-hydroxy-3,16-di[H]-benzofuro[2'',3'':6',7']indeno[3',2':4,3]naphtho[1,2-b]pyran; or (d) 3-phenyl-3-(4-morpholinophenyl)-16-(ethoxycarbonyl)methyl-16-hydroxy-3,16-di[H]-benzofuro[2'',3'':6',7']indeno[3',2':4,3]naphtho[1,2-b]pyran;

(13) a photochromic material represented by graphic formula XIV chosen from:

(a) 3,3,9-triphenyl-3H-9H-indeno[3',2':3,4]naphtho[1,2-b]pyran;

(b) 3,3-di(4-methoxyphenyl)-9-phenyl-3H-9H-indeno[3',2':3,4]naphtho[1,2-b]pyran;

(c) 3-(4-methoxyphenyl)-3,9-diphenyl-3H-9H-indeno[3',2':3,4]naphtho[1,2-b]pyran;

(d) 3-(4-morpholinophenyl)-3,9-diphenyl-3H-9H-indeno[3',2':3,4]naphtho[1,2-b]pyran;

(e) 3,3-di(4-methoxyphenyl)-9-(3-methoxyphenyl)-11-methoxy-3H-9H-indeno[3',2':3,4]naphtho[1,2-b]pyran;

(f) 3-(4-methoxyphenyl)-3-phenyl-9-(3-methoxyphenyl)-11-methoxy-3H-9H-indeno[3',2':3,4]naphtho[1,2-b]pyran;

(g) 3-(4-methoxyphenyl)-3-phenyl-9-methyl-11-methoxy-9-(3-methoxyphenyl)-3H-9H-indeno[3',2':3,4]naphtho[1,2-b]pyran;

(h) 3,3-di(4-methoxyphenyl)-9-methyl-11-methoxy-9-(3-methoxyphenyl)-3H-9H-indeno[3',2':3,4]naphtho[1,2-b]pyran;

(i) 3,3-di(4-methoxyphenyl)-9-methyl-11-methoxy-3H-9H-indeno[3',2':3,4]naphtho[1,2-b]pyran;

(j) 3,3-di(4-methoxyphenyl)-9,9-dimethyl-11-methoxy-3H-9H-indeno[3',2':3,4]naphtho[1,2-b]pyran;

(k) 3-(4-methoxyphenyl)-3-phenyl-9,9-dimethyl-11-methoxy-3H-9H-indeno[3',2':3,4]naphtho[1,2-b]pyran;

(l) 3,3-di(4-methoxyphenyl)-9,9-dimethyl-7,11-dimethoxy-3H-9H-indeno[3',2':3,4]naphtho[1,2-b]pyran;

(m) 3-(4-methoxyphenyl)-3-phenyl-9,9-dimethyl-7,11-dimethoxy-3H-9H-indeno[3',2':3,4]naphtho[1,2-b]pyran;

(n) 3-(4-morpholinophenyl)-3-phenyl-9,9-dimethyl-7,11-dimethoxy-3H-9H-indeno[3',2':3,4]naphtho[1,2-b]pyran;

(o) 3,3-di(4-methoxyphenyl)-9-methyl-11,13-dimethoxy-3H-9H-indeno[3',2':3,4]naphtho[1,2-b]pyran;

(p) 3-(4-methoxyphenyl)-3-phenyl-9-methyl-11,13-dimethoxy-3H-9H-indeno[3',2':3,4]naphtho[1,2-b]pyran;

(q) 3-(4-methoxyphenyl)-3-phenyl-9,9-dimethyl-3H-9H-benzo[4'',5'']indeno[3',2':3,4]naphtho[1,2-b]pyran; or (r) 3,3-di(4-methoxyphenyl)-9,9-dimethyl-11-fluoro-3H-9H-indeno[3',2':3,4]naphtho[1,2-b]pyran; or

(14) mixtures thereof.

7. The photochromic article of claim 6 wherein photochromic material (c) is chosen from:

(a) 7,7-diphenyl-2-pentyl-4-oxo-4H-7H-[1,3]dioxino[5',4':3,4]naphtho[1,2-b]pyran;

(b) 7-phenyl-7-(4-morpholinophenyl)-2-pentyl-4-oxo-4H-7H-[1,3]dioxino[5',4':3,4]naphtho[1,2-b]pyran;

(c) 7-(2-fluorophenyl)-7-(3-methyl-4-methoxyphenyl)-2-pentyl-4-oxo-4H-7H-[1,3]dioxino[5',4':3,4]naphtho[1,2-b]pyran;

(d) 3-(4-methoxyphenyl)-3-phenyl-10,11-dimethoxy-13,13-dimethyl-13H-3H-indeno[2',3',3,4]naphtho[1,2-b]pyran;

(e) 2-(4-methoxyphenyl)-2-(2,4-dimethoxyphenyl)-7-diphenylmethyl-10-methyl-5-oxo-2H-5H-pyrano[3',4':3,4]naphtho[1,2-b]pyran;

(f) 7-(4-methoxyphenyl)-7-(2,4-dimethoxyphenyl)-2-pentyl-4-oxo-4H-7H-[1,3]dioxino[5',4':3,4]naphtho[1,2-b]pyran;

(g) 7-(4-morpholino-2-fluorophenyl)-7-(4-methoxyphenyl)-2-pentyl-4-oxo-4H-7H-[1,3]dioxino[5',4':3,4]naphtho[1,2-b]pyran;

(h) 7-(2-fluoro-4-methoxyphenyl)-7-(4-morpholinophenyl)-2-pentyl-4-oxo-4H-7H-[1,3]dioxino[5',4':3,4]naphtho[1,2-b]pyran;

(i) 7-(4-morpholino-2-fluorophenyl)-7-(3,4-dimethoxyphenyl)-2-pentyl-4-oxo-4H-7H-[1,3]dioxino[5',4':3,4]naphtho[1,2-b]pyran;

(j) 3,3-di(4-methoxyphenyl)-6,11-dimethoxy-13-butyl-13-ethoxy-13H-3H-indeno[2',3',3,4]naphtho[1,2-b]pyran ;

(k) 3,3-di(4-methoxyphenyl)-10,11-dimethoxy-13,13-dimethyl-13H-3H-indeno[2',3',3,4]naphtho[1,2-b]pyran; or (l) mixtures thereof.

8. The photochromic article of claim 1 further comprising at least one fixed tint dye.

9. The photochromic article of claim 1 wherein said photochromic article is adapted to exhibit a neutral activated color.

10. The photochromic article of claim 1 wherein the photochromic article is adapted to retain at least 20 percent of said ΔOD.

11. The photochromic article of claim 1 further comprising an at least partial coating of an at least partially abrasion resistant coating applied to at least one surface of the substrate.

12. The photochromic article of claim 11 further comprising an at least partial coating of an at least partially antireflective coating applied to the at least partial coating of an at least partially abrasion resistant coating.

13. The photochromic article of claim 1 wherein the substrate comprises at least one photochromic material (b).

14. The photochromic article of claim 13 wherein the substrate further comprises at least one photochromic material (c) that is different from photochromic material (b).

15. The photochromic article of claim 1 further comprising an at least partial coating of an at least partially cured polymeric coating applied to at least one surface of the substrate.

16. The photochromic article of claim 15 wherein the at least partially cured polymeric coating comprises photochromic material (b).

17. The photochromic article of claim 16 wherein the at least partially cured polymeric coating further comprises at least one other photochromic material (c) that is different from photochromic material (b).

18. The photochromic article of claim 15 wherein the at least partially cured polymeric coating is a polymeric coating of thermoplastic or thermosetting materials.

19. The photochromic article of claim 18 wherein the at least partially cured polymeric coating is a polymeric coating of thermosetting materials chosen from polyurethanes, aminoplast resins, poly(meth)acrylates, polyanhydrides, polyacrylamides, epoxy resins or polysilanes.

20. The photochromic article of claim 15 further comprising an at least partial coating of primer interposed between the at least partially cured polymeric coating and the substrate.

21. The photochromic article of claim 20 further comprising an at least partial coating of an at least partially abrasion resistant coating applied to the surface of the at least partially cured polymeric coating.

22. The photochromic article of claim 21 further comprising an at least partial coating of an at least partially antireflective coating applied to the at least partial coating of an at least partially abrasion resistant coating applied to the surface of the at least partially cured polymeric coating.

23. The photochromic article of claim 1 wherein the substrate is chosen from paper, glass, ceramic, wood, masonry, textile, metal or organic polymeric material.

24. The photochromic article of claim 23 wherein the substrate is organic polymeric material and said organic polymeric material is chosen from poly($C_1$–$C_{12}$ alkyl methacrylates), poly(oxyalkylene dimethacrylates), poly(alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), thermoplastic polycarbonates, polyesters, polyurethanes, poly(ethylene terephthalate), polystyrene, poly(alpha methylstyrene), copoly(styrene-methylmethacrylate), copoly(styrene-acrylonitrile), polyvinylbutyral or is polymerized from monomers chosen from bis(allyl carbonate) monomers, polyfunctional acrylate monomers, polyfunctional methacrylate monomers, diethylene glycol dimethacrylate monomers, diisopropenyl benzene monomers, ethoxylated bisphenol A dimethacrylate monomers, ethylene glycol bismethacrylate monomers, poly(ethylene glycol) bismethacrylate monomers, ethoxylated phenol bis methacrylate monomers, alkoxylated polyhydric alcohol polyacrylate monomers, styrene monomers, urethane acrylate monomers, glycidyl acrylate monomers, glycidyl methacrylate monomers, diallylidene pentaerythritol monomers or mixtures thereof.

25. The photochromic article of claim 24 wherein the substrate is an organic polymeric material and said organic polymeric material is an optical element.

26. The photochromic article of claim 25 wherein the substrate is an optical element and said optical element is an ophthalmic lens.

27. The photochromic article of claim 1 further comprising a superstrate connected to at least a portion of the substrate, said superstrate comprising at least one organic polymeric material.

28. The photochromic article of claim 27 wherein said superstrate comprises photochromic material (b).

29. The photochromic article of claim 28 wherein said superstrate further comprises at least one other photochromic material (c) that is different from photochromic material (b).

30. The photochromic article of claim 27 wherein the superstrate is adheringly bonded to at least a portion of the substrate.

31. The photochromic article of claim 27 wherein the superstrate is an organic polymeric material chosen from thermosetting or thermoplastic materials.

32. The photochromic article of claim 31 wherein the superstrate is a thermoplastic material and is polyurethane.

33. The photochromic article of claim 27 further comprising an at least partially abrasion resistant film superposed on at least a portion of the superstrate.

34. The photochromic article of claim 33 wherein the at least partially abrasion resistant film is an organic polymeric material chosen from thermoplastic and thermosetting materials.

35. The photochromic article of claim 34 wherein the at least partially abrasion resistant film is a thermoplastic material and is polycarbonate.

36. The photochromic article of claim 33 further comprising an at least partial coating of an at least partially antireflective coating applied to the at least partially abrasion resistant film superposed on at least a portion of the superstrate.

37. The photochromic article of claim 1 wherein said photochromic article is substantially free of ultraviolet radiation absorbing materials adapted to substantially inhibit the activation of said photochromic material by radiation below 380 nanometers.

38. A photochromic article comprising:

a) a substrate; and b) a photochromic amount of at least one organic photochromic material b) adapted to change from an unactivated form to an activated form by radiation substantially in a wavelength range from 380 to 410 nanometers when measured over a range of from 380 to 700 nanometers, said photochromic article being adapted to exhibit an unactivated state luminous transmittance of greater than 70 percent at 23° C., an activated state luminous transmittance at saturation less than 30 percent when activated at 23° C. by simulated sunlight from a xenon arc lamp set at 6.7 Watts/meter$^2$ UVA and 50,000 lumens/meter$^2$, and an activated state luminous transmittance at saturation less than 60 percent when activated at 28° C. by simulated sunlight from a xenon arc lamp through an UV blocking transparency rendering an irradiance integrated between 380 and 420 nanometers of 0.75 Watts/meter$^2$ and 1,700 lumens/meter$^2$, wherein said photochromic material (b) is represented by graphic formula XIII

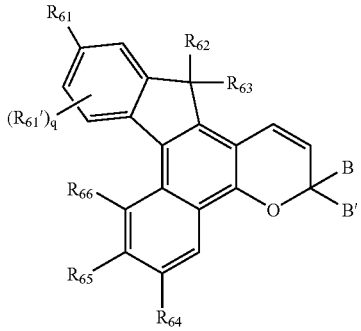

XIII wherein, (aa) $R_{61}$ is represented by:

(i) —$SR_{67}$, $R_{67}$ being chosen from $C_1$–$C_6$ alkyl, aryl, mono- or di-substituted aryl, said aryl group being phenyl or naphthyl and each of said aryl substituents being chosen independently from $C_1$–$C_6$ alkyl, $C_1$–$C_6$ alkoxy or halogen; or (ii) an amino group chosen from:

(1) —$N(R_{16})R_{17}$, $R_{16}$ and $R_{17}$ each being independently chosen from hydrogen, $C_1$–$C_8$ alkyl, aryl, furanyl, benzofuran-2-yl, benzofuran-3-yl, thienyl, benzothien-2-yl, benzothien-3-yl, dibenzofuranyl, dibenzothienyl, benzopyridyl, fluorenyl, $C_1$–$C_8$ alkylaryl, $C_3$–$C_{20}$ cycloalkyl, $C_4$–$C_{20}$ bicycloalkyl, $C_5$–$C_{20}$ tricycloalkyl or $C_1$–$C_{20}$ alkoxyalkyl and said aryl group being phenyl or naphthyl;

(2) a nitrogen containing ring represented by the following graphic formula:

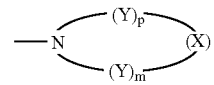

wherein each Y being independently chosen for each occurrence from —$CH_2$—, —$CH(R_{26})$—, —$C(R_{26})(R_{26})$—, —$CH(aryl)$-, —$C(aryl)_2$— or —$C(R_{26})(aryl)$-; X being —Y—, —O—, —S—, —S(O)—, —S(O_2)—, —NH—, —$N(R_{26})$— or —N(aryl)-; $R_{26}$ being $C_1$–$C_6$ alkyl; said aryl group being phenyl or naphthyl, m being chosen from the integer 1, 2 or 3 and p being chosen from the integer 0, 1, 2 or 3; provided that when p is 0, X is Y;

(3) a group represented by one of the following graphic formulae:

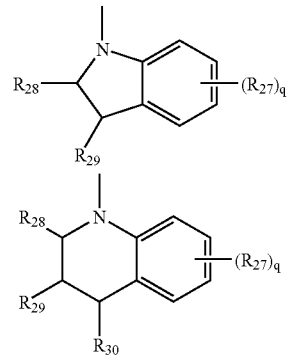

wherein each $R_{28}$, $R_{29}$ and $R_{30}$ being chosen independently for each occurrence in each formula from hydrogen, $C_1$–$C_5$ alkyl, phenyl or naphthyl; or the groups $R_{28}$ and $R_{29}$ together form a ring of 5 to 8 carbon atoms; $R_{27}$ being chosen independently for each occurrence from $C_1$–$C_6$ alkyl, $C_1$–$C_6$ alkoxy, fluoro or chloro and q being chosen from the integer 0, 1 or 2;

(4) unsubstituted, mono- or di-substituted $C_4$–$C_{18}$ spirobicyclic amine; and (5) unsubstituted, mono- or di-substituted $C_4$–$C_{18}$ spirotricyclic amine; said substituents for (4) and (5) being independently chosen for each occurrence from aryl, $C_1$–$C_6$ alkyl, $C_{1-6}$ alkoxy or phenyl($C_1$–$C_6$)alkyl;

(bb) $R_{61}'$ is independently chosen for each occurrence from $C_1$–$C_6$ alkyl or $C_1$–$C_6$ alkoxy and q being chosen from the integer 0, 1 or 2;

(cc) $R_{62}$ and $R_{63}$ are each independently chosen from:

(i) hydrogen, hydroxy, amino, mono- or di-substituted amino, $C_1$–$C_{12}$ alkyl, $C_3$–$C_{12}$ alkylidene, $C_2$–$C_{12}$ alkylidyne, vinyl, $C_3$–$C_7$ cycloalkyl, $C_1$–$C_6$ alkoxyalkyl, allyl, benzyl, mono-substituted benzyl, chloro, fluoro or —C(O)W", wherein W" being hydroxy, $C_1$–$C_6$ alkyl, $C_1$–$C_6$ alkoxy, phenyl, mono-substituted phenyl, amino, mono($C_1$–$C_6$)alkylamino, di($C_1$–$C_6$)alkylamino, morpholino, piperidino or pyrrolidyl; said amino substituents in (cc)(i) being $C_1$–$C_6$ alkyl, phenyl, benzyl or naphthyl; each of said benzyl substituents being $C_1$–$C_6$ alkyl or $C_1$–$C_6$ alkoxy;

(ii) an unsubstituted, mono- di- or tri-substituted group chosen from phenyl, naphthyl, phenanthryl, pyrenyl, quinolyl, isoquinolyl, benzofuranyl, thienyl, benzothienyl, dibenzofuranyl, dibenzothienyl, carbazolyl, or indolyl; each of said group substituents in (cc)(ii) being chosen independently for each occurrence from chloro, fluoro, $C_1$–$C_6$ alkyl or $C_1$–$C_6$ alkoxy;

(iii) a monosubstituted phenyl, said phenyl having a substituent located at the para position being —$(CH_2)_r$— or —O—$(CH_2)_r$—, wherein r being chosen from the integer 1, 2, 3, 4, 5 or 6, said substituent being connected to an aryl group which is a member of another photochromic material;

(iv) —$OR_{67'}$, $R_{67'}$ being chosen from $C_1$–$C_6$ alkyl, $C_1$–$C_6$ acyl, phenyl($C_1$–$C_3$)alkyl, mono($C_1$–$C_6$) alkyl substituted phenyl($C_1$–$C_3$)alkyl, mono ($C_1$–$C_6$)alkoxy substituted phenyl($C_1$–$C_3$)alkyl, $C_1$–$C_6$ alkoxy($C_2$–$C_4$)alkyl, $C_3$–$C_7$ cycloalkyl, mono ($C_1$–$C_4$)alkyl substituted $C_3$–$C_7$ cycloalkyl, $C_1$–$C_6$ chloroalkyl, $C_1$–$C_6$ fluoroalkyl, allyl, triarylsilyl, triarylsilyloxy, tri($C_1$–$C_6$)alkylsilyl, tri($C_1$–$C_6$)alkylsilyloxy, tri($C_1$–$C_6$)alkoxysilyl, tri($C_1$–$C_6$)alkoxysilyloxy, di($C_1$–$C_6$)alkyl($C_1$–$C_6$ alkoxy)silyl, di($C_1$–$C_6$)alkyl($C_1$–$C_6$ alkoxy)silyloxy, di($C_1$–$C_6$)alkoxy($C_1$–$C_6$ alkyl)silyl, di($C_1$–$C_6$)alkoxy($C_1$–$C_6$ alkyl)silyloxy, benzoyl, mono-substituted benzoyl, naphthoyl or mono-substituted naphthoyl; each of said benzoyl and naphthoyl substituents being independently chosen from $C_1$–$C_6$ alkyl or $C_1$–$C_6$ alkoxy; or $R_{67'}$ being —$CH(R_{68})Q''$, wherein $R_{68}$ being chosen from hydrogen or $C_1$–$C_3$ alkyl and Q'' being chosen from —CN, —$CF_3$, or $COOR_{68}$; $R_{67'}$ being —C(O)V'', wherein V'' being chosen from hydrogen, $C_1$–$C_6$ alkoxy, phenoxy, mono- or di-($C_1$–$C_6$)alkyl substituted phenoxy, mono- or di-($C_1$–$C_6$)alkoxy substituted phenoxy, an unsubstituted, mono- or di-substituted aryl group, phenyl or naphthyl, amino, mono($C_1$–$C_6$)alkylamino, di($C_1$–$C_6$)alkylamino, phenylamino, mono- or di-($C_1$–$C_6$)alkyl substituted phenylamino, or mono- or di- $C_1$–$C_6$ alkoxy substituted phenylamino; each of said aryl group substituents being independently chosen from $C_1$–$C_6$ alkyl or $C_1$–$C_6$ alkoxy;

(v) $CH(Q''')_2$, Q''' being chosen from —CN or $COOR_{69}$ and $R_{69}$ being chosen from hydrogen, $C_1$–$C_6$ alkyl, phenyl($C_1$–$C_3$)alkyl, mono($C_1$–$C_6$) alkyl substituted phenyl($C_1$–$C_3$)alkyl, mono ($C_1$–$C_6$)alkoxy substituted phenyl($C_1$–$C_3$)alkyl or an unsubstituted, mono- or di-substituted aryl group, phenyl or naphthyl; each of said aryl group substituents being independently chosen from $C_1$–$C_6$ alkyl or $C_1$–$C_6$ alkoxy:

(vi) —$CH(R_{70})G''$, $R_{70}$ being chosen from hydrogen, $C_1$–$C_6$ alkyl or an unsubstituted, mono- or di-substituted aryl group, phenyl or naphthyl, and G'' being chosen from —$COOR_{69}$, —$COR_{71}$ or —$CH_2OR_{72}$, wherein $R_{71}$ being chosen from hydrogen, $C_1$–$C_6$ alkyl, an unsubstituted, mono- or di-substituted aryl group, phenyl or naphthyl, amino, mono ($C_1$–$C_6$)alkylamino, di($C_1$–$C_6$)alkylamino, phenylamino, mono- or di-($C_1$–$C_6$)alkyl substituted phenylamino, mono- or di-($C_1$–$C_6$) alkoxy substituted phenylamino, diphenylamino, mono- or di($C_1$–$C_6$)alkyl substituted diphenylamino, mono- or di($C_{1-C6}$)alkoxy substituted diphenylamino, morpholino or piperidino; $R_{72}$ being chosen from hydrogen, —$C(O)R_{69}$, $C_1$–$C_6$ alkyl, $C_1$–$C_3$ alkoxy($C_1$–$C_6$)alkyl, phenyl($C_1$–$C_3$) alkyl, mono($C_1$–$C_6$)alkoxy substituted phenyl ($C_1$–$C_3$)alkyl or an unsubstituted, mono- or di-substituted aryl group, phenyl or naphthyl, each of said aryl group substituents being independently chosen from $C_1$–$C_6$ alkyl or $C_1$–$C_6$ alkoxy;

(vii) the group T wherein the group T is represented by the formula:

wherein -G being chosen from —C(O)— or —$CH_2$—, G' being chosen from $C_1$–$C_3$ alkoxy or a polymerizable group, x, y and z each being independently chosen from a number between 0 and 50, and the sum of x, y and z being between 2 and 50; or (viii) $R_{62}$ and $R_{63}$ together form an oxo group or a substituted or unsubstituted spiro-carbocyclic ring containing 3 to 6 carbon atoms or a substituted or unsubstituted spiro-heterocyclic group containing 1 or 2 oxygen atoms and 3 to 6 carbon atoms including the spirocarbon atom, said spiro-carbocyclic ring and spiro-heterocyclic group being annellated with 0, 1 or 2 benzene rings, said substituents being hydrogen or $C_1$–$C_6$ alkyl;

(dd) $R_{64}$ is hydrogen or $C_1$–$C_6$ alkyl;

(ee) $R_{65}$ is hydrogen or $C_1$–$C_6$ alkyl;

(ff) $R_{66}$ is chosen from hydrogen, $C_1$–$C_6$ alkyl or the group $R_a$, said $R_a$ chosen from:

(i) —$OR_{73}$, $R_{73}$ being chosen from phenyl($C_1$–$C_3$) alkyl, $C_1$–$C_6$ alkyl, mono($C_1$–$C_6$)alkyl substituted phenyl($C_1$–$C_3$)alkyl, mono($C_1$–$C_6$)alkoxy substituted phenyl($C_1$–$C_3$)alkyl, $C_1$–$C_6$ alkoxy($C_2$–$C_4$) alkyl, $C_3$–$C_7$ cycloalkyl, mono($C_1$–$C_4$)alkyl substituted $C_3$–$C_7$ cycloalkyl, $C_1$–$C_6$ chloroalkyl, $C_1$–$C_6$ fluoroalkyl, allyl or —$CH(R_{68})Q''$ described in (cc)(i); or (ii) an amino group being the same described hereinbefore in (aa)(ii);

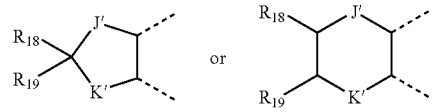

and (gg) B and B' are each independently chosen from (i) mono-T-substituted phenyl, wherein the group T is the same as described hereinbefore in (c)(vii);

(ii) an unsubstituted, mono-, di-, or tri-substituted aryl group, phenyl or naphthyl;

(iii) 9-julolidinyl or the unsubstituted, mono- or di-substituted heteroaromatic group chosen from pyridyl furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl or fluorenyl, each of said aryl and heteroaromatic substituents in (hh)(ii) and (iii) being independently chosen from hydroxy, —C(O)U, wherein U being hydroxy, $C_1$–$C_6$ alkyl, $C_{1-C6}$ alkoxy, phenyl, mono-substituted phenyl, amino, mono $(C_1-C_6)$alkylamino, di-$(C_1-C_6)$alkylamino, morpholino, piperidino or pyrrolidyl; aryl, mono$(C_1-C_6)$ alkoxyaryl, di$(C_1-C_6)$ alkoxyaryl, mono$(C_1-C_6)$alkylaryl, di$(C_1-C_6)$ alkylaryl, chloroaryl, fluoroaryl, $C_3-C_7$ cycloalkylaryl, $C_3-C_7$ cycloalkyl, $C_3-C_7$ cycloalkyloxy, $C_3-C_7$ cycloalkyloxy$(C_1-C_6)$alkyl, $C_3-C_7$ cycloalkyloxy$(C_1-C_6)$alkoxy, aryl$(C_1-C_6)$alkyl, aryl$(C_1-C_6)$alkoxy, aryloxy, aryloxy$(C_1-C_6)$ alkyl, aryloxy$(C_1-C_6)$alkoxy, mono- or di-$(C_1-C_6)$alkylaryl $(C_1-C_6)$alkyl, mono- or di-$(C_1-C_6)$alkoxyaryl$(C_1-C_6)$alkyl, mono- or di-$(C_1-C_6)$alkylaryl$(C_1-C_6)$alkoxy, mono- or di-$(C_1-C_6)$alkoxyaryl $(C_1-C_6)$alkoxy, amino, mono $(C_1-C_6)$alkylamino, di$(C_1-C_6)$alkylamino, diarylamino, piperazino, N-$(C_1-C_6)$alkylpiperazino, N-arylpiperazino, aziridino, indolino, piperidino, morpholino, thiomorpholino, tetrahydroquinolino, tetrahydroisoquinolino, pyrrolidyl, $C_1-C_6$ alkyl, $C_1-C_6$ chloroalkyl, $C_1-C_6$ fluoroalkyl, $C_1-C_6$ alkoxy, mono$(C_1-C_6)$alkoxy$(C_1C_4)$ alkyl, acryloxy, methacryloxy, bromo, chloro or fluoro, said aryl being chosen from phenyl or naphthyl;

(iv) an unsubstituted or mono-substituted group chosen from pyrazolyl, imidazolyl, pyrazolinyl, imidazolinyl, pyrrolinyl, phenothiazinyl, phenoxazinyl, phenazinyl or acridinyl, each of said substituents being independently chosen from $C_1-C_6$ alkyl, $C_1-C_6$ alkoxy, phenyl, fluoro, chloro or bromo;

(v) a monosubstituted phenyl, said phenyl having a substituent located at the para position being —$(CH_2)_r$— or —O—$(CH_2)_r$—, wherein r being chosen from the integer 1, 2, 3, 4, 5 or 6, said substituent being connected to an aryl group which is a member of another photochromic material, and;

(vi) a group represented by one of the following graphic formulae:

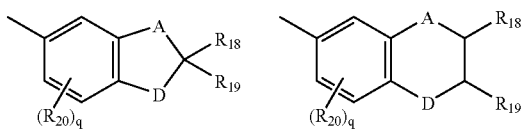

wherein A being independently chosen in each formula from methylene or oxygen and D being independently chosen in each formula from oxygen or substituted nitrogen, provided that when D is substituted nitrogen, A is methylene; said nitrogen substituents being chosen from hydrogen, $C_1-C_6$ alkyl, or $C_2-C_6$ acyl; each $R_{20}$ being independently chosen for each occurrence in each formula from $C_1-C_6$ alkyl, $C_1-C_6$ alkoxy, hydroxy, chloro or fluoro; $R_{18}$ and $R_{19}$ each being independently chosen in each formula from hydrogen or $C_1-C_6$ alkyl; and q being chosen from the integer 0, 1 or 2;

(vii) $C_1-C_6$ alkyl, $C_1-C_6$ chloroalkyl, $C_1-C_6$ fluoroalkyl, $C_1-C_6$ alkoxy$(C_1-C_4)$alkyl, $C_3-C_6$ cycloalkyl, mono$(C_1-C_6)$alkoxy$(C_3-C_6)$cycloalkyl, mono$(C_1-C_6)$alkyl$(C_3-C_6)$-cycloalkyl, chloro$(C_3-C_6)$cycloalkyl, fluoro$(C_3-C_6)$cycloalkyl or $C_4-C_{12}$ bicycloalkyl;

(viii) a group represented by the following graphic formula:

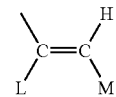

wherein L being chosen from hydrogen or $C_1-C_4$ alkyl and M being chosen from an unsubstituted, mono-, or di-substituted group chosen from naphthyl, phenyl, furanyl, or thienyl; each of said group substituents being independently chosen from $C_1-C_4$ alkyl, $C_1-C_4$ alkoxy, fluoro, or chloro; or (ix) B and B' taken together form fluoren-9-ylidene, mono-, or di-substituted fluoren-9-ylidene or a group being independently chosen from saturated $C_3-C_{12}$ spiro-monocyclic hydrocarbon rings, saturated $C_7-C_{12}$ spiro-bicyclic hydrocarbon rings or saturated $C_7-C_{12}$ spiro-tricyclic hydrocarbon rings; each of said fluoren-9-ylidene substituents being independently chosen from $C_1-C_4$ alkyl, $C_1-C_4$ alkoxy, fluoro or chloro.

39. The photochromic article of claim 38 wherein the photochromic article is adapted to exhibit an unactivated state luminous transmittance of greater than 80 percent at 23° C., an activated state luminous transmittance at saturation less than 30 percent when activated at 23° C. by simulated sunlight from a xenon arc lamp set at 6.7 Watts/meter² UVA and 50,000 lumens/meter², and an activated state luminous transmittance at saturation less than 40 percent when activated at 28° C. by simulated sunlight from a xenon arc lamp through an UV blocking transparency rendering an irradiance integrated between 380 and 420 nanometers of 0.75 Watts/meter² and 1,700 lumens/meter².

40. The photochromic article of claim 38 wherein the UV blocking transparency is a vehicular windshield.

41. The photochromic article of claim 38 further comprising at least one fixed tint dye.

42. The photochromic article of claim 38 wherein said photochromic article is adapted to exhibit a neutral activated color.

43. The photochromic article of claim 38 wherein photochromic material (b) is chosen from:
(a) a single photochromic compound;
(b) a mixture of photochromic compounds;
(c) a material comprising at least one photochromic compound;
(d) a material to which at least one photochromic compound is chemically bonded;
(e) material (c) or (d) further comprising a coating to substantially prevent contact of the at least one photochromic compound with external materials;
(f) a photochromic polymer; or
(g) mixtures thereof.

44. The photochromic article of claim 38 further comprising at least one other photochromic material (c) that is different from photochromic material (b).

45. The photochromic article of claim 44 wherein photochromic material (c) is chosen from:
(a) a single photochromic compound;
(b) a mixture of photochromic compounds;

(c) a material comprising at least one photochromic compound;
(d) a material to which at least one photochromic compound is chemically bonded;
(e) material (c) or (d) further comprising a coating to substantially prevent contact of the at least one photochromic compound with external materials;
(f) a photochromic polymer; or
(g) mixtures thereof.

46. The photochromic article of claim 38 further comprising an at least partial coating of an at least partially abrasion resistant coating.

47. The photochromic article of claim 46 further comprising an at least partial coating of an at least partially antireflective coating.

48. The photochromic article of claim 38 wherein the substrate comprises at least one photochromic material (b).

49. The photochromic article of claim 48 wherein the substrate further comprises at least one photochromic material (c) that is different from photochromic material (b).

50. The photochromic article of claim 38 further comprising an at least partial coating of an at least partially cured polymeric coating applied to at least one surface of the substrate.

51. The photochromic article of claim 50 wherein the at least partially cured polymeric coating comprises photochromic material (b).

52. The photochromic article of claim 51 wherein the at least partially cured polymeric coating further comprises at least one other photochromic material (c) that is different from photochromic material (b).

53. The photochromic article of claim 50 wherein the at least partially cured polymeric coating is a polymeric coating of thermoplastic or thermosetting materials.

54. The photochromic article of claim 53 wherein the at least partially cured polymeric coating is a polymeric coating of thermosetting materials chosen from polyurethanes, aminoplast resins, poly(meth)acrylates, polyanhydrides, polyacrylamides, epoxy resins or polysilanes.

55. The photochromic article of claim 50 further comprising an at least partial coating of primer interposed between the at least partially cured polymeric coating and the substrate.

56. The photochromic article of claim 55 further comprising an at least partial coating of an at least partially abrasion resistant coating applied to the surface of the at least partially cured polymeric coating.

57. The photochromic article of claim 56 further comprising an at least partial coating of an at least partially antireflective coating.

58. The photochromic article of claim 38 wherein the substrate is chosen from paper, glass, ceramic, wood, masonry, textile, metal or organic polymeric material.

59. The photochromic article of claim 58 wherein the substrate is organic polymeric material and said organic polymeric material is chosen from poly($C_1$–$C_{12}$ alkyl methacrylates), poly(oxyalkylene dimethacrylates), poly(alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), thermoplastic polycarbonates, polyesters, polyurethanes, poly(ethylene terephthalate), polystyrene, poly(alpha methylstyrene), copoly(styrene-methylmethacrylate), copoly(styrene-acrylonitrile), polyvinylbutyral or is polymerized from monomers chosen from bis(allyl carbonate) monomers, polyfunctional acrylate monomers, polyfunctional methacrylate monomers, diethylene glycol dimethacrylate monomers, diisopropenyl benzene monomers, ethoxylated bisphenol A dimethacrylate monomers, ethylene glycol bismethacrylate monomers, poly (ethylene glycol) bismethacrylate monomers, ethoxylated phenol bis methacrylate monomers, alkoxylated polyhydric alcohol polyacrylate monomers, styrene monomers, urethane acrylate monomers, glycidyl acrylate monomers, glycidyl methacrylate monomers, diallylidene pentaerythritol monomers or mixtures thereof.

60. The photochromic article of claim 59 wherein the substrate is an organic polymeric material and said organic polymeric material is an optical element.

61. The photochromic article of claim 60 wherein the substrate is an optical element and said optical element is an ophthalmic lens.

62. The photochromic article of claim 38 further comprising a superstrate connected to at least a portion of the substrate, said superstrate comprising at least one organic polymeric material.

63. The photochromic article of claim 62 wherein the superstrate comprises photochromic material (b).

64. The photochromic article of claim 63 wherein the superstrate further comprises at least one other photochromic material (c) that is different from photochromic material (b).

65. The photochromic article of claim 62 wherein the superstrate is adheringly bonded to at least a portion of the substrate.

66. The photochromic article of claim 62 wherein the superstrate is an organic polymeric material chosen from thermosetting or thermoplastic materials.

67. The photochromic article of claim 66 wherein the superstrate is a thermoplastic material and is polyurethane.

68. The photochromic article of claim 62 further comprising an at least partially abrasion resistant film superposed on at least a portion of the superstrate.

69. The photochromic article of claim 68 wherein the at least partially abrasion resistant film is an organic polymeric material chosen from thermoplastic and thermosetting materials.

70. The photochromic article of claim 69 wherein the at least partially abrasion resistant film is a thermoplastic material and is polycarbonate.

71. The photochromic article of claim 70 further comprising an at least partial coating of an at least partially antireflective coating.

72. A method for producing a photochromic article adapted to retain at least 12 percent of the delta OD measured in the Outdoor Test when tested in the Behind the Windshield Test comprising:
a) obtaining a substrate;
b) obtaining an organic photochromic material (b) adapted to change from an unactivated form to an activated form by exposure to radiation substantially in the wavelength range from 380 to 410 nanometers when measured over a range of from 380 to 700 nanometers;
c) introducing a photochromic amount of said photochromic material (b) together with said substrate by a method chosen from:
i) introducing photochromic material (b) with the starting materials used to form said substrate;
ii) at least partially imbibing photochromic material (b) into at least one surface of said substrate;
iii) applying at least a partial coating of a polymeric coating composition comprising photochromic material (b) to at least one surface of said substrate;

iv) at least partially connecting a superstrate comprising photochromic material (b) to at least one surface of said substrate; or v) combinations of i), ii), ii) or iv), said photochromic material (b) is represented by the following graphic formula XIII wherein:

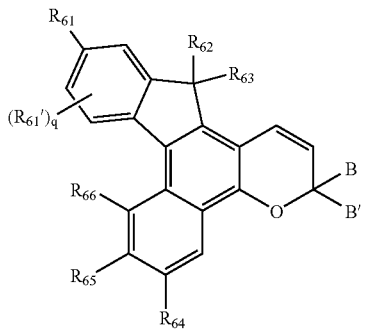

XIII wherein, (aa) $R_{61}$ is represented by:

(i) —$SR_{67}$, $R_{67}$ being chosen from $C_1$–$C_6$ alkyl, aryl, mono- or di-substituted aryl, said aryl group being phenyl or naphthyl and each of said aryl substituents being chosen independently from $C_1$–$C_6$ alkyl, $C_1$–$C_6$ alkoxy or halogen; or (ii) an amino group chosen from:

(1) —$N(R_{16})R_{17}$, $R_{16}$ and $R_{17}$ each being independently chosen from hydrogen, $C_1$–$C_8$ alkyl, aryl, furanyl, benzofuran-2-yl, benzofuran-3-yl, thienyl, benzothien-2-yl, benzothien-3-yl, dibenzofuranyl, dibenzothienyl, benzopyridyl, fluorenyl, $C_1$–$C_8$ alkylaryl, $C_3$–$C_{20}$ cycloalkyl, $C_4$–$C_{20}$ bicycloalkyl, $C_5$–$C_{20}$ tricycloalkyl or $C_1$–$C_{20}$ alkoxyalkyl and said aryl group being phenyl or naphthyl;

(2) a nitrogen containing ring represented by the following graphic formula:

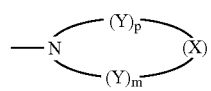

wherein each Y being independently chosen for each occurrence from —$OH_2$—, —$CH(R_{26})$—, —$C(R_{26})(R_{26})$—, —$CH(aryl)$-, —$C(aryl)_2$— or —$C(R_{26})(aryl)$-; X being —Y—, —O—, —S—, —$S(O)$—, —$S(O_2)$—, —NH—, —$N(R_{26})$— or —$N(aryl)$-; $R_{26}$ being $C_1$–$C_6$ alkyl; said aryl group being phenyl or naphthyl, m being chosen from the integer 1, 2 or 3 and p being chosen from the integer 0, 1, 2 or 3; provided that when p is 0, X is Y;

(3) a group represented by one of the following graphic formulae:

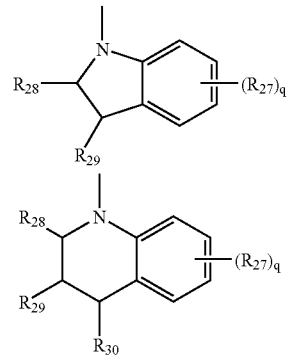

wherein each $R_{28}$, $R_{29}$ and $R_{30}$ being chosen independently for each occurrence in each formula from hydrogen, $C_1$–$C_5$ alkyl, phenyl or naphthyl; or the groups $R_{28}$ and $R_{29}$ together form a ring of 5 to 8 carbon atoms; $R_{27}$ being chosen independently for each occurrence from $C_1$–$C_6$ alkyl, $C_1$–$C_6$ alkoxy, fluoro or chloro and q being chosen from the integer 0, 1 or 2;

(4) unsubstituted, mono- or di- substituted $C_4$–$C_{18}$ spirobicyclic amine; and (5) unsubstituted, mono- or di- substituted $C_4$–$C_{18}$ spirotricyclic amine; said substituents for (4) and (5) being independently chosen for each occurrence from aryl, $C_1$–$C_6$ alkyl, $C_1$–$C_6$ alkoxy or phenyl ($C_1$–$C_6$)alkyl;

(bb) $R_{61}$' is independently chosen for each occurrence from $C_1$–$C_6$ alkyl or $C_1$–$C_6$ alkoxy and q being chosen from the integer 0, 1 or 2;

(cc) $R_{62}$ and $R_{63}$ are each independently chosen from:

(i) hydrogen, hydroxy, amino, mono- or di-substituted amino, $C_1$–$C_{12}$ alkyl, $C_3$–$C_{12}$ alkylidene, $C_2$–$C_{12}$ alkylidyne, vinyl, $C_3$–$C_7$ cycloalkyl, $C_1$–$C_6$ alkoxyalkyl, allyl, benzyl, mono-substituted benzyl, chloro, fluoro or —C(O)W", wherein W" being hydroxy, $C_1$–$C_6$ alkyl, $C_1$–$C_6$ alkoxy, phenyl, mono-substituted phenyl, amino, mono($C_1$–$C_6$)alkylamino, di($C_1$–$C_6$)alkylamino, morpholino, piperidino or pyrrolidyl; said amino substituents in (cc)(i) being $C_1$–$C_6$ alkyl, phenyl, benzyl or naphthyl; each of said benzyl substituents being $C_1$–$C_6$ alkyl or $C_1$–$C_6$ alkoxy;

(ii) an unsubstituted, mono- di- or tri-substituted group chosen from phenyl, naphthyl, phenanthryl, pyrenyl, quinolyl, isoquinolyl, benzofuranyl, thienyl, benzothienyl, dibenzofuranyl, dibenzothienyl, carbazolyl or indolyl; each of said group substituents in (cc)(ii) being chosen independently for each occurrence from chloro, fluoro, $C_1$–$C_6$ alkyl or $C_1$–$C_6$ alkoxy;

(iii) a monosubstituted phenyl, said phenyl having a substituent located at the para position being —$(CH_2)_r$— or —O—$(CH_2)_r$—, wherein r being chosen from the integer 1, 2, 3, 4, 5 or 6, said substituent being connected to an aryl group which is a member of another photochromic material;

(iv) —$OR_{67'}$, $R_{67'}$ being chosen from $C_1$–$C_6$ alkyl, $C_1$–$C_6$ acyl, phenyl($C_1$–$C_3$)alkyl, mono $C_1$–$C_6$ alkyl substituted phenyl($C_1$–$C_3$)alkyl, mono($C_1$–$C_6$) alkoxy substituted phenyl($C_1$–$C_3$)alkyl, $C_1$–$C_6$ alkoxy($C_2$–$C_4$)alkyl, $C_3$–$C_7$ cycloalkyl, mono ($C_1$–$C_4$)alkyl substituted $C_3$–$C_7$ cycloalkyl, $C_1$–$C_6$ chloroalkyl, $C_1$–$C_6$ fluoroalkyl, allyl, triarylsilyl, triarysilyloxy, tri($C_1$–$C_6$)alkylsilyl, tri($C_1$–$C_6$)alkylsilyloxy, tri($C_1$–$C_6$)alkoxysilyl, tri($C_1$–$C_6$)alkoxysilyloxy, di($C_1$–$C_6$)alkyl($C_1$–$C_6$ alkoxy)silyl, di($C_1$–$C_6$)alklyl($C_1$–$C_6$alkoxy)silyloxy, di($C_1$–$C_6$)alkoxy($C_1$–$C_6$ alkyl)silyl, di($C_1$–$C_6$) alkoxy($C_1$–$C_6$alkyl)silyloxy, benzoyl, mono-substituted benzoyl, naphthoyl or mono-substituted naphthoyl; each of said benzoyl and naphthoyl substituents being independently chosen from $C_1$–$C_6$ alkyl or $C_1$–$C_6$ alkoxy; or $R_{67'}$ being —CH($R_{68}$)Q″, wherein $R_{68}$ being chosen from hydrogen or $C_1$–$C_3$ alkyl and Q″ being chosen from —CN, —$CF_3$, or —COO$R_{68}$; $R_{67'}$ being —C(O)V″, wherein V″ being chosen from hydrogen, $C_1$–$C_6$ alkoxy, phenoxy, mono- or di-($C_1$–$C_6$)alkyl substituted phenoxy, mono- or di-($C_1$–$C_6$)alkoxy substituted phenoxy, an unsubstituted, mono- or di-substituted aryl group, phenyl or naphthyl, amino, mono($C_1$–$C_6$)alkylamino, di($C_1$–$C_6$)alkylamino, phenylamino, mono- or di-($C_1$–$C_6$)alkyl substituted phenylamino, or mono- or di-($C_1$–$C_6$)alkoxy substituted phenylamino; each of said aryl group substituents being independently chosen from $C_1$–$C_6$ alkyl or $C_1$–$C_6$ alkoxy;

(v) —CH(Q‴)$_2$, Q‴ being chosen from —CN or —COO$R_{69}$ and $R_{69}$ being chosen from hydrogen, $C_1$–$C_6$ alkyl, phenyl($C_1$–$C_3$)alkyl, mono($C_1$–$C_6$) alkyl substituted phenyl($C_1$–$C_3$)alkyl, mono($C_1$–$C_6$) alkoxy substituted phenyl($C_1$–$C_3$)alkyl or an unsubstituted, mono- or di-substituted aryl group, phenyl or naphthyl; each of said aryl group substituents being independently chosen from $C_1$–$C_6$ alkyl or $C_1$–$C_6$ alkoxy;

(vi) —OH($R_{70}$)G″, $R_{70}$ being chosen from hydrogen, $C_1$–$C_6$ alkyl or an unsubstituted, mono- or di-substituted aryl group, phenyl or naphthyl, and G″ being chosen from —COO$R_{69}$, —CO$R_{71}$ or —$CH_2OR_{72}$ wherein $R_{71}$, being chosen from hydrogen, $C_1$–$C_6$ alkyl, an unsubstituted, mono- or di-substituted aryl group, phenyl or naphthyl, amino, mono($C_1$–$C_6$) alkylamino, di($C_1$–$C_6$)alkylamino, phenylamino, mono- or di-($C_1$–$C_6$)alkyl substituted phenylamino, mono- or di-($C_1$–$C_6$)alkoxy substituted phenylamino, diphenylamino, mono- or di($C_1$–$C_6$)alkyl substituted diphenylamino, mono- or di($C_1$–$C_6$) alkoxy substituted diphenylamino, morpholino or piperidino; $R_{72}$ being chosen from hydrogen, —C(O)$R_{69}$, $C_1$–$C_6$ alkyl, $C_1$–$C_3$ alkoxy($C_1$–$C_6$) alkyl, phenyl($C_1$–$C_3$)alkyl, mono($C_1$–$C_6$)alkoxy substituted phenyl($C_1$–$C_3$)alkyl or an unsubstituted, mono- or di-substituted aryl group, phenyl or naphthyl, each of said aryl group substituents being independently chosen from $C_1$–$C_6$ alkyl or $C_1$–$C_6$ alkoxy;

(vii) the group T wherein the group T is represented by the formula:

wherein -G being chosen from —C(O)— or —$CH_2$—, G′ being chosen from $C_1$–$C_3$ alkoxy or a polymerizable group, x, y and z each being independently chosen from a number between 0 and 50, and the sum of x, y and z being between 2 and 50: or (viii) $R_{62}$ and $R_{63}$ together form an oxo group or a substituted or unsubstituted spiro-carbocyclic ring containing 3 to 6 carbon atoms or a substituted or unsubstituted spiro-heterocyclic group containing 1 or 2 oxygen atoms and 3 to 6 carbon atoms including the spirocarbon atom, said spiro-carbocyclic ring and spiro-heterocyclic group being annellated with 0, 1 or 2 benzene rings, said substituents being hydrogen or $C_1$–$C_6$ alkyl;

(dd) $R_{64}$ is hydrogen or $C_1$–$C_6$ alkyl (ee) $R_{65}$ is hydrogen or $C_1$–$C_6$ alkyl;

(ff) $R_{66}$ is chosen from hydrogen, $C_1$–$C_6$ alkyl or $R_a$, said $R_a$ chosen from:

(i) —O$R_{73}$, $R_{73}$ being chosen from phenyl($C_1$–$C_3$) alkyl, $C_1$–$C_6$ alkyl, mono($C_1$–$C_6$)alkyl substituted phenyl($C_1$–$C_3$)alkyl, mono($C_1$–$C_6$)alkoxy substituted phenyl($C_1$–$C_3$)alkyl, $C_1$–$C_6$alkoxy($C_2$–$C_4$) alkyl, $C_3$–$C_7$ cycloalkyl, mono($C_1$–$C_4$)alkyl substituted $C_3$–$C_7$ cycloalkyl, $C_1$–$C_6$ chloroalkyl, $C_1$–$C_6$ fluoroalkyl, allyl or —CH($R_{68}$)Q″ described in (cc)(i);

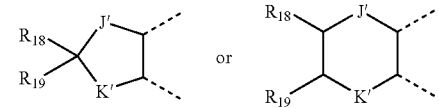

and (gg) B and B′ are each independently chosen from (i) mono-T-substituted phenyl, wherein the group T is the same as described hereinbefore in (cc)(vii);

(ii) an unsubstituted, mono-, di-, or tri-substituted aryl group, phenyl or naphthyl;

(iii) 9-julolidinyl or the unsubstituted, mono- or di-substituted heteroaromatic group chosen from pyridyl furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl or fluorenyl, each of said aryl and heteroaromatic substituents in (hh)(ii) and (iii) being independently chosen from hydroxy, —C(O)U, wherein U being hydroxy, $C_1$–$C_6$ alkyl, $C_1$–$C_6$ alkoxy, phenyl, mono-substituted phenyl, amino, mono ($C_1$–$C_6$)alkylamino, di-($C_1$–$C_6$) alkylamino, morpholino, piperidino or pyrrolidyl; aryl, mono($C_1$–$C_6$)alkoxyaryl, di($C_1$–$C_6$) alkoxyaryl, mono($C_1$–$C_6$)alkylaryl, di($C_1$–$C_6$) alkylaryl, chloroaryl, fluoroaryl, $C_3$–$C_7$ cycloalkylaryl, $C_3$–$C_7$ cycloalkyl, $C_3$–$C_7$ cycloalkyloxy, $C_3$–$C_7$ cycloalkyloxy($C_1$–$C_6$)alkyl, $C_3$–$C_7$ cycloalkyloxy($C_1$–$C_6$)alkoxy, aryl($C_1$–$C_6$)alkyl, aryl($C_1$–$C_6$)alkoxy, aryloxy, aryloxy($C_1$–$C_6$)alkyl, aryloxy($C_1$–$C_6$)alkoxy, mono- or di-($C_1$–$C_6$)alkylaryl($C_1$–$C_6$)alkyl, mono- or di-($C_1$–$C_6$) alkoxyaryl($C_1$–$C_6$)alkyl, mono- or di-($C_1$–$C_6$) alkylaryl($C_1$–$C_6$)alkoxy, mono- or di-($C_1$–$C_6$) alkoxyaryl($C_1$–$C_6$)alkoxy, amino, mono($C_1$–$C_6$) alkylamino, di($C_1$–$C_6$)alkylamino, diarylamino, piperazino, N—($C_1$–$C_6$)alkylpiperazino, N-arylpiperazino, aziridino, indolino, piperidino, morpholino, thiomorpholino, tetrahydroquinolino, tetrahydroisoquinolino, pyrrolidyl, $C_1$–$C_6$ alkyl, $C_1$–$C_6$ chloroalkyl, $C_1$–$C_6$ fluoroalkyl, $C_1$–$C_6$ alkoxy, mono($C_1$–$C_6$)alkoxy($C_1$–$C_4$)alkyl, acryloxy, methacryloxy, bromo, chloro or fluoro, said aryl being chosen from phenyl or naphthyl;

(iv) an unsubstituted or mono-substituted group chosen from pyrazolyl, imidazolyl, pyrazolinyl, imidazolinyl, pyrrolinyl, phenothiazinyl, phenoxazinyl, phenazinyl or acridinyl, each of said substituents being independently chosen from $C_1$–$C_6$ alkyl, $C_1$–$C_6$ alkoxy, phenyl, fluoro, chloro or bromo;

(v) a monosubstituted phenyl, said phenyl having a substituent located at the para position being —$(CH_2)_r$— or —O—$(CH_2)_r$—, wherein r being chosen from the integer 1, 2, 3, 4, 5 or 6, said substituent being connected to an aryl group which is a member of another photochromic material, and;

(vi) a group represented by one of the following graphic formulae:

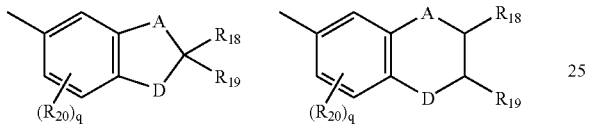

wherein A being independently chosen in each formula from methylene or oxygen and D being independently chosen in each formula from oxygen or substituted nitrogen, provided that when D is substituted nitrogen, A is methylene; said nitrogen substituents being chosen from hydrogen, $C_1$–$C_6$ alkyl, or $C_2$–$C_6$ acyl; each $R_{20}$ being independently chosen for each occurrence in each formula from $C_1$–$C_6$ alkyl, $C_1$–$C_6$ alkoxy, hydroxy, chloro or fluoro; $R_{18}$ and $R_{19}$ each being independently chosen in each formula from hydrogen or $C_1$–$C_6$ alkyl; and q being chosen from the integer 0, 1 or 2;

(vii) $C_1$–$C_6$ alkyl, $C_1$–$C_6$ chloroalkyl, $C_1$–$C_6$ fluoroalkyl, $C_1$–$C_6$ alkoxy($C_1$–$C_4$)alkyl, $C_3$–$C_6$ cycloalkyl, mono($C_1$–$C_6$)alkoxy($C_3$–$C_6$)cycloalkyl, mono($C_1$–$C_6$)alkyl($C_3$–$C_6$)-cycloalkyl, chloro($C_3$–$C_6$)cycloalkyl, fluoro($C_3$–$C_6$)cycloalkyl or $C_4$–$C_{12}$ bicycloalkyl;

(viii) a group represented by the following graphic formula:

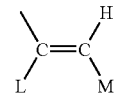

wherein L being chosen from hydrogen or $C_1$–$C_4$ alkyl and M being chosen from an unsubstituted, mono-, or di-substituted group chosen from naphthyl, phenyl, furanyl, or thienyl; each of said group substituents being independently chosen from $C_1$–$C_4$ alkyl, $C_1$–$C_4$ alkoxy, fluoro, or chloro; or (ix) B and B' taken together form fluoren-9-ylidene, mono-, or di-substituted fluoren-9-ylidene or a group being independently chosen from saturated $C_3$–$C_{12}$ spiro-monocyclic hydrocarbon rings, saturated $C_7$–$C_{12}$ spiro-bicyclic hydrocarbon rings or saturated $C_7$–$C_{12}$ spiro-tricyclic hydrocarbon rings; each of said fluoren-9-ylidene substituents being independently chosen from $C_1$–$C_4$ alkyl, $C_1$–$C_4$ alkoxy, fluoro or chloro.

73. The method of claim 72 further comprising adding a photochromic material (c) that is different from photochromic material (b), in (c) (i), (ii), (iii), (iv) or (v).

74. The method of claim 72 further comprising adding a fixed tint dye in (c) (i), (ii), (iii), (iv) or (v).

* * * * *